(12) United States Patent  
Michelson

(10) Patent No.: US 7,722,619 B2
(45) Date of Patent: May 25, 2010

(54) METHOD OF MAINTAINING DISTRACTION OF A SPINAL DISC SPACE

(75) Inventor: Gary Karlin Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 929 days.

(21) Appl. No.: 11/410,634

(22) Filed: Apr. 25, 2006

(65) Prior Publication Data

US 2006/0200164 A1 Sep. 7, 2006

Related U.S. Application Data

(60) Division of application No. 10/883,382, filed on Jul. 1, 2004, now Pat. No. 7,686,805, which is a division of application No. 09/605,001, filed on Jun. 27, 2000, which is a continuation of application No. 08/396,414, filed on Feb. 27, 1995, now Pat. No. 6,080,155.

(51) Int. Cl.
*A61F 5/00* (2006.01)
(52) U.S. Cl. .......................................... 606/90; 606/105
(58) Field of Classification Search ................... 606/90, 606/105; 623/17.11, 17.16
See application file for complete search history.

(56) References Cited

U.S. PATENT DOCUMENTS

| 350,420 | A | 10/1886 | Dillon |
| 672,377 | A | 4/1901 | Kearns |
| 1,137,585 | A | 4/1915 | Craig |
| 2,065,659 | A | 12/1936 | Cullen |
| 2,181,746 | A | 11/1939 | Siebrandt |
| 2,243,718 | A | 5/1941 | De G. Moreira |
| 2,372,622 | A | 3/1945 | Fassio |

(Continued)

FOREIGN PATENT DOCUMENTS

DE 1961531 7/1970

(Continued)

OTHER PUBLICATIONS

Adams, et al.; Outline of Orthopaedics, Eleventh Edition; Trunk and Spine, p. 194.

(Continued)

*Primary Examiner*—Michael A. Brown
(74) *Attorney, Agent, or Firm*—Martin & Ferraro, LLP

(57) ABSTRACT

Apparatus and a method of inserting spinal implants is disclosed in which an intervertebral space is first distracted, a hollow sleeve having teeth at one end is then driven into the vertebrae adjacent that disc space. A drill is then passed through the hollow sleeve removing disc and bone in preparation for receiving the spinal implant which is then inserted through the sleeve. Apparatus and a method of inserting spinal implants is disclosed in which an intervertebral space is first distracted to restore the normal angular relationship of the vertebrae adjacent to that disc space. An extended outer sleeve having extended portions capable of maintaining the vertebrae distracted in their normal angular relationship is then driven into the vertebrae adjacent that disc space. A drill is then passed through the hollow sleeve removing disc and bone in preparation for receiving the spinal implant which is then inserted through the sleeve.

19 Claims, 32 Drawing Sheets

U.S. PATENT DOCUMENTS

| | | | |
|---|---|---|---|
| 2,514,665 A | 7/1950 | Myller |
| 2,537,070 A | 1/1951 | Longfellow |
| 2,543,780 A | 3/1951 | Hipps et al. |
| 2,677,369 A | 5/1954 | Knowles |
| 2,774,350 A | 12/1956 | Cleveland |
| 2,789,558 A | 4/1957 | Rush |
| 2,832,343 A | 4/1958 | Mose |
| 2,842,131 A | 7/1958 | Smith |
| 2,878,809 A | 3/1959 | Treace |
| 3,085,786 A | 4/1963 | Raymond |
| 3,128,768 A | 4/1964 | Geistauts |
| 3,298,372 A | 1/1967 | Feinberg |
| 3,426,364 A | 2/1969 | Lumb |
| 3,486,505 A | 12/1969 | Morrison |
| 3,515,137 A | 6/1970 | Santomieri |
| 3,604,487 A | 9/1971 | Gilbert |
| 3,605,123 A | 9/1971 | Hahn |
| 3,618,611 A | 11/1971 | Urban |
| 3,696,812 A | 10/1972 | Jaycox |
| 3,709,219 A | 1/1973 | Halloran |
| 3,719,186 A | 3/1973 | Merig, Jr. |
| 3,720,959 A | 3/1973 | Hahn |
| 3,750,652 A | 8/1973 | Sherwin |
| 3,848,601 A | 11/1974 | Ma et al. |
| 3,855,638 A | 12/1974 | Pilliar |
| 3,867,728 A | 2/1975 | Stubstad et al. |
| 3,867,932 A | 2/1975 | Huene |
| 3,867,950 A | 2/1975 | Fischell |
| 3,875,595 A | 4/1975 | Froning |
| 3,888,260 A | 6/1975 | Fischell |
| 3,892,232 A | 7/1975 | Neufeld |
| 3,905,047 A | 9/1975 | Long |
| 3,915,151 A | 10/1975 | Kraus |
| 3,916,907 A | 11/1975 | Peterson |
| 3,918,440 A | 11/1975 | Kraus |
| 3,942,535 A | 3/1976 | Schulman |
| 3,948,262 A | 4/1976 | Zaffaroni |
| 3,952,334 A | 4/1976 | Bokros et al. |
| 3,987,499 A | 10/1976 | Scharbach et al. |
| 4,016,651 A | 4/1977 | Kawahara et al. |
| 4,027,392 A | 6/1977 | Sawyer et al. |
| D245,259 S | 8/1977 | Shen |
| 4,051,905 A | 10/1977 | Kleine |
| 4,059,115 A | 11/1977 | Jumashev et al. |
| 4,070,514 A | 1/1978 | Entherly et al. |
| 4,082,097 A | 4/1978 | Mann et al. |
| 4,086,701 A | 5/1978 | Kawahara et al. |
| 4,124,026 A | 11/1978 | Berner et al. |
| 4,142,517 A | 3/1979 | Stavropoulos et al. |
| 4,168,326 A | 9/1979 | Broemer et al. |
| 4,175,555 A | 11/1979 | Herbert |
| 4,177,524 A | 12/1979 | Grell et al. |
| 4,181,457 A | 1/1980 | Holmes |
| 4,197,850 A | 4/1980 | Schulman et al. |
| 4,206,516 A | 6/1980 | Pilliar |
| 4,222,128 A | 9/1980 | Tomonaga et al. |
| D257,511 S | 11/1980 | Zahn |
| 4,232,679 A | 11/1980 | Schulman |
| 4,237,948 A | 12/1980 | Jones et al. |
| 4,258,716 A | 3/1981 | Sutherland |
| 4,259,072 A | 3/1981 | Hirabayashi et al. |
| 4,262,369 A | 4/1981 | Roux |
| 4,271,832 A | 6/1981 | Evans et al. |
| D260,525 S | 9/1981 | Lassiter |
| 4,289,123 A | 9/1981 | Dunn |
| 4,293,962 A | 10/1981 | Fuson |
| 4,309,777 A | 1/1982 | Patil |
| 4,328,593 A | 5/1982 | Sutter et al. |
| 4,333,469 A | 6/1982 | Jeffcoat et al. |
| 4,341,206 A | 7/1982 | Perrett et al. |
| 4,349,921 A | 9/1982 | Kuntz |
| 4,356,572 A | 11/1982 | Guillemin et al. |
| 4,386,603 A | 6/1983 | Mayfield |
| 4,401,112 A | 8/1983 | Rezaian |
| 4,405,319 A | 9/1983 | Cosentino |
| 4,414,979 A | 11/1983 | Hirshorn et al. |
| 4,423,721 A | 1/1984 | Otte et al. |
| 4,439,152 A | 3/1984 | Small |
| 4,450,834 A | 5/1984 | Fischer |
| 4,481,943 A | 11/1984 | Michelson |
| 4,484,570 A | 11/1984 | Sutter et al. |
| 4,492,226 A | 1/1985 | Belykh et al. |
| 4,497,320 A | 2/1985 | Nicholson et al. |
| 4,501,269 A | 2/1985 | Bagby |
| 4,507,115 A | 3/1985 | Kambara et al. |
| RE31,865 E | 4/1985 | Roux |
| 4,530,360 A | 7/1985 | Duarte |
| 4,535,374 A | 8/1985 | Anderson et al. |
| 4,535,485 A | 8/1985 | Ashman et al. |
| 4,537,185 A | 8/1985 | Stednitz |
| 4,542,539 A | 9/1985 | Rowe, Jr. et al. |
| 4,545,374 A * | 10/1985 | Jacobson ................. 600/210 |
| 4,547,390 A | 10/1985 | Ashman et al. |
| 4,549,547 A | 10/1985 | Brighton et al. |
| 4,552,200 A | 11/1985 | Sinha et al. |
| 4,553,273 A | 11/1985 | Wu |
| 4,554,914 A | 11/1985 | Kapp et al. |
| D281,814 S | 12/1985 | Pratt et al. |
| 4,570,623 A | 2/1986 | Ellison et al. |
| 4,570,624 A | 2/1986 | Wu |
| 4,592,346 A | 6/1986 | Jurgutis |
| 4,599,086 A | 7/1986 | Doty |
| 4,600,000 A | 7/1986 | Edwards |
| 4,602,638 A | 7/1986 | Adams |
| 4,604,995 A | 8/1986 | Stephens |
| 4,608,052 A | 8/1986 | Van Kampen et al. |
| 4,611,581 A | 9/1986 | Steffee |
| 4,619,264 A | 10/1986 | Singh |
| 4,628,921 A | 12/1986 | Rousso |
| 4,634,720 A | 1/1987 | Dorman et al. |
| 4,636,217 A | 1/1987 | Ogilvie et al. |
| 4,636,526 A | 1/1987 | Dorman et al. |
| 4,645,503 A | 2/1987 | Lin et al. |
| 4,653,486 A | 3/1987 | Coker |
| 4,653,509 A | 3/1987 | Oloff et al. |
| 4,655,777 A | 4/1987 | Dunn et al. |
| 4,661,536 A | 4/1987 | Dorman et al. |
| 4,664,567 A | 5/1987 | Edwards |
| 4,665,920 A | 5/1987 | Campbell |
| 4,677,883 A | 7/1987 | Lee |
| 4,677,972 A | 7/1987 | Tornier |
| 4,693,721 A | 9/1987 | Ducheyne |
| 4,696,290 A | 9/1987 | Steffee |
| 4,698,375 A | 10/1987 | Dorman et al. |
| 4,710,075 A | 12/1987 | Davison |
| 4,713,004 A | 12/1987 | Linkow et al. |
| 4,714,469 A | 12/1987 | Kenna |
| 4,721,103 A | 1/1988 | Freedland |
| 4,736,738 A | 4/1988 | Lipovsek et al. |
| 4,232,679 A | 5/1988 | Schulman |
| 4,743,256 A | 5/1988 | Brantigan |
| 4,743,260 A | 5/1988 | Burton |
| 4,759,766 A | 7/1988 | Buettner-Janz et al. |
| 4,759,769 A | 7/1988 | Hedman et al. |
| 4,767,408 A | 8/1988 | McFarlane |
| 4,769,881 A | 9/1988 | Pedigo et al. |
| 4,772,286 A | 9/1988 | Goble et al. |
| 4,781,591 A | 11/1988 | Allen |
| 4,790,303 A | 12/1988 | Steffee |
| 4,805,602 A | 2/1989 | Puno et al. |
| 4,820,305 A | 4/1989 | Harms et al. |
| 4,830,000 A | 5/1989 | Shutt |
| 4,834,757 A | 5/1989 | Brantigan |
| 4,848,327 A | 7/1989 | Perdue |

| | | |
|---|---|---|
| 4,851,008 A | 7/1989 | Johnson |
| 4,863,476 A | 9/1989 | Shepperd |
| 4,863,477 A | 9/1989 | Monson |
| 4,865,603 A | 9/1989 | Noiles |
| 4,877,020 A | 10/1989 | Vich |
| 4,878,915 A | 11/1989 | Brantigan |
| 4,903,882 A | 2/1990 | Long |
| 4,904,260 A | 2/1990 | Ray et al. |
| 4,904,261 A | 2/1990 | Dove et al. |
| 4,911,718 A | 3/1990 | Lee et al. |
| 4,913,144 A | 4/1990 | Del Medico |
| 4,936,848 A | 6/1990 | Bagby |
| 4,943,291 A | 7/1990 | Tanguy |
| 4,955,885 A | 9/1990 | Meyers |
| 4,955,908 A | 9/1990 | Frey et al. |
| 4,957,495 A | 9/1990 | Kluger |
| 4,960,420 A | 10/1990 | Goble et al. |
| 4,961,740 A | 10/1990 | Ray et al. |
| 4,968,316 A | 11/1990 | Hergenroeder |
| 4,969,888 A | 11/1990 | Scholten et al. |
| 4,987,904 A | 1/1991 | Wilson |
| 5,015,247 A | 5/1991 | Michelson |
| 5,015,255 A | 5/1991 | Kuslich |
| 5,026,373 A | 6/1991 | Ray et al. |
| 5,030,236 A | 7/1991 | Dean |
| 5,055,104 A | 10/1991 | Ray |
| 5,059,193 A | 10/1991 | Kuslich |
| 5,059,194 A | 10/1991 | Michelson |
| 5,062,845 A | 11/1991 | Kuslich et al. |
| 5,071,437 A | 12/1991 | Steffee |
| 5,084,050 A | 1/1992 | Draenert |
| 5,102,414 A | 4/1992 | Kirsch |
| 5,105,819 A | 4/1992 | Wollschlager |
| 5,108,422 A | 4/1992 | Green et al. |
| 5,112,336 A | 5/1992 | Krevolin et al. |
| 5,116,304 A | 5/1992 | Cadwell |
| 5,122,130 A | 6/1992 | Keller |
| 5,123,926 A | 6/1992 | Pisharodi |
| 5,171,218 A | 12/1992 | Fonger et al. |
| 5,171,278 A | 12/1992 | Pisharodi |
| 5,192,327 A | 3/1993 | Brantigan |
| 5,246,458 A | 9/1993 | Graham |
| 5,258,031 A | 11/1993 | Salib et al. |
| 5,263,953 A | 11/1993 | Bagby |
| 5,269,772 A | 12/1993 | Wilk |
| 5,279,292 A | 1/1994 | Baumann |
| 5,292,252 A | 3/1994 | Nickerson et al. |
| 5,306,309 A | 4/1994 | Wagner et al. |
| 5,314,427 A | 5/1994 | Goble et al. |
| 5,324,295 A | 6/1994 | Shapiro |
| 5,330,433 A | 7/1994 | Fonger et al. |
| 5,352,229 A | 10/1994 | Goble et al. |
| 5,360,430 A | 11/1994 | Lin |
| 5,364,399 A | 11/1994 | Lowery et al. |
| 5,370,647 A | 12/1994 | Graber et al. |
| 5,370,662 A | 12/1994 | Stone et al. |
| 5,370,697 A | 12/1994 | Baumgartner |
| 5,393,036 A | 2/1995 | Sheridan |
| RE34,871 E | 3/1995 | McGuire et al. |
| 5,396,880 A | 3/1995 | Kagan et al. |
| 5,397,364 A | 3/1995 | Kozak et al. |
| 5,425,772 A | 6/1995 | Brantigan |
| 5,431,658 A | 7/1995 | Moskovich |
| 5,435,723 A | 7/1995 | O'Brien |
| 5,484,437 A | 1/1996 | Michelson |
| 5,489,307 A | 2/1996 | Kuslich et al. |
| 5,489,308 A | 2/1996 | Kuslich et al. |
| 5,505,732 A | 4/1996 | Michelson |
| 5,571,091 A | 11/1996 | Davis et al. |
| 5,571,109 A | 11/1996 | Bertagnoli |
| 5,593,409 A | 1/1997 | Michelson |
| 5,672,158 A | 9/1997 | Okada et al. |
| 6,500,180 B1 * | 12/2002 | Foley et al. ............ 606/105 |
| 6,575,899 B1 * | 6/2003 | Foley et al. ............ 600/114 |
| 6,855,148 B2 * | 2/2005 | Foley et al. ............ 606/86 R |

FOREIGN PATENT DOCUMENTS

| | | |
|---|---|---|
| DE | 24 46 039 | 4/1975 |
| DE | 3101333 A1 | 12/1981 |
| DE | 3132520 A1 | 6/1982 |
| DE | 3505567 A1 | 6/1986 |
| DE | 36 08 163 A1 | 9/1987 |
| DE | 41 04 359 A1 | 8/1992 |
| EP | 0 077 159 | 4/1983 |
| EP | 0 162 005 | 11/1985 |
| EP | 0 179 695 | 4/1986 |
| EP | 0 260 044 | 3/1988 |
| EP | 0 303 241 A2 | 2/1989 |
| EP | 0 307 241 | 3/1989 |
| EP | 0 499 465 A1 | 8/1992 |
| EP | 0 551 187 A1 | 7/1993 |
| EP | 0 577 179 A1 | 1/1994 |
| EP | 0 599 419 A2 | 6/1994 |
| ES | 283078 | 5/1985 |
| FR | 2 295 729 | 7/1976 |
| FR | 2 581 336 | 11/1986 |
| FR | 2 703 580 | 10/1994 |
| GB | 1291470 | 10/1972 |
| GB | 1492990 | 11/1977 |
| GB | 1531487 | 11/1978 |
| GB | 2076657 A | 12/1981 |
| GB | 2082754 A | 3/1982 |
| GB | 2126094 A | 3/1984 |
| GB | 2164277 A | 3/1986 |
| JP | 57-29348 | 2/1982 |
| JP | 60-31706 | 2/1985 |
| JP | 60-43984 | 3/1985 |
| JP | 61-122859 | 6/1986 |
| JP | 62-155846 | 7/1987 |
| SE | 106 101 | 7/1939 |
| SU | 1107854 | 8/1984 |
| SU | 1124960 | 11/1984 |
| SU | 1217374 | 3/1986 |
| SU | 1222254 | 4/1986 |
| WO | 84/01298 | 4/1984 |
| WO | 91/06266 | 5/1991 |
| WO | 92/14423 | 9/1992 |
| WO | 92/19146 | 11/1992 |
| WO | 93/01771 | 2/1993 |

OTHER PUBLICATIONS

Herkowitz, et al.; Principles of Bone Fusion; The Spine, Third Edition; Chapter 44, p. 1739.

Muschler, et al.; The Biology of Spinal Fusion; Spinal Fusion Science and Technique, Cotler and Cotler, pp. 9-13.

Zindrick, et al.; Lumbar Spine Fusion: Different Types and Indications; The Lumbar Spine, vol. 1, Second Edition, pp. 588-593 (1996).

Gillingham, F.J., et al.; Automatic Patient Monitoring in the Ward; Brit. J. Surg., vol. 53, No. 10, pp. 864-866 (Oct. 1966).

Maloney, A.F.J., et al.; Clinical and Pathological Observations in Fatal Head Injuries, Brit. J. Surg., vol. 56, No. 1, pp. 23-31 (Jan. 1969).

Harris, P., et al.; Spinal Deformity After Spinal Cord Injury; Paraplegia, vol. 6, No. 4, pp. 232-238 (Feb. 1969).

Gillingham, F.J., et al.; Head injuries; Proceedings of the 18th World Congress of the International College of Surgeons, Rome, pp. 68-71 (May 28-31, 1972).

Whatmore, W. J.; Sincipital Encephalomeningoceles; Brit. J. Surg., vol. 60, No. 4, pp. 261-270 (Apr. 1973).

Whatmore, W. J.; Meningioma Following Trauma; Brit. J. Surg., vol. 60, No. 6, pp. 496-498 (Jun. 1973).

Bagby, George W.; Wobbler Syndrome in Horses (the Ataxic Horse); Spokane County Medical Society Bulletin; Spring 1979.

Rathke, F.W., et al.; Surgery of the Spine; Atlas of Orthopaedic Operations, vol. 1, p. 137, W.B. Saunders Co., Philadelphia (1979).

Albrektsson, T., et al.; Osseointegrated Titanium Implants; Acta. Orthop. Scand.; vol. 52:155-170 (1981).

Raveh, J., et al.; Neue Rekonstruktionsmoglichkeiten des Unterkiefers bei knochernen Defekten nach Tumorresektionen; Der Chirurg vol. 53:459-467 (1982).

Crock, H. V.; Practice of Spinal Surgery; Springer-Verlag/Wien, New York (1983).

DeBowes, R.M., et al.; Study of Bovine . . . Steel Baskets; Transactions of the 29th Annual Meeting; Orthopaedic Research Society, vol. 8, p. 407, Mar. 8-10, 1983.

O'Neill, P., et al.; Spinal Meningoceles in Association with Neurofibromatosis; Neurosurgery, vol. 13, No. 1, pp. 82-84 (Jul. 1983).

Brandt, L., et al.; A Dowel Inserter for Anterior Cervical Interbody Fusion; J. Neurosurg. 61:793-794 (Oct. 1984).

Whatmore, W.J., et al.; The Coventry Cervical Spreader and Dowel Inserter; ACTA Neurochirurgica, vol. 70, FASC. 1-2 (1984).

Raveh, J., et al.; Use of the Titanium-coated Hollow Screw and Reconstruction Plate System in Bridging of Lower Jaw Defects; J. Oral Maxillofac Surg. 42:281-294 (1984).

Otero-Vich, Jose M.; Anterior Cervical Interbody Fusion with Threaded Cylindrical Bone; J. Neurosurg 63:750-753 (Nov. 1985).

Morscher, E., et al.; Die vordere Verplattung der Halswirbelsäule mit dem Hohlschrauben-Plattensystem aus Titanium, *Der Chirurg*, vol. 57, pp. 702-707 (1986) with English Translation.

Bagby, G.W.; Basket Implant Facilitates Spinal Fusion; Orthopedics Today, vol. 7, No. 10, (Oct. 1987).

Butts, M. K., et al.; Biomechanical Analysis of a New Method for Spinal Interbody Fixation; 1987 Symposium, American Society of Mechanical Engineers, "Advances in Bioengineering", Boston, MA (Dec. 13-18, 1987).

Crawley et al.; A Modified Cloward's Technique for Arthrodesis of the Normal Metacarpophalangeal Joint in the Horse; Veterinary Surgery, vol. 17, No. 3, pp. 117-127 (1988).

Raveh, J., et al.; Surgical Procedures for Reconstruction of the Lower Jaw Using the Titanium-Coated Hollow-Screw Reconstruction Plate System: Bridging of Defects; Otolaryngologic Clinics of North America; vol. 20, No. 3 (Aug. 1987).

Whatmore, W. J.; Proceedings of the Society of British Neurological Surgeons; Journal of Neurology, Neurosurgery, and Psychiatry, 50:1093-1100 (1987).

Goldthwaite, N., et al.; Toward Percutaneous Spine Fusion; Ch. 45; Lumbar Spine Surgery; C.V. Mosby Company, pp. 512-522 (1987).

Bagby, G.W.; Arthrodesis by the Distraction-Compression Method Using a Stainless Steel Implant; Orthopedics, vol. II, No. 6, pp. 931-934 (Jun. 1987).

Itoman, M., et al.; Banked Bone Grafting for Bone Defect Repair—Clinical Evaluation of Bone Union and Graft Incorporation; J. Jpn. Orthop. Assoc. 62:461-469 (1988).

Kane, W.J.; Direct Current Electrical Bone Growth Stimulation for Spinal Fusion; Spine, vol. 13, No. 3, pp. 363-365 (Mar. 1988).

The SpF-T Spinal Fusion Stimulator: An Efficacious Adjunct that Meets the Diverse Needs of Spine Patients; EBI Medical Systems; (Aug. 1991).

Schmitz et al.; Performance of Alloplastic Materials and Design of an Artificial Disc; The Artificial Disc, Brock, Mayer, Weigel; pp. 23-34 (1991).

The Use of Direct Current for Electrically Induced Osteogenesis; The Positive Effect of an Electronegative charge on Bone Growth; EBI Medical Systems (Feb. 1993).

Mylonas, C., et al.; Anterior Cervical Decompression and Fusion Using the Coventry Cervical Spreader and Dowel Inserter; British Journal of Neurosurgery, 7:545-549 (1993).

Fusion of the Lumbar Spine; Anterior Monosegmental Fusion L5-S1, Atlas of Spinal Operations, Thieme, pp. 270-274 (1993).

Spine Basics, Danek Group, Inc., Glossary (1993).

Lumbar Spine Surgery, Techniques & Complications; History of Lumbar Spine Surgery (1994) pp. 11-15; 27; 30; 35-45; 265-268.

Cloward, Ralph B.; Surgical Techniques for Lumbar Disc Lesions; Codman; Signature Serial 3.

Cloward, Ralph B.; Ruptured Cervical Intervertebral Discs: Removal of Disc & Osteophytes & Anterior Cervical Interbody Fusion (A.C.I.F.); Codman; Signature Series 4.

Cloward, Ralph B.; Recent Advances in Surgery of the Cervical Spine; pp. 285-293; German Society For Neurosurgery: vol. 2 Cervical Spine Operations; Excerpta Medica.

Otero-Vich, Jose M.; Anterior Cervical Interbody Fusion with Threaded Cylindrical Bone; pp. 750-753; Journal of Neurosurgery, Nov. 1985, vol. 63, No. 5.

Hutter, Charles George; Spinal Stenosis and Posterior Lumbar Interbody Fusion; pp. 103-114; Clinical Orthopaedics and Related Research; No. 193; The Association of Bone and Joint Surgeons.

Lin, Paul M.; Posterior Lumbar Interbody Fusion; pp. 114-122; Charles C. Thomas; Springfield, Illinois.

Lin, Paul M.; Lumbar Interbody Fusion: Principles and Techniques in Spine Surgery; Techniques and Complications; pp. 81, 98, 120, 146, 173, 180-184, 204, 224, 225, 231; Aspen Publishers, Inc.; 1989.

Tan, S.B.; A Modified Technique of Anterior Lumbar Fusion with Femoral Cortical Allograft; pp. 83-93; The Journal of Orthopaedic Surgical Techniques, vol. 5, No. 3, 1990.

Muller, M.E.; Manual of Internal Fixation: Techniques Recommended by the AO Group; Second Edition, Expanded and Revised; pp. 3-20, 27-41, 53-58, 71-78, 94, 311, 320; Springer-Verlag; 1979.

Hierholzer, G.; Manual on the AO/ASIF Tubular External Fixator; pp. 85-91; Springer-Verlag; 1985.

Heim, Urs; Small Fragment Set Manual: Technique Recommended by the ASIF-Group; pp. 5-7, 10, 20, 21, 30; Springer-Verlag; 1974.

Harmon, Paul H.; Anterior Excision and Vertebral Body Fusion Operation for Intervertebral Disk Syndromes of the Lower Lumbar Spine: Three- to Five-Year Results in 244 Cases; pp. 107-127; Clinical Orthopaedics and Related Research, No. 26, J.B. Lippincott Company, 1963.

Harmon, Paul H.; A Simplified Surgical Technic for Anterior Lumbar Diskectomy and Fusion; Avoidance of Complications; Anatomy of the Retroperitoneal Veins; pp. 130-143; Clinical Orthopaedics and Related Research, No. 37, J.B. Lippincott Company, 1964.

Bullough, Peter G.; Atlas of Spinal Diseases; Figure 5.7; J.B. Lippencott Company; 1988.

Butts, M.K.; Biomechanical Analysis of a New Method for Spinal lnterbody Fixation; 1987 Symposium, American Society of Mechanical Engineers, "Advance in Bioengineering", Boston, MA (Dec. 13-18, 1987).

Canale, S. Terry; Campbell's Operative Orthopaedics; vol. 3, 9th Edition; pp. 2191, 2216, 2459; Mosby, 1998.

Crock, H.V., "Anterior Lumbar Interbody Fusion Indications for its Use and Notes on Surgical Technique;" *Clinical Orthopedics*; vol. 165; pp. 157-163; May 1982.

Wilterberger, B.R., Abbott, K.H., "Dowel Intervertebral Fusion as Used in Lumbar Disc Surgery," *The Journal of Bone and Joint Surgery*, vol. 39A, cover page and pp. 284-292, and 331, 1957.

* cited by examiner

FIG. 11B
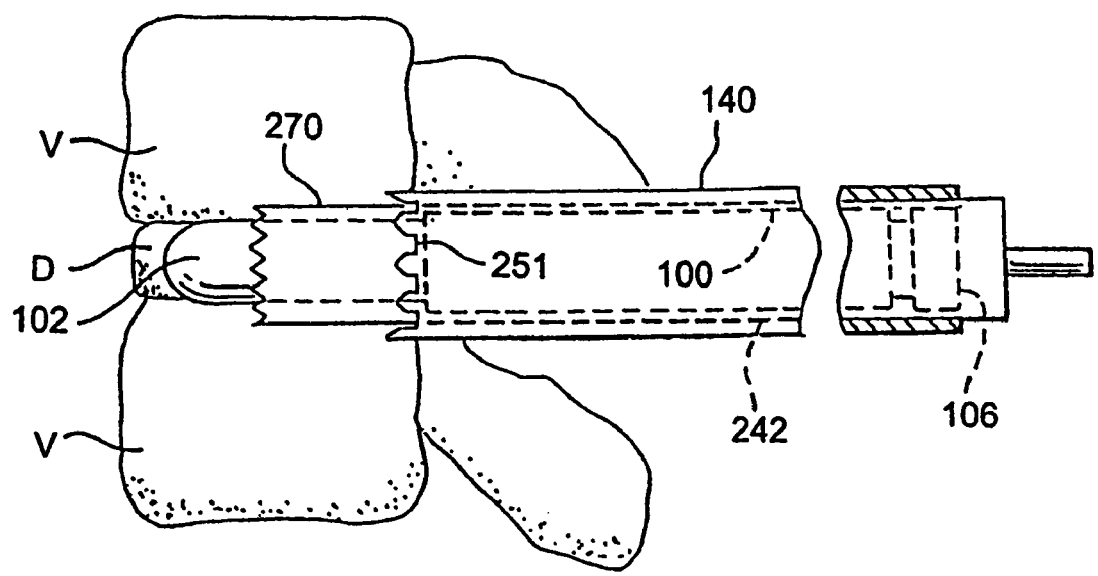
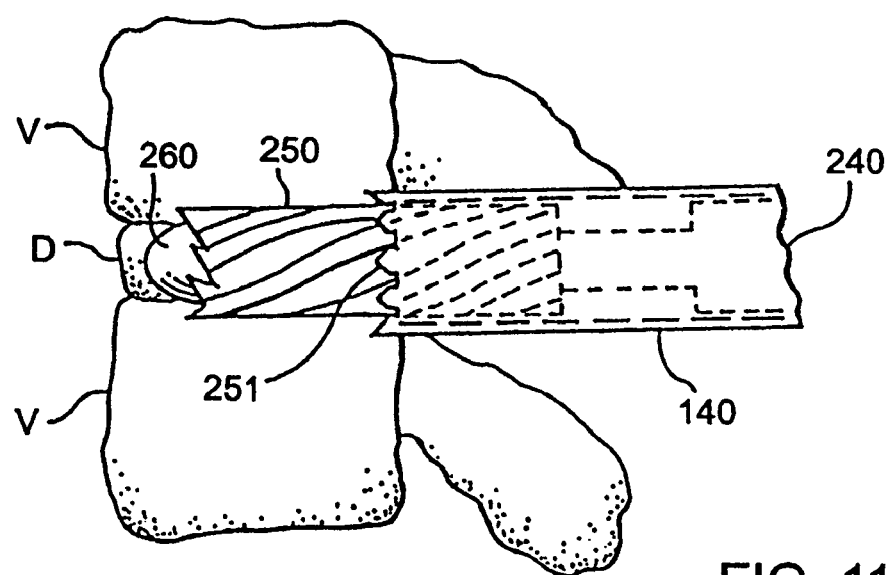
FIG. 11C

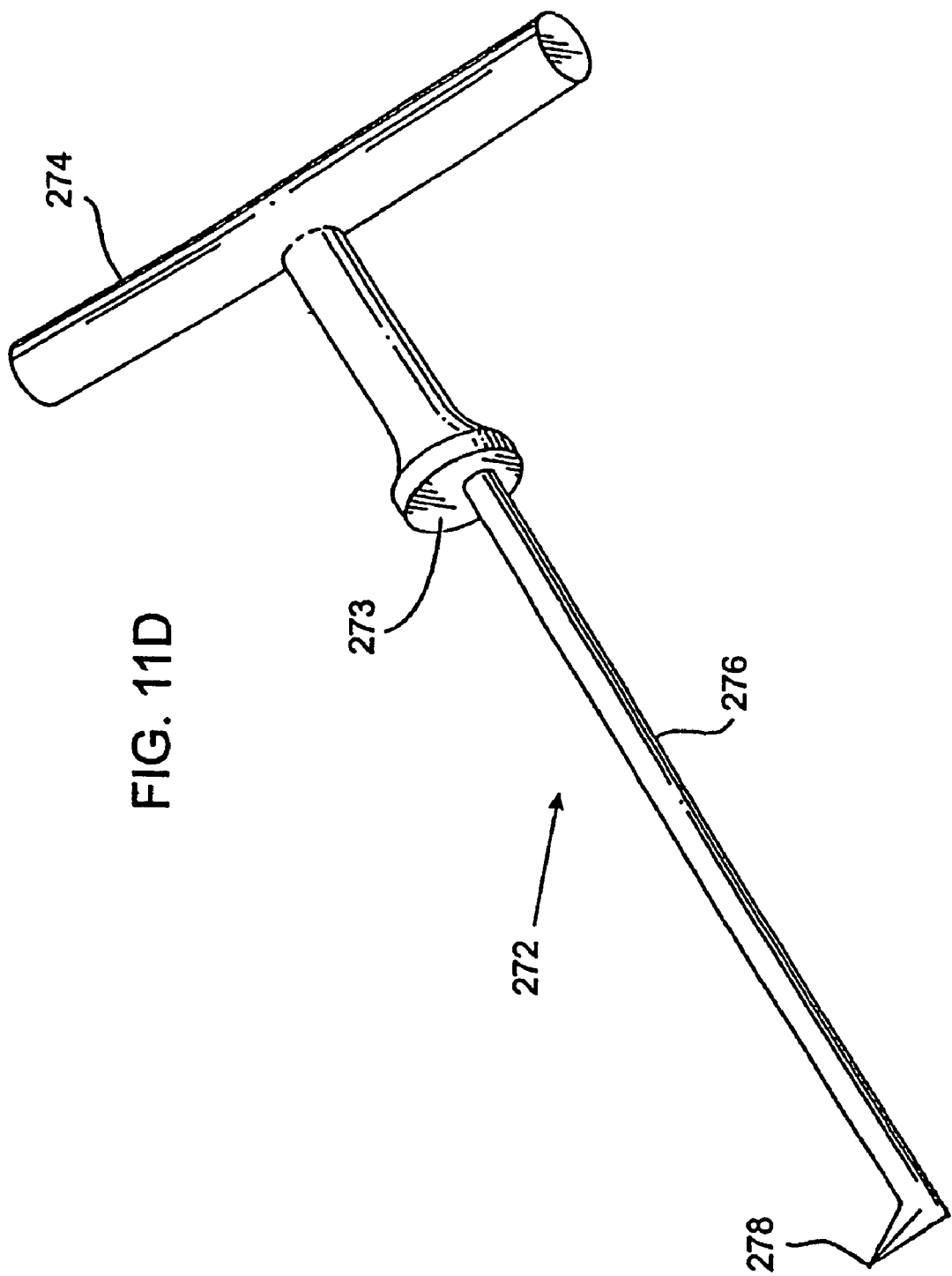

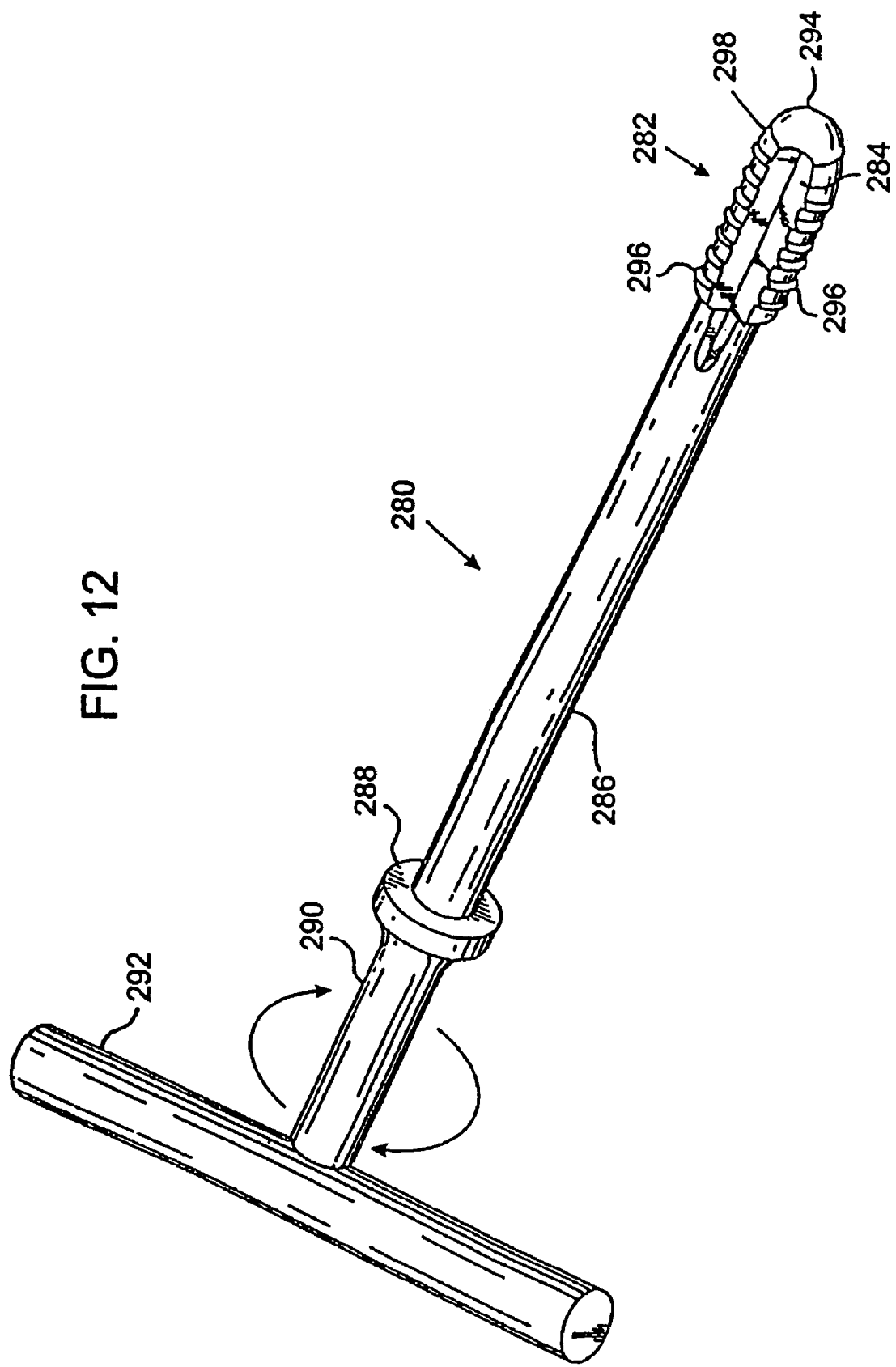

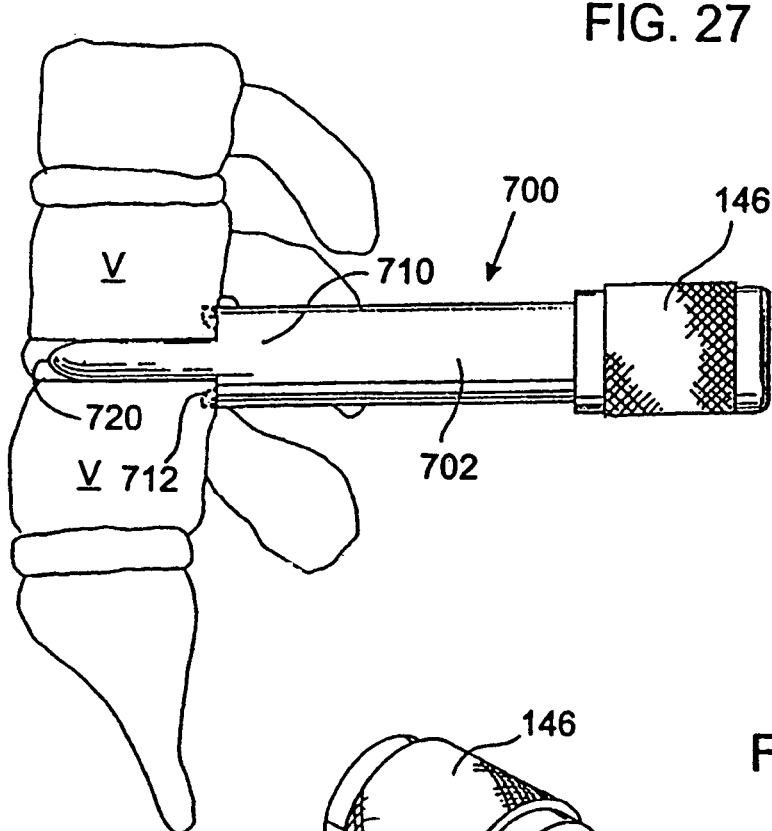
FIG. 27
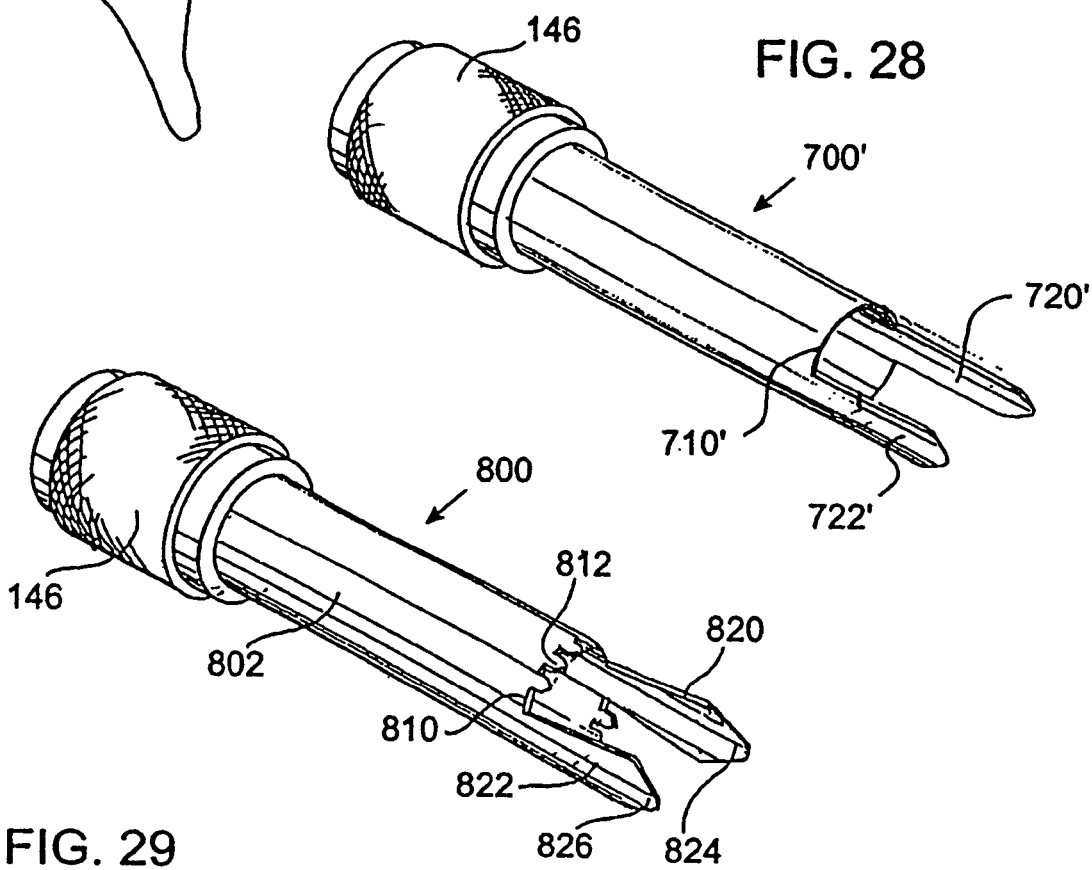
FIG. 28
FIG. 29

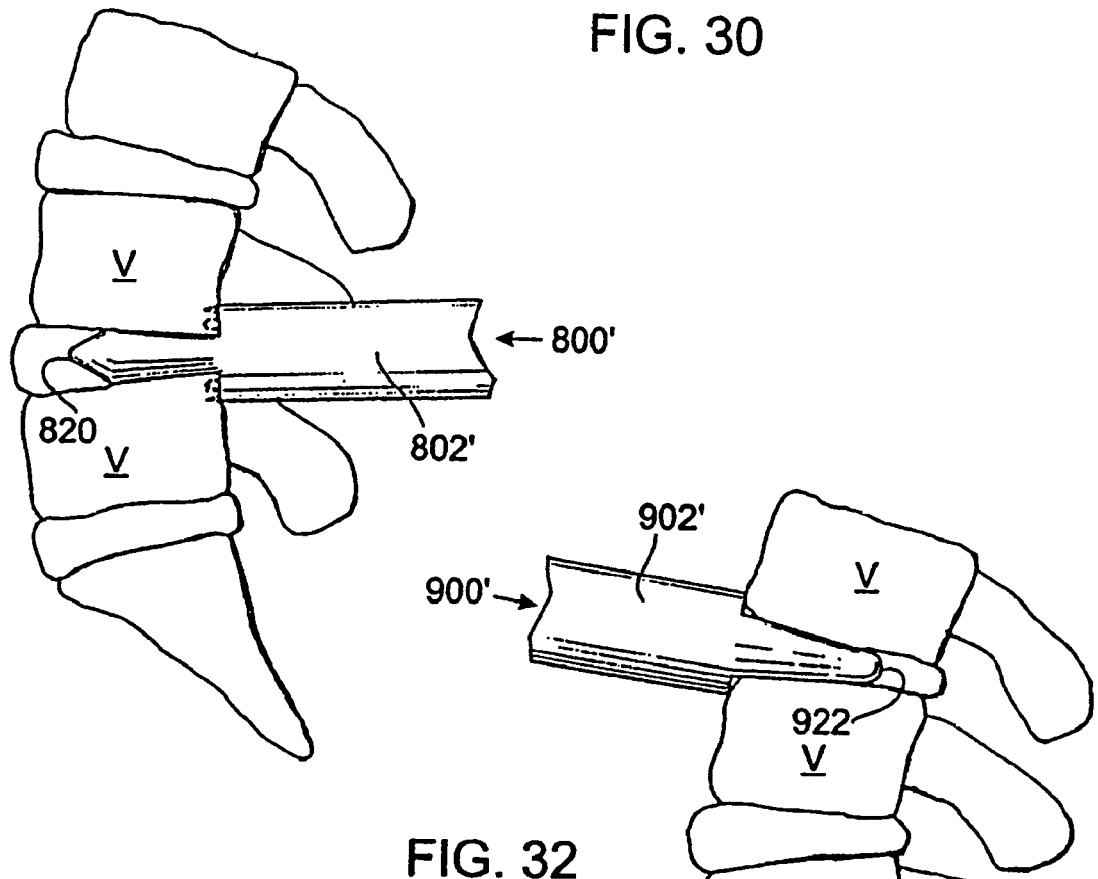
FIG. 30
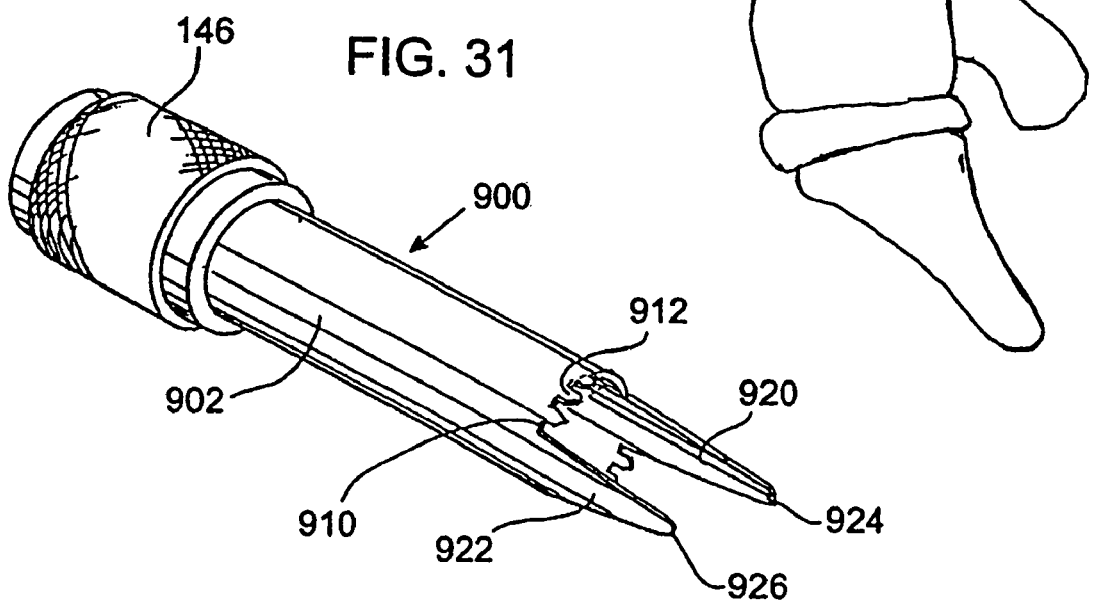
FIG. 31
FIG. 32

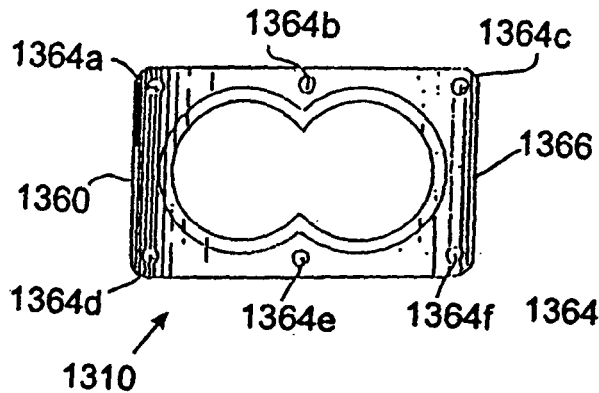
FIG. 37
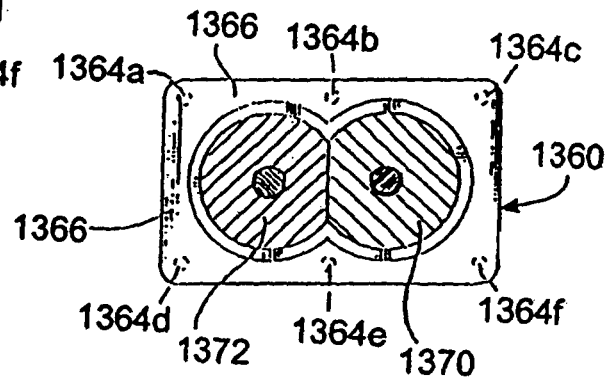
FIG. 38
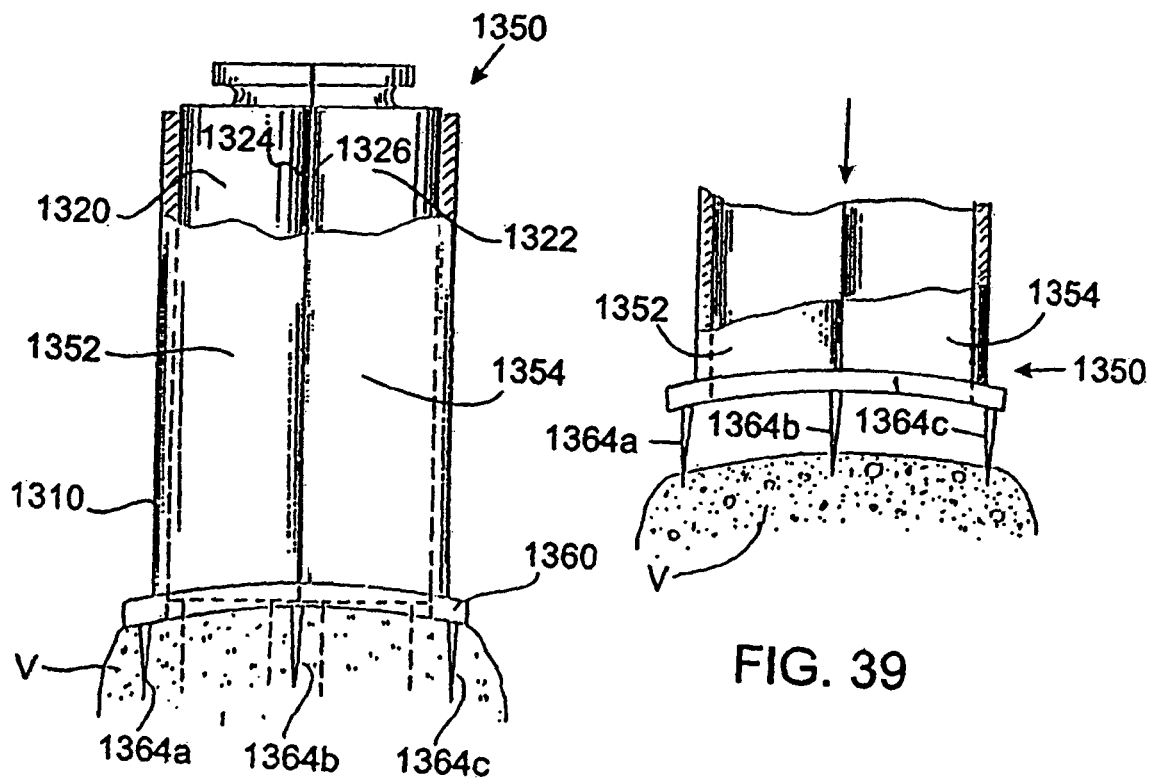
FIG. 36
FIG. 39

METHOD OF MAINTAINING DISTRACTION OF A SPINAL DISC SPACE

The present application is a divisional of U.S. application Ser. No. 10/883,382, filed Jul. 1, 2004; now U.S. Pat. No. 7,686,805 which is a divisional of U.S. application Ser. No. 09/605,001, filed Jun. 27, 2000; which is a continuation of U.S. application Ser. No. 08/396,414, filed Feb. 27, 1995, now U.S. Pat. No. 6,080,155; all of which are incorporated by reference herein.

BACKGROUND OF THE INVENTION

1. Field of the Invention

The present invention relates to artificial fusion implants to be placed into the intervertebral space left remaining after the removal of a damaged spinal disc and specifically to the apparatus for and method of, inserting the implants.

2. Description of the Prior Art

For the purpose of achieving long term stability to a segment of injured spine, a fusion (the joining together of two or more bones via a continuous bridge of incorporated bone) may be performed. Well-known to those skilled in such art is the interbody fusion wherein the disc is partially excised and bone placed within that space previously occupied by that disc material (between adjacent vertebrae) for the purpose of restoring a more normal spatial relationship, and to provide for stability; short term by mechanical support, and long term by the permanent cross bonding of bone from vertebra to vertebra. For fusion to occur within the disc space, it is necessary to prepare the vertebrae to be fused by breaking through, or cutting into, the hardened outside plates of bone (the endplates) to allow the interposed bone graft to come into direct contact with the more vascular cancellous (spongy) bone, and to thereby trick the body into attempting to heal this induced, but controlled, "fracturing" by both bone production and the healing of the grafts to both opposed vertebral surfaces such that they become one continuous segment of bone.

The purpose of the present invention is to provide an implant, and the apparatus and method of inserting the implant within the intervertebral space left after the removal of the disc material and permanently eliminate all motion at that location. To do so, the device of the present invention is space occupying within the disc interspace, rigid, self-stabilizing to resist dislodgement, stabilizing to the adjacent spinal vertebrae to eliminate local motion, and able to intrinsically participate in a vertebra to vertebra bony fusion so as to assure the permanency of the result.

At present, following the removal of a damaged disc, either bone or nothing is placed into the remaining space. Placing nothing into this space allows the space to collapse which may result in damage to the nerves; or the space may fill with scar tissue and eventually lead to a reherniation. The use of bone to fill the space is less than optimal in that bone obtained from the patient requires additional surgery and is of limited availability in its most useful form, and if obtained elsewhere, lacks living bone cells, carries a significant risk of infection, and is also limited in supply as it is usually obtained from accident victims. Furthermore, regardless of the source of the bone, it is only marginal structurally and lacks a means to either stabilize itself against dislodgement, or to stabilize the adjacent vertebrae.

a. Prior Art Implants

There have been an extensive number of attempts to develop an acceptable disc prosthesis (an artificial disc). Such devices by design would be used to replace a damaged disc and seek to restore the height of the interspace and to restore the normal motion of that spinal joint. No such device has been found that is medically acceptable. This group of prosthetic or artificial disc replacements, seeking to preserve spinal motion and so are different from the present invention, would include:

U.S. Pat. No. 3,867,728 to STUBSTAD—describing a flexible disc implant.

U.S. Pat. No. 4,349,921 to KUNTZ—describing a flexible disc replacement with file-like surface projections to discourage device dislocation.

U.S. Pat. No. 4,309,777 to PATIL—describing a motion preserving implant with spiked outer surfaces to resist dislocation and containing a series of springs to urge the vertebrae away from each other.

U.S. Pat. No. 3,875,595 to FRONING—describing a motion preserving bladder-like disc replacement with two opposed stud-like projections to resist dislocation.

U.S. Pat. No. 2,372,622 to FASSIO (France)—describing a motion preserving implant comprising complimentary opposed convex and concave surfaces.

In summary, these devices resemble the present invention only in that they are placed within the intervertebral space following the removal of a damaged disc. In that they seek to preserve spinal motion, they are diametrically different from the present invention which seeks to permanently eliminate all motion at that spinal segment.

A second related area of prior art includes those devices utilized to replace essentially wholly removed vertebrae. Such removal is generally necessitated by extensive vertebral fractures, or tumors, and is not associated with the treatment of disc disease. While the present invention is to be placed within the disc space, these other vertebral devices cannot be placed within the disc space as at least one vertebra has already been removed such that there no longer remains a "disc space". Furthermore, these devices are limited in that they seek to perform as temporary structural members mechanically replacing the removed vertebrae (not a removed disc), and do not intrinsically participate in supplying osteogenic material to achieve cross vertebrae bony fusion. Therefore, unlike the present invention which provides for a source of osteogenesis, use of this group of devices must be accompanied by a further surgery consisting of a bone fusion procedure utilizing conventional technique. This group consisting of vertebral struts rather than disc replacements would include the following:

U.S. Pat. No. 4,553,273 to WU—describing a turnbuckle-like vertebral strut.

U.S. Pat. No. 4,401,112 to REZAIAN—describing a turnbuckle-like vertebral strut with the addition of a long stabilizing staple that spans the missing vertebral body.

U.S. Pat. No. 4,554,914 to KAPP—describing a large distractible spike that elongates with a screw mechanism to span the gap left by the removal of an entire vertebra and to serve as an anchor for acrylic cement which is then used to replace the missing bone (vertebrae).

U.S. Pat. No. 4,636,217 to OGILVIE—describing a vertebral strut mechanism that can be implanted after at least one vertebrae has been removed and consists of a mechanism for causing the engagement of screws into the vertebrae above and the vertebrae below the one removed.

In summary, this second group of devices differs from the present invention in that they are vertebral replacements struts, do not intrinsically participate in the bony fusion, can only be inserted in the limited circumstances where an entire vertebra has been removed from the anterior approach, and are not designed for, or intended to be used for the treatment of disc disease.

A third area of prior art related to the present invention includes all devices designed to be applied to one of the surfaces of the spine. Such devices include all types of plates, struts, and rods which are attached by hooks, wires and screws. These devices differ significantly from the present invention in that they are not inserted within the disc space and furthermore do not intrinsically participate in supplying osteogenic material for the fusion.

Therefore, where permanent spinal immobilization is desired, an additional surgery, consisting of a spinal fusion performed by conventional means or the use of supplemental methylmethacrylate cement is required. Such devices applied to the spine, but not within the disc space, would include the following:

U.S. Pat. No. 4,604,995 to STEPHENS—describing a "U" shaped metal rod attached to the posterior elements of the spine with wires to stabilize the spine over a large number of segments.

U.S. Pat. No. 2,677,369 to KNOWLES—describing a metal column device to be placed posteriorly along the lumbar spine to be held in position by its shape alone and to block pressure across the posterior portions of the spinal column by locking the spine in full flexion thereby shifting the maximum weight back onto the patient's own disc.

Other devices are simply variations on the use of rods (e.g. Harrington, Luque, Cotrel-Dubosset, Zielke), wires or cables (Dwyer), plates and screws (Steffee), or struts (Dunn, Knowles)

In summary, none of these devices are designed to be nor can be used within the disc space. Moreover, these devices do not replace a damaged disc, and do not intrinsically participate in the generation of a bony fusion.

Another area of related prior art to be considered is that of devices designed to be placed within the vertebral interspace following the removal of a damaged disc, and seeking to eliminate further motion at that location.

Such a device is contained in U.S. Pat. No. 4,501,269 issued to BAGBY which describes an implantable device and limited instrumentation. The method employed is as follows: a hole is bored transversely across the joint and a hollow metal basket of larger diameter than the hole is then pounded into the hole and then the hollow metal basket is filled with the bone debris generated by the drilling.

While the present invention (device, instrumentation, and method) may appear to bear some superficial resemblance to the BAGBY invention, it is minimal, while the differences are many fold and highly significant. These differences include the following:

1. Safety—The present invention provides for a system of completely guarded instrumentation so that all contiguous vital structures (e.g. large blood vessels, neural structures) are absolutely protected. The instrumentation of the present invention also makes overpenetration by the drill impossible. Such overpenetration in the cervical spine, for example, would result in the total paralysis or death of the patient. In the thoracic spine, the result would be complete paraplegia. In the lumbar spine, the result would be paraplegia or a life-threatening perforation of the aorta, vena cava, or iliac vessels.

The present invention is atraumatically screwed into place while the BAGBY device, in contradistinction, is pounded into position. BAGBY describes that its implant is significantly larger in size than the hole drilled and must be pounded in. This is extremely dangerous and the pounding occurs directly over the spinal cord which is precariously vulnerable to percussive injury. Furthermore, while it is possible, for example in the lumbar spine, to insert the present invention away from the spinal cord and nerves, the BAGBY device must always be pounded directly towards the spinal cord.

Furthermore, since the BAGBY device is pounded into a smooth hole under great resistance, and lacking any specific design features to secure it, the device is highly susceptible to forceful ejection which would result in great danger to the patient and clinical failure. The present invention, in contradistinction, is securely screwed into place, and possesses highly specialized locking threads to make accidental dislodgement impossible. Because of the proximity of the spinal cord, spinal nerves, and blood vessels, any implant dislodgement as might occur with the BAGBY device might have catastrophic consequences.

2. Broad applicability—The BAGBY device can only be inserted from the front of the vertebral column, however, in contrast, the present invention can be utilized in the cervical, thoracic, and lumbar spine, and can be inserted from behind (posteriorly) in the lumbar spine. This is of great importance in that the purpose of these devices is in the treatment of disc disease and probably greater than 99 percent of all lumbar operations for the treatment of disc disease are performed from behind where the present invention can easily be utilized, but the BAGBY device, as per BAGBY'S description, cannot.

3. Disc removal—The BAGBY invention requires the complete removal of the disc prior to the drilling step, whereas the present invention eliminates the laborious separate process of disc removal and efficiently removes the disc and prepares the vertebral end plates in a single step.

4. Time required—The present invention saves time over the BAGBY invention since time is not wasted laboring to remove the disc prior to initiating the fusion. Also, with the present invention the procedure is performed through a system of guarded instrumentation, time is not wasted constantly placing and replacing various soft tissue retractors throughout the procedure.

5. Implant stability—Dislodgement of the implant would be a major source of device failure (an unsuccessful clinical result), and might result in patient paralysis or even death. As discussed, the BAGBY device lacks any specific means of achieving stability and since it is pounded in against resistance to achieve vertebral distraction, and is susceptible to forceful dislodgement by the tendency of the two distracted vertebrae, to return to their original positions squeezing out the device. The present invention, however, is screwed into place. As there is no unscrewing force present between the vertebrae, compression alone cannot dislodge the implant. The implant is inherently stable by its design. Furthermore, the threads of the present invention are highly specialized in that they are periodically interrupted so that the tail ends of each of the tabs so formed are blunted and twisted so as to resist accidental unscrewing. The removal of an implant with such "locking threads" requires the use of a special extractor included within the instrumentation. The stability of the present invention is still further enhanced, again in contradistinction to the BAGBY device, by the presence of a "bone ingrowth" surface texturing, which both increases the friction of the fit and allows for the direct growth of the vertebral bone into the casing of the implant itself.

6. Spinal stability—The present invention is not only self-stabilizing, it also provides stability to the adjacent vertebrae in at least three ways that the BAGBY device cannot. First, the BAGBY device is placed transversely across the joint in the center, leaving both vertebrae free to rock back and forth over this round barrel shaped axis, much like a board over a barrel, being used for a seesaw.

Secondly, as the BAGBY device lacks any specific design features to resist sliding, it may actually behave as a third body allowing the translation of the vertebrae relative to the device and to each other.

Thirdly, any device can only provide stability if it remains properly, seated. The present invention is inherently stable, and therefore assures that it will stabilize the adjacent vertebrae, rather than, as with the BAGBY, the instability of the spine to be treated may cause a dislocation of the BAGBY implant, with further loss of spinal stability.

7. The collapse of the interspace—While both the present invention and the BAGBY device can be fabricated to withstand the compression forces within the interspace, the interspace may nevertheless collapse under the superincumbent body weight as the implant settles into the vertebral bone. This is related to the load per unit area. Again the present invention is superior to the BAGBY device in at least four ways.

First, the present invention offers considerably greater surface area to distribute the load. Secondly, while the BAGBY device is placed centrally, the present device is placed bilaterally where the bone tends to be more cortical and much stronger out towards the rim. Thirdly, the present invention supports the load achieving an "I" beam effect, whereas the BAGBY implant does not. Fourthly, it is not pressure alone that causes the collapse of the bone adjacent to the implant, but also bony erosion that is caused by the motion under pressure of the implant against the bone. As discussed in item 6 above, the present invention alone is highly resistant to such motion, again diminishing the likelihood of erosion and interspace collapse.

8. Bone ingrowth surface texturing—The present invention has a surface treatment of known and conventional technology to induce the growth of bone from the vertebrae directly into the casing material of the implant itself. The BAGBY device has no similar feature.

9. Fusion mass—The BAGBY invention calls for removing the disc and then drilling a hole between the adjacent vertebrae. The bony debris so generated is then put into the device. The present invention takes a core of pure bone producing marrow from the iliac crest, and then by use of a special press, forcibly injects the implant device with an extremely dense compressed core of that osteogenic material until the material itself virtually extrudes from every cell of the implant.

10. The probability of achieving fusion—The fusion rate within the spine is known to be related directly to the amount of exposed vascular bone bed area, the quality and quantity of the fusion mass available, and the extent of the stabilization obtained with all other factors being half constant. It would then be anticipated, that the fusion rate would be superior with the present invention as compared to the BAGBY device, because of optimal implant stability (#5), optimal spinal stability (#6), bone ingrowth surface treatment (#8), superior fusion mass (#9), and the greater exposed vertebral bony surface area (#7).

The last area of prior art possibly related to the present invention and therefore, to be considered related to "bony ingrowth", are patents that either describe methods of producing materials and or materials or devices to achieve the same. Such patents would include:

U.S. Pat. No. 4,636,526 (DORMAN), U.S. Pat. No. 4,634,720 (DORMAN), U.S. Pat. No. 4,542,539 (ROWE), U.S. Pat. No. 4,405,319 (COSENTINO), U.S. Pat. No. 4,439,152 (SMALL), U.S. Pat. No. 4,168,326 (BROEMER), U.S. Pat. No. 4,535,485 (ASHMAN), U.S. Pat. No. 3,987,499 (SCHARBACH), U.S. Pat. No. 3,605,123 (HAHN), U.S. Pat. No. 4,655,777 (DUNN), U.S. Pat. No. 4,645,503 (LIN), U.S. Pat. No. 4,547,390 (ASHMAN), U.S. Pat. No. 4,608,052 (VAN KAMPEN), U.S. Pat. No. 4,698,375 (DORMAN), U.S. Pat. No. 4,661,536 (DORMAN), U.S. Pat. No. 3,952,334 (BOKROS), U.S. Pat. No. 3,905,047 (LONG), U.S. Pat. No. 4,693,721 (DUCHEYNE), U.S. Pat. No. 4,070,514 (ENTHERLY).

However, while the implant of the present invention would utilize bone ingrowth technology, it would do so with conventional technology.

b. Prior Art Instrumentations and Methods

The following is a history of the prior art apparatus and methods of inserting spinal implants:

In 1956, Ralph Cloward developed a method and instruments which he later described for preparing the anterior aspect (front) of the cervical spine, and then fusing it. Cloward surgically removed the disc to be fused across and then placed a rigid drill guide with a large foot plate and prongs down over an aligner rod and embedded said prongs into the adjacent vertebrae to maintain the alignment so as to facilitate the reaming out of the bone adjacent the disc spaces. As the large foot plate sat against the front of the spine, it also served as a fixed reference point to control the depth of drilling. The reaming left two opposed resected arcs, one each, from the opposed vertebral surfaces. The tubular drill guide, which was placed only preliminary to the drilling, was thereafter completely removed. A cylindrical bony dowel, significantly larger in diameter than the hole formed, was then pounded into the hole already drilled. Cloward's method of instrumentation was designed for, and limited to, use on the anterior aspect and in the region of the cervical spine only. The hole was midline, which would preclude its use posteriorly where the spinal cord would be in the way.

As the bone graft to be inserted in Cloward's method was necessarily larger in diameter than the hole drilled, the graft could not be inserted through the drill guide. This mandated the removal of the drill guide and left the graft insertion phase completely unprotected. Thus Cloward's method and instrumentation was inappropriate for posterior application.

In addition, the failure to provide continuous protection to the delicate neural structures from the instruments, as well as the bony and cartilaginous debris generated during the procedure, made Cloward's method inappropriate for posterior application. Also, the drill guide described by Cloward could not be placed posteriorly within the spinal canal, as the foot plate would crush the nerves. Modifying Cloward's drill guide by removing the foot plate completely, would still leave the instrument unworkable as it would then lack stability, and would not be controllable for depth of seating.

Nevertheless, Wilterberger, (Wilterberger, B. R., Abbott, K. H., "Dowel Intervertebral Fusion as Used in Lumbar Disc Surgery," *The Journal of Bone and Joint Surgery*, Volume 39A, pg. 234-292, 1957) described the unprotected drilling of a hole from the posterior into the lumbar spine between the nerve roots and across the disc space, and then inserting a stack of button-like dowels into that space. While Wilterberger had taken the Cloward concept of circular drilling and dowel fusion and applied it to the lumbar spine from a posterior approach, he had not provided for an improved method, nor had he advanced the instrumentation so as to make that procedure sufficiently safe, and it rapidly fell into disrepute.

Crock (Crock, H. V., "Anterior Lumbar Interbody Fusion—Indications for its Use and notes on Surgical Technique," *Clinical Orthopedics*, Volume 165, pg. 157-163, 1981) described his technique and instrumentation for Anterior Interbody Fusion of the lumbar spine, wherein he drilled two large holes side by side across the disc space from anterior to posterior essentially unprotected and then pounded in two at least partially cylindrical grafts larger than the holes prepared.

A review of the prior art is instructive as to a number of significant deficiencies in regard to the method and instrumentation for the performance of Interbody Spinal Fusion utilizing drilling to prepare the endplates.

As the great majority of spinal surgery is performed in the lumbar spine and from posteriorly, a review of the prior art reveals a number of deficiencies in regard to the spine in general, and to the posterior approach to the lumbar spine specifically. These deficiencies include the:

1. Failure to protect the surrounding tissues throughout the procedure, specifically, prior to drilling and until after the insertion of the graft;

2. Failure to contain the debris, bony and cartilaginous, generated during the procedure;

3. Failure to optimize the contact of the cylindrical drill hole and bone graft, the mismatch in their diameters resulting in incongruence of fit;

4. Failure to determine the optimal drill size prior to drilling;

5. Failure to determine the optimal amount of distraction prior to drilling;

6. Inability to optimize the amount of distraction so as to restore the normal spatial relationships between adjacent vertebrae;

7. Inability to create sufficient working space within the spinal canal (between the nerve roots and the dural sac) to make the procedure safe;

8. Absent a foot plate on the drill guide, as necessitated by the close tolerances posteriorly, the inability to reliably insure that the drilling is parallel to the vertebral endplates;

9. The inability to insure equal bone removal from the opposed vertebral surfaces; and 10. The inability to determine within the spinal canal, the proper side by side positioning for dual drill holes.

SUMMARY OF THE INVENTION

The present invention comprises a series of artificial implants, the purpose of which is to participate in, and directly cause bone fusion across an intervertebral space following the excision of a damaged disc. Such implants are structurally load bearing devices, stronger than bone, capable of withstanding the substantial forces generated within the spinal interspace. The devices of the present invention have a plurality of macro sized cells and openings, which can be loaded with fusion promoting materials, such as autogenous bone, for the purpose of materially influencing the adjacent vertebrae to perform a bony bond to the implants and to each other. The implant casing may be surface textured or otherwise treated by any of a number of known technologies to achieve a "bone ingrowth surface" to further enhance the stability of the implant and to expedite the fusion.

The devices of the present invention are configured and designed so as to promote their own stability within the vertebral interspace and to resist being dislodged, and furthermore, to stabilize the adjacent spinal segments.

The apparatus and method of the present invention for preparing the vertebrae for insertion of the implant allows for the rapid and safe removal of the disc, preparation of the vertebrae, performance of the fusion, and internal stabilization of the spinal segment.

The present invention is a method for Interbody Spinal Fusion utilizing novel instrumentation, whereby a protective tubular member, or paired tubular members are placed prior to the drilling part of the procedure and may be left in place until the implant is fully seated.

By way of example, regarding the posterior approach to the lumbar spine, two distractors are used to separate two adjacent vertebrae to a preferred distance. A hollow Outer Sleeve having teeth at one end is driven into the adjacent vertebrae on one side to hold the vertebrae in position. When the distractor is removed, a diameter reducing hollow Inner Sleeve is introduced into the Outer Sleeve. A drill having a drill stop is passed through the hollow Inner Sleeve to drill a hole to a desired depth. An implant is then inserted into the hole. The method is repeated on the other side of the disc.

The present invention provides apparatus and method for inserting spinal implants from the anterior, posterior, and lateral aspect of the spine. The instrumentation and method of the present invention provides a distractor instrument configured to restore and maintain the normal angular relationship of the vertebrae of the spine, known as lordosis or kyphosis, prior to the completion of the fusion procedure. The present invention also provides an extended outer sleeve that is a combination distractor and outer sleeve used for performing the surgical procedure of the present invention. The combination distractor and outer sleeve may also be configured to maintain the normal angular relationship of the vertebrae during the surgical procedure. The present invention further discloses a combination distractor outer sleeve that may be used to perform the surgical procedure of the present invention from the lateral aspect of the spinal column that protects the great vessels and neural structures from being damaged during the surgical procedure.

In summary then, the present invention, instrumentation, and method, provides for the performance of a total nuclear discectomy, an interbody fusion, a rigid internal fixation of the spine as a single integrated surgical procedure.

Discussion of the Instrumentation

The apparatus and method of the present invention provide the following advantages:

1. The present invention is safer by providing protection of the surrounding tissues. An Outer Sleeve places all of the delicate soft tissue structures, nerves, blood vessels, and organs outside of the path of the various sharp surgical instruments and the implant. Further, it is an improvement upon hand held retractors in that it occupies the least possible amount of area, avoids the stretching associated with manual retraction, provides for the retraction and shielding of the surrounding tissues in all directions circumferentially and simultaneously, and it does so exclusively with smooth, curved surfaces.

2. The present invention is safer by providing protection against the danger of instrument or implant overpenetration.

3. The present invention is safer as the surgical site and wound are protected from the debris generated during the procedure.

4. The present invention is safer because the method provides for absolute protection to the soft tissues directly and from indirect injury by overpenetration. It makes safe the use of power instrumentation which is both more effective and efficient.

5. The present invention maintains the vertebrae to be fused rigid throughout the procedure.

6. The present invention holds the vertebrae to be fused aligned throughout the procedure.

7. The present invention holds the vertebrae to be fused distracted throughout the procedure.

8. The present invention assures that all instruments introduced through the Outer Sleeve are coaxial and equally centered through the disc space and parallel the endplates.

9. The present invention facilitates the implant insertion by countering the high compressive forces tending to collapse the interspace, which if left unchecked would resist the introduction and advancement of the implant and make stripping more likely.

10. The present invention extends the range and use of the procedure and similarly the interbody spinal implant itself by making the procedure safe throughout the spine.

11. The present invention increases the ability to use a specifically sized implant.

12. In the present invention the end of all the penetrating instrumentation is blunt faced.

13. In the present invention all of the instruments have been stopped at a predetermined depth to avoid overpenetration.

14. The design of the Outer Sleeve in the present invention conforms to the spacial limitations of the specific surgical site.

15. The design and use of a second or Inner Sleeve in the present invention allows for the difference in size between the inside diameter of the Outer Sleeve, and the outside diameter of the drill itself. This difference being necessary to accommodate the sum of the distraction to be produced, and the depth of the circumferential threading present of the implant.

16. In the present invention a specially designed drill bit with a central shaft recess allows for the safe collection of the drilling products, which can then be removed without disturbing the Outer Sleeve by removing the drill bit and Inner Sleeve as a single unit.

17. In the present invention a specially designed trephine is provided for preparing cylindrical holes across the disc space and into two adjacent vertebrae, and for harvesting of the bone graft by removing a core of bone slightly smaller in diameter than the internal diameter of the implant cavity itself, however of a greater length.

18. In the present invention a specially designed press for forcefully compressing and injecting the long core of autogenous bone into the implant, such that it extrudes through the implant itself.

19. In the present invention a specially designed driver extractor, which attaches to the implant and allows the implant to be either inserted or removed without itself dissociating from the implant, except by the deliberate disengagement of the operator.

20. In the present invention predistraction increases the working space.

21. The Distractor in the present invention is self-orienting acting as a directional finder.

22. The Distractor in the present invention is self-centralizing between the opposed vertebral surfaces acting as a centering post for the subsequent bone removal.

23. In the present invention predistraction assures the equal removal of bone from the adjacent vertebral surfaces.

24. In the present invention predistraction assures the exact congruence between the hole drilled and the device.

25. In the present invention predistraction assures that the drilling is parallel to the vertebral endplates.

26. In the present invention predistraction allows for the determination of the optimal distraction prior to drilling.

27. In the present invention predistraction allows for the verification of the correct prosthesis size prior to drilling.

28. In the present invention predistraction facilitates device insertion by relieving the compressive loads across the interspace which would resist implantation.

29. In the present invention predistraction decreases the likelihood of stripping the bone during insertion.

30. In the present invention predistraction provides for the side by side positioning, spacing, and parallelism required prior to the irrevocable event of drilling.

31. In the present invention predistraction provides for the rigid stabilization of the vertebrae opposed to the disc space throughout the surgical procedure.

32. In the present invention predistraction provides for an implant easier to insert as the compressive loads of the opposed vertebrae are held in check so that the device itself need not drive the vertebrae apart to be inserted.

33. In the present invention predistraction allows for the insertion of a more effective implant as more of the implant can be dedicated to its intended purpose and be full diameter, whereas without the benefit of predistraction and the ability to maintain the same, a significant portion of the forward end of the implant would need to be dedicated to the purpose of separating the opposing vertebrae.

34. The present invention allows for the use of an implant with a sharper thread or surface projections as there is no danger to the surrounding tissues.

35. The present invention allows for the implant to be fully preloaded as provided to the surgeon, or for the surgeon to load it with the material of his choice at the time of surgery.

36. The present invention allows for the loading of a spinal implant outside of the spinal canal and prior to implantation.

37. The present invention provides for Distractors for the restoration of the physiologic amount of lordosis/kyphosis at any given level of the spine.

38. The Distractors of the present invention provide for the restoration of sagittal spinal alignment and the segmental correction of scoliosis.

39. The present invention provides Extended Outer Sleeves which are a combined Distractor and Outer Sleeve for the three dimensional segmental restoration of spinal alignment.

OBJECTS OF THE PRESENT INVENTION

It is an object of the present invention to provide an improved method of performing a discectomy, a fusion, and an internal stabilization of the spine, and specifically, all three of the above simultaneously and as a single procedure.

It is another object of the present invention to provide an improved method of performing a discectomy, a fusion, and an internal stabilization of the spine, which is both quicker and safer than is possible by previous methods.

It is another object of the present invention to provide an improved method of performing a discectomy, a fusion and an internal stabilization of the spine, to provide for improved surgical spinal implants.

It is another object of the present invention to provide an improved method of performing a discectomy, a fusion, and an internal stabilization of the spine, which provides for an improved system of surgical instrumentation to facilitate the performance of the combined discectomy, fusion, and internal spinal stabilization.

It is another object of the present invention to provide an improved method of performing a discectomy, a fusion, and an internal stabilization of the spine.

It is an object of the present invention to provide instrumentation and a method of spinal interbody arthrodesis that is faster, safer, and more efficacious than prior methods, and can effectively be performed in the cervical, thoracic, and lumbar spine anteriorly, as well as in the lower lumbar spine posteriorly.

It is a further object of the present invention to provide a means for inserting a spinal implant between adjacent vertebrae while maintaining their optimal spacing, positioning, and alignment.

It is another object of the present invention to provide instrumentation for restoring and maintaining the normal angular relationship of adjacent vertebrae of the spine, be it lordosis, kyphosis, and/or the segmental correction of scoliosis, achieving a total nuclear discectomy, an interbody spinal fusion, and a rigid internal fixation of a segment of the spine as a single integrated surgical procedure for spinal fusion.

It is another object of the present invention to provide for an instrument that is a combination Outer Sleeve and Distractor for inserting a spinal implant between adjacent vertebrae while effecting and maintaining the optimal, spacing, positioning, and alignment of the vertebrae.

It is another object of the present invention to provide a Distractor capable of restoring and maintaining the normal angular relationship between adjacent vertebrae that may be inserted within the disc space between two adjacent vertebrae.

It is yet another object of the present invention to provide instrumentation and a method of spinal interbody arthrodesis that is faster, safer, and more efficacious than prior methods, and can effectively be performed in the cervical, thoracic, and lumbar spine.

These and other objects of the present invention will be apparent from review of the following specification and the accompanying drawings.

BRIEF DESCRIPTION OF THE DRAWINGS

FIG. 11B is a side elevational view of preparation of the intervertebral space by the alternative "Trephine Method" showing the Distractor, Trephine, Inner Sleeve, and Outer Sleeve in place.

FIG. 11C is a side elevational view as in FIG. 11A, but showing the use of an alternative drilling conformation wherein the extended proximal portion of the Drill is both distracting and self-centering.

FIG. 11D is a side perspective view of an instrument for removing arcs of bone from vertebrae following drilling.

FIG. 12 is a side perspective view of the surgical Tap.

FIG. 27 is a side elevational view of the Extended Outer Sleeve of FIG. 26 shown inserted between adjacent vertebrae of the spine.

FIG. 28 is an alternative embodiment of the Extended Outer Sleeve of FIG. 26 shown without an engaging means for engaging adjacent vertebrae.

FIG. 29 is a perspective side view of a Posterior Lordotic Extended Outer Sleeve of the present invention having uneven extended members for restoring and maintaining lordosis of the spine and engagement means for engaging the vertebrae.

FIG. 30 is a side elevational view of a portion of the Posterior Lordotic Extended Outer Sleeve of FIG. 29 inserted between adjacent vertebrae from the posterior aspect of the spine to restore and maintain lordosis.

FIG. 31 is a perspective side view of an Anterior Lordotic Extended Outer Sleeve of the present invention having extended members for restoring and maintaining lordosis of the spine from the anterior aspect of the spine.

FIG. 32 is a side elevational side view of an alternative embodiment of the Anterior Lordotic Extended Outer Sleeve of FIG. 31 absent the engagement means for engaging the vertebrae, inserted between adjacent vertebrae from the anterior aspect of the spine.

FIG. 36 is an elevational front view of the apparatus of the present invention for use in installing interbody spinal implants having one or more flat sides, shown placed over two Long Distractors with the prongs inserted into the vertebrae.

FIG. 37 is a bottom plan view of the foot plate of the apparatus of the present invention for use in installing the interbody spinal implants having one or more flat sides.

FIG. 38 is a cross sectional view along line 38-38 of FIG. 36 illustrating the apparatus used for inserting interbody spinal implants having one or more flat sides.

FIG. 39 is a partial fragmentary view of the apparatus of the present invention for use in installing interbody spinal implants having one or more flat sides, shown with the prongs being partially inserted into the vertebrae.

Figure 1:
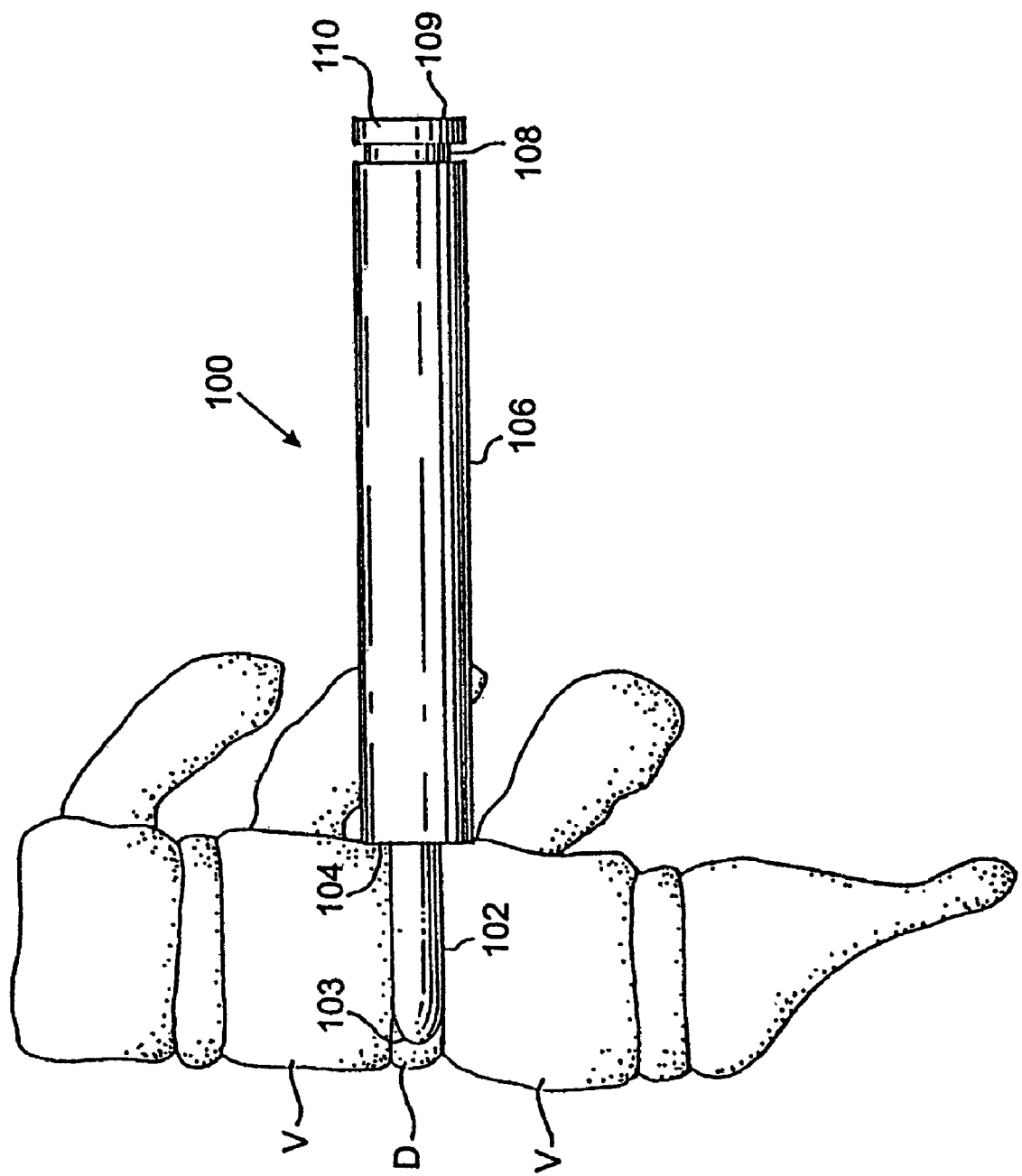
FIG. 1 is a side elevational view of the Long Distractor, of the present invention inserted into the intervertebral space.

DETAILED DESCRIPTION OF THE DRAWINGS AND DETAILED DESCRIPTION OF METHOD OF INSERTION

The following discussion will be in regard to application in the lumbar spine via the posterior approach. In its simplest form, the method of the present invention involves the following steps. The patient is placed on a spinal surgery frame, which allows for the distraction and alignment of the disc space to be fused. A bilateral posterior exposure of the interspace, with or without partial discectomy is then performed. Utilizing distractors the disc space is distracted, and a hollow Outer Sleeve is fitted over one of the distractors. The end of the Outer Sleeve has engagement means, such as teeth, for engaging the two adjacent vertebrae. The Outer Sleeve is driven into the vertebrae and the distractor is then removed. A hollow Inner Sleeve is then inserted into the Outer Sleeve and a stopped Drill is utilized to prepare the opposed vertebral surfaces. The Drill and the Inner Sleeve are removed as a single unit. The space is tapped if so required. The prepared spinal implant is then inserted via the Outer Sleeve utilizing a stopped inserter. The instruments are then removed and the procedure repeated on the contralateral side of the spine.

Detailed Description of the Preferred Embodiment

Step 1a. Prior to surgery, translucent implant templates appropriately adjusted for scale are superimposed on AP, lateral, and axial images of the interspace to be fused, for the purpose of selecting the optimal implant size and to determine the desired distraction.

Step 1b. The patient is preferably placed onto a spinal surgery frame capable of inducing both distraction and vertebral alignment.

Step 2. In the preferred embodiment, a standard bilateral (partial) discectomy is performed and any posterior lipping of the vertebral bodies adjacent the interspace is removed. Alternatively, no disc material need be removed. In the preferred embodiment, the interspace is exposed by performing bilateral paired semihemilaminotomies and resecting the inner aspects of the facet joints adjacent the spinal canal while preserving the supra and interspinous ligaments.

Step 3. Beginning on the first side, the dural sac and traversing nerve root at that level are retracted medially and a Long Distractor then inserted and impacted flush to the posterior vertebral bodies adjacent that interspace. Long Distractors with working ends of increasing diameter are then sequentially inserted until the optimal distraction is obtained. This optimal distraction not only restores the normal height of the interspace, but further achieves a balance wherein the tendency for the space to collapse is resisted, which in urging the vertebral bodies apart is being equally resisted by the powerful soft tissue structures about the spinal segment including the outer casing of the disc (the annulus fibrosus), various ligaments, capsular structures, as well as the muscles and other soft tissue structures. This balanced distraction not only provides for the spatial restoration of the height of the interspace, but for considerable stability as the space now resists further distraction or collapse.

In the preferred embodiment, as the desired distraction is approached, the use of the solid bodied Long Distractors is terminated and a disassemblable Convertible Distractor is placed with tactile and/or radiographic confirmation of ideal distraction. The Convertible Distractor is then disassembled such that the Short Distractor portion is left in place and the ultra-low profile head portion being positioned adjacent to the canal floor and safely away from the neural structures. To insure that the Short Distractor remains in place until its removal is desired, various embodiments of the Short Distractor are available with varying degrees of resistance to dislodgment. In the preferred embodiment of the procedure, attention is then directed to the contralateral side of the spine.

Step 4. On the contralateral side of the same interspace the Long Distractor having at its working end the diameter matching the Short Distractor already in place, is then inserted. If however, due to an asymmetrical collapse of the interspace if it is then determined that greater distraction is required on the second side to achieve the optimal stability, then the appropriate Short Distractor would be placed on the second side. Then the Short Distractor would be removed from the first side and replaced with a larger Long Distractor so as to bring the interspace into balance.

In an alternative embodiment, the entire procedure is performed on the one side of the spine utilizing only the Long Distractor prior to repeating the procedure on the contralateral side of the spine. While this method can be performed in accordance with the remaining steps as described in the preferred embodiment, when utilized it is best performed using a Trephine which allows the Long Distractor to remain in place, thereby allowing for interspace distraction otherwise provided in the first method by the Short Distractor. This alternative method then requires the use of a Trephine over the Long Distractor in lieu of a reamer and is therefore called the "Trephine Method", which will be discussed in detail later.

Step 5. With the Short Distractor in place on the first side of the spine, and the matching Long Distractor in place on the second side of the spine, and with the dural sac and traversing nerve root safely retracted, the Outer Sleeve is placed over the Long Distractor and firmly impacted to its optimal depth using the Impaction Cap and a mallet. The Long Distractor is then removed.

Step 6. An Inner Sleeve is then placed within the Outer Sleeve, and the interspace is then prepared on that side by utilizing a boring means such as, but not limited to, a Drill, Endmill, Reamer, or Trephine to drill, ream, or cut out the bone to be removed to either side, as well as any remaining interposed discal material. In the preferred method, utilizing a specially designed Endmill-Drill, it and the Inner Sleeve are removed as a unit, safely carrying away the bone and disc debris trapped within them from the spinal canal.

Step 7. If required, a thread forming Tap with penetration limiting means to control the depth of insertion, is then inserted through the Outer Sleeve.

Step 8. The prepared implant is then inserted utilizing the specialized Driver unit. It should be noted that the implant may be coated with, and/or made of, and/or loaded with substances consistent with bony fusion which may promote bone growth and/or fusion. However, in the preferred embodiment, the implant is treated with bone promoting and inducing substances, but is loaded with materials suitable for participating in a fusion.

While substances both natural and artificial are covered by the present invention, the preferred embodiment is in regard to the use of the patient's own bone by the following method. A hollow Trephine is utilized to harvest a core of bone from the posterior superior aspect of the iliac crest adjacent the sacroiliac joint. This core of bone is at its outside diameter, slightly smaller than the inside diameter of the spinal implant to be loaded, but longer than the spinal implant. Utilizing an instrument designed for that purpose, the core of bone is then injected from within the Trephine into the central cavity of the implant causing a superabundance of the bone material within the implant such that the bone material tends to press out through the openings communicating with the outside surface of the implant.

Step 9. Using the Driver Extractor instrument, the prepared implant is threaded into the prepared interspace. The instrumentation is removed from that side of the spine and attention is then redirected to the first side of the spine. A small retractor is utilized to move the dural sac and traversing nerve root medially and to protect them and allowing the direct visualization of the retained Short Distractor unit. Without removing the Short Distractor, it is reassembled to its shaft portion, essentially reconstituting itself into a Long Distractor. With the inserted implant now acting as the distractor on the opposite side, the Long Distractor is utilized to guide the Outer Sleeve down where it is impacted as described in Step 5.

Steps 6 & 7 are then repeated, completing the procedure at that level. The wound is then irrigated and closed in the routine manner.

Representative Example of The Preferred Method

Through preoperative templating of the patient's anterior posterior, lateral, and axially imaged MRI scan in conjunction with translucent overlays of the various sized implants, the correct implant diameter and length are accurately assessed, as well as the correct amount of distraction needed to restore the interspace to its premorbid height. The patient is then properly positioned and a bilateral partial discectomy performed via paired semihemilaminotomies.

For the purpose of this example, it will be assumed that by preoperative assessment it was determined that the correct implant would have an external diameter of 18 mm and be 26 mm long. Further, the distraction necessary to restore the height of the interspace would be approximately 10 mm. The dural sac and traversing nerve root would then be retracted medially and protected, while a Long Distractor having an outside diameter at the barrel portion corresponding to the implant to be inserted, that is 18 mm, and having a diameter at the working end of perhaps 8 mm, would be inserted. This then being found to be slightly smaller than optimal by direct observation, a Convertible Distractor having in its barrel portion an 18 mm outside diameter, but having in its working portion a 10 mm diameter would then be inserted. Direct observation and/or x-ray then confirming the ideal distraction, the Convertible Distractor would then be disassembled, the barrel and head portion removed, and the Short Distractor portion left deeply embedded and with its flanged head flat against the canal floor and deep to the neural structures. It would then be safe to allow the dural sac and nerve root to return to their normal positions, which would be superficial to the flanged portion of the Short Distractor.

Attention would then be directed to the contralateral side. The dural sac and nerve root would then be retracted medially on this second side, and a Long Distractor with an 18 mm diameter barrel portion and a 10 mm working portion would then be inserted into the interspace and driven flush to the bone if necessary, such impaction imploding any osteophytes not already removed, and assuring that the shoulder portion of the barrel comes to lie flat against the posterior aspects of the adjacent bodies. With the dural sac and nerve root still safely retracted, the Outer Sleeve would then be placed over the Long Distractor and utilizing the Driver Cap and a mallet, seated to the optimal depth.

In the preferred embodiment, the Long Distractor is then removed and the Inner Sleeve is inserted into the Outer Sleeve. Since the purpose of the Inner Sleeve is to support the drill and allow for the increased size of the implant over the size of the drill, thus making it possible for the insertion of the implant to occur through the Outer Sleeve, the Inner Sleeve therefore measures 18 mm in its outside diameter, and 16.6 mm in its inside diameter. This allows it to fit within the Outer Sleeve, the diameter of which is 18.1 mm and to admit the drill bit which is 16.5 mm in diameter.

Following the drilling procedure, the Drill and Inner Sleeve are removed as a single unit with the trapped interposed cartilaginous and bony debris. The depth of drill penetration is preset and limited by the fixed rigid column of the Outer Sleeve. In this example, the space will be prepared to a depth of 28 mm in anticipation of countersinking a 26 mm long implant at least 2 mm. If a Tap were to be utilized, it would be inserted at this time and be appropriate to the minor and major diameters of the implant to be inserted and as with the Drill, controlled for its depth of penetration. The spinal implant would then be prepared for implantation by utilizing a Trephine to harvest a core of posterior iliac bone greater than 30 mm long and approximately 14.5 mm in diameter.

Using the Bone Loading Device, this core of bone would be forcefully injected into the internal chamber of the spinal implant which would then be capped. Cap end forward, the fully loaded implant would then be attached to the Insertion Driver, down the Outer Sleeve and screwed into place with the depth of penetration limited by the Insertion Driver. The Insertion Driver is then unscrewed from the implant and removed from the Outer Sleeve. With the dural sac and nerve root retracted and protected, the Outer Sleeve would then be removed. This would complete the fusion procedure on that side, and then as described, the procedure would be repeated on the other (first) side of the same interspace.

Alternative Methods

An alternative and extremely useful method is the "Trephine Method". Its advantages include that it may be used in conjunction with the preferred embodiment substituting the use of a hollow, tubular cutter, called a Trephine for the use of the Drill in Step 5 of the preferred embodiment. Additionally, it may be utilized so as to obviate the need for the placement of the Short Distractor and to allow the procedure to be effectively performed from start to finish on one side prior to initiating the procedure on the opposite side, and while nevertheless maintaining distraction at the site of the bone removal.

The following is a description of the "Trephine Method". Having completed the exposure of the interspace on at least one side, the dural sac and nerve root are retracted. A Long Distractor differing from the Long Solid Bodied Distractor of the preferred embodiment only in that the barrel portion is of a precisely lesser diameter than the spinal implant. As in the preferred embodiment, the Outer Sleeve has an inner diameter only slightly greater than the implant to be inserted. Therefore, at this time, a first Inner Sleeve is inserted into the Outer Sleeve to make up the difference between the outside diameter of the Long Distractor and the inside diameter of the Outer Sleeve. With the Outer Sleeve and first Inner Sleeve thus assembled, they are placed over the Long Distractor and the Outer Sleeve is optimally seated using the Impaction Cap. The Cap and first Inner Sleeve are removed, but the Long Distractor and Outer Sleeve are left in place.

With the Long Distractor maintaining optimal distraction and with the Outer Sleeve locking the vertebrae together so as to resist any movement of the vertebrae, a hollow, tubular cutter known as a Trephine is then inserted over the Long Distractor and its barrel portion and within the Outer Sleeve. The Trephine, which is stopped out to the appropriate depth, can then be utilized to cut equal arcs of bone from the opposed vertebral endplates.

Alternatively, a second Inner Sleeve may be placed within the Outer Sleeve prior to placing the Trephine over the Long Distractor and within that second sleeve. This second Inner Sleeve would be just greater in its internal diameter than the Long Distractor and just smaller in its outside diameter than the inner diameter of the Outer Sleeve. While it would provide enhanced stability to the Trephine, provision would then need to be made in the way of large flutes passing longitudinally or obliquely along the outer surface of the Distractor to its barrel portion to accommodate the bony and cartilaginous debris generated during the cutting procedure.

Following the use of the Trephine to the appropriate depth by either of these methods, the Trephine, the Long Distractor, and the second Inner Sleeve, if utilized, are all removed. Since the Trephine cuts two arcs of bone but does not ream them out, a shafted instrument with a perpendicular cutting portion at its working end is then inserted parallel to the disc space and then rotated through an arc of motion cutting the bases of the two longitudinally cut arcs, thus freeing them for removal through the Outer Sleeve. The space may then be tapped if required, and the implant is inserted as per the preferred method. As already mentioned, the "Trephine Method" can be used with or without the use of the Short Distractor on the contralateral side.

Applications of Method in Other Areas of the Spine

The following method is the preferred embodiment for performing anterior interbody fusion in the thoracic and lumbar spines. It is also appropriate in the cervical spine when the width of the spine anteriorly is sufficient so that it is possible to place two implants side by side and such that each intrudes at least several millimeters into the substance of the opposed vertebrae and for the length of the implants.

The interspace to be fused is adequately exposed and the soft tissues and vital structures retracted and protected to either side. Visualization of the broad width of the interspace anteriorly is made possible by the absence of the neurological structures in relation to this aspect of the spine. The center line of the anterior aspect of the interspace is noted and marked. The disc is removed using first a knife and then curettes and rongeurs as needed. Alternatively, the disc may be left intact to be removed during the drilling stage of the procedure. However, as per the preferred embodiment of the procedure, having removed the great mass of the nucleus and the greater portion of the annulus anteriorly, Long Distractors with progressively increasing diameters to their working ends are inserted into the interspace at a point midway between the central marking line and the lateral extent of the anterior aspect of the spine as visualized.

The Dual Outer Sleeve with its common Foot Plate and Retention Prongs is then inserted over either a singly placed Long Distractor and then the second Distractor placed, or is placed over both Distractors if already placed. The Dual Outer Sleeve is then seated firmly against the anterior aspect of the spine. Any spurs which would interfere with the flush seating of the Foot Plate to the anterior aspect of the spine should be removed prior to inserting the Long Distractors. Once the Outer Sleeve has been optimally seated, one of the Long Distractors is removed and in its place is inserted an Inner Sleeve and drill bit. The drill bit has as its outside diameter the minor diameter of the implant to be inserted. The Inner Sleeve is essentially equal in thickness to the difference between the minor and major diameters of the threaded implant.

A Stopped Drill is then utilized to prepare the opposed vertebral surfaces and to remove any remaining disc material interposed. If required, a Stopped Tap may be inserted through the Outer Sleeve and into the interspace to create a thread form. The properly prepared implant is then affixed to the Insertion Driver and passed through the Outer Sleeve down into the interspace and inserted until its depth of penetration is limited by the stop on the Insertion Driver. With the implant itself now in a position to act as a distractor, the Long Distractor is then removed from the contralateral side and the procedure repeated. When both implants are firmly in place, the outer sleeve may then be removed. The amount of countersinking of the implants may then be adjusted under direct vision.

Detailed Description of the Preferred Embodiment Method and Instrumentation

In the preferred embodiment, the disc (D) between adjacent vertebrae (V) is approached via bilateral paired semi-hemilaminotomies of the adjacent vertebrae. In the preferred embodiment the supraspinous ligament, the interspinous ligament, the spinous process, portions of the lamina, and most of the facet joints are preserved. However, while less desirable, these structures may be removed.

In the preferred method, a bilateral partial nuclear discectomy is then performed through bilateral openings created through the posterior aspect of the annulus fibrosus. While considered less desirable, disc excision can be delayed and performed simultaneously with the vertebral bone resection during the drilling procedure. Starting on the first side, a dural nerve root retractor is placed such that the dural sac and lower nerve root are retracted medially allowing exposure to one side of a portion of two adjacent vertebral bodies and the interposed disc posteriorly.

Referring now to FIG. 1, preferably after removing some portion of nuclear disc material, a Long Distractor 100 is inserted under direct vision into the intervertebral space. The disc penetrating portion 102 is essentially cylindrical with a bullet-shaped front end 103 and a shoulder portion 104 where the penetrating portion 102 extends from barrel 106. The penetrating portion 102 urges the vertebral bodies apart, facilitating the introduction of the instruments. Long Distractors with sequentially increasing diameter penetrating portions 102 are then introduced. As the optimal diameter of penetrating portion 102 is achieved, the Vertebrae V to either side are forced into full congruence and thus become parallel, not only to the penetrating portion 102, but to each other. At this time, any remaining excrescences of bone of the posterior vertebral bodies adjacent the posterior disc which have not already been removed are flattened flush to the vertebral body by the forced impaction, such as by hitting with a hammer flat surface 109 of crown 110, driving the shoulder 104 against the lipped portions of vertebrae V. Because of the forced opposition of the vertebral endplates to portion 102 with optimal distraction, Long Distractor 100 will then come to lie absolutely perpendicular to the plane of the posterior bodies and absolutely parallel to the vertebral endplates, allowing optimal alignment for the procedure to be performed.

Penetrating portion 102 is available in various diameters, but all are of a constant length, which is less than the known depth of the interspace. This combined with the circumferential shoulder 104, which is too large to fit within the interspace, protects against the danger of overpenetration. Barrel 106 is of the same diameter as the external diameter of the device to be implanted. A recessed portion 108 below the crown 110 allows for the Long Distractor 100 to be engaged by an extractor unit shown in FIG. 9.

Figure 2:
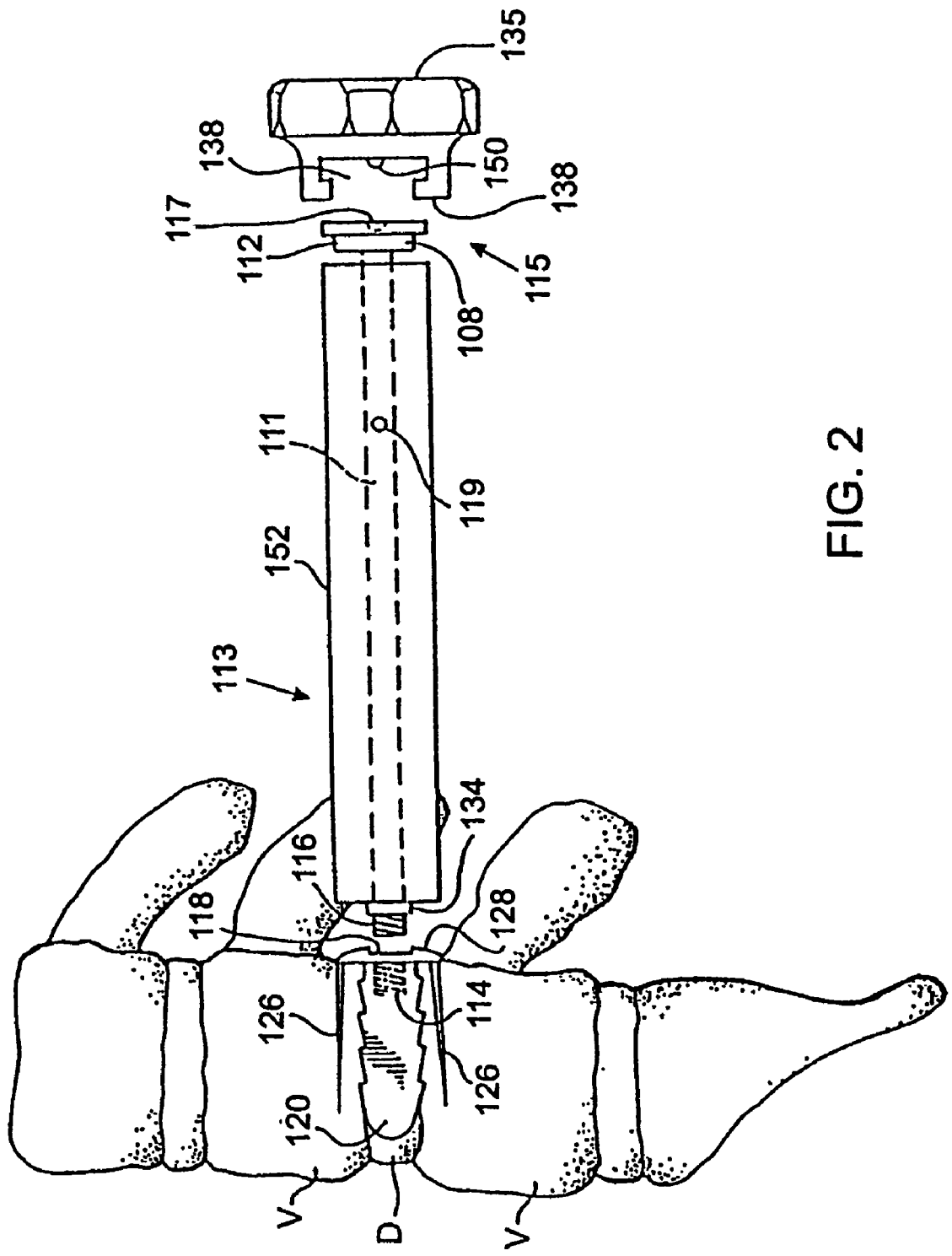
FIG. 2 is a side elevational view of a Convertible Distractor assembly in relation to the spine.

Referring to FIG. 2, in the preferred embodiment, a Convertible Long Distractor 113 is used on the first side of the spine. The Convertible Long Distractor 113 has a barrel portion 152 separable from the Short Distractor portion 120. While the initial distraction may be performed with a solid Long Distractor, as the optimal distraction is approached the appropriate Convertible Long Distractor is utilized. The Convertible Long Distractor 113 consists of a Short Distractor portion 120 and a barrel 152 having a rectangular projection 134 at one end. The Short Distractor 120 has an increased diameter head 128, a rectangular slot 118 and an internal threaded opening 114. The barrel 152 is hollow and has an internal shaft 111 terminating in a large diameter hexagonal crown 115 at one end and a reduced diameter portion 112. The crown 115 has a detent portion 117 in its flat surface. The other end of the shaft 111 has a threaded working end screw 116 that corresponds to threaded opening 114. The shaft 111 is prevented from removal from the barrel 152 by set pin 119 passing through the wall of barrel 152 in a convenient manner. The Short Distractor portion 120 is removably attached to the barrel portion 152 via the mating of female rectangular slot 118 and the male mating member 134. The mating held together by utilizing knob 135 to drive the crown 110 connected to interior shaft 111 having a threaded working end screw 116 that threads into the female rectangular slot 118 of the Short Distractor portion 120.

Knob 135 has an open socket 138 for fitting around crown 115 and engages the reduced diameter hexagonal portion 112 so as to permit the rotation of shaft 111 and threaded working end screw 116. A detent ball 150 in the inside of the socket 138 engages detent 117 in the crown 115, holding them together.

Figure 3:
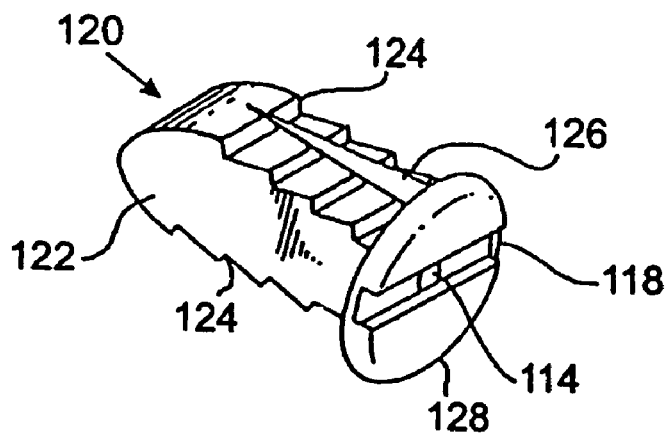
FIG. 3 is a perspective view of a high retention Short Distractor of FIG. 2.
Figure 3A:
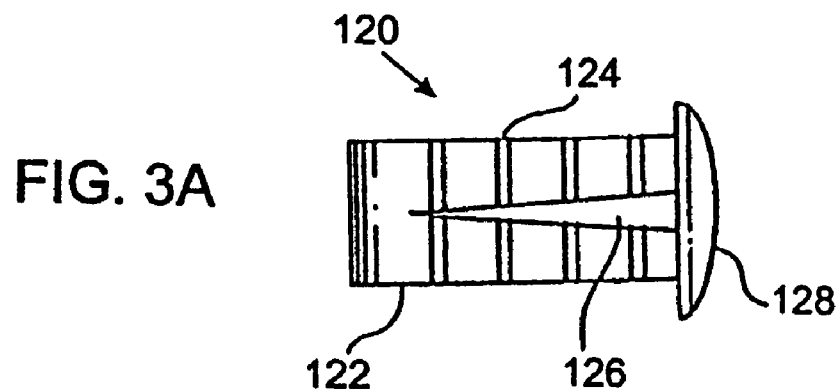
FIG. 3A is a side elevational view of the high retention Short Distractor of FIG. 3.
Figure 3B:
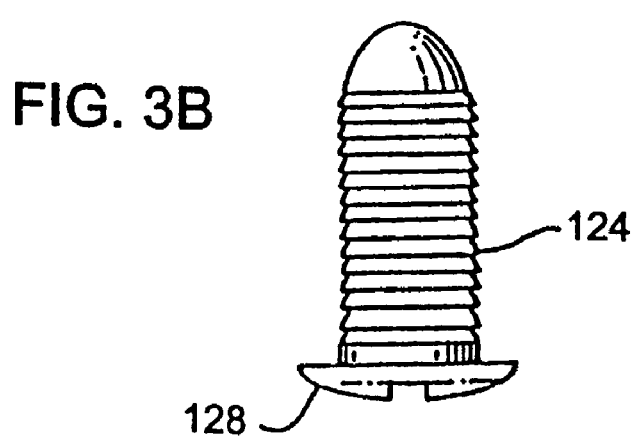
FIG. 3B is a side elevational view of an alternative Short Distractor with circumferential forward facing ratchetings.
Figure 3C:
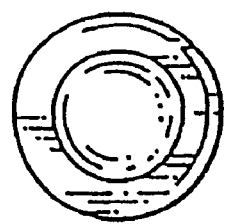
FIG. 3C is a top view of the alternative Short Distractor of FIG. 3B.

Referring to FIGS. 2, 3, and 3A-3F the Short Distractor portion 120 are designed to provide for high stability when temporarily situated so as to resist inadvertent migration while the surgeon is working on the second side. To that end, the embodiment of the Short Distractor 120 shown in FIGS. 3 and 3A, has a pair of sharp pegs 126, to embed into the opposing vertebral bodies and forward facing ratchetings 124, that further resist backward movement. FIGS. 3B and 3C, which show the preferred embodiment, are side and top views of an alternative embodiment of the distractor portion such that the distractor portion to be interposed between the vertebrae is essentially cylindrical, but with circumferential forward facing ratchetings 124.

Figure 3D:
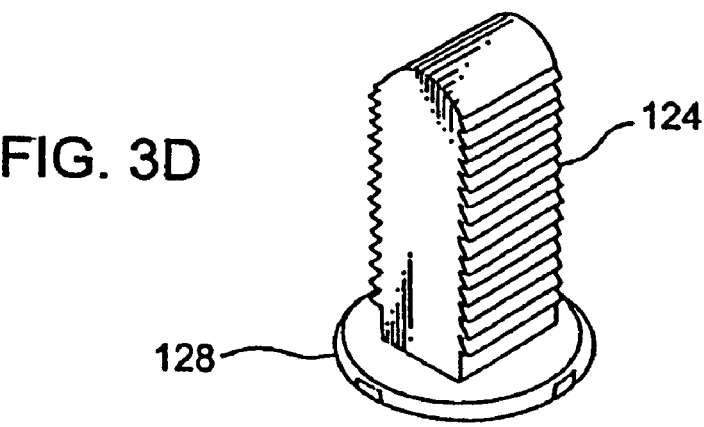
FIG. 3D is a perspective view of an alternative embodiment of a Short Distractor.
Figure 3E:
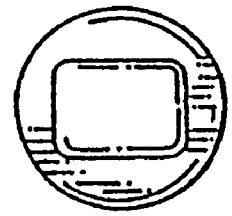
FIG. 3E is a top view of the alternative distractor of FIG. 3D.
Figure 3F:
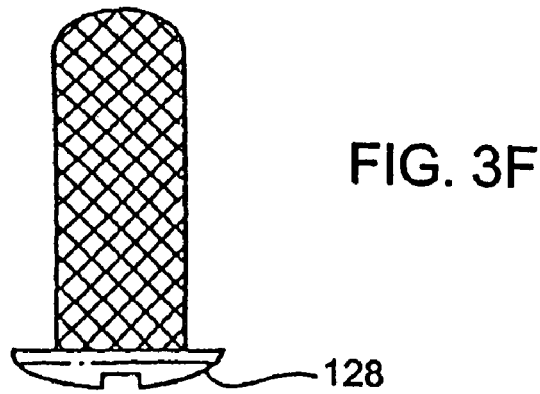
FIG. 3F is a side elevational view of a further alternative rectangularized Short Distractor with knurled surfaces.

Referring to FIGS. 3D and 3E, a further alternative embodiment of the Short Distractor is shown. This is a more rectangularized design, with forward facing ratchetings, without the sharp prongs 126 of FIG. 3. FIG. 3F is a side view of a further embodiment of the Short Distractor 120 shown with knurling, to increase the interference with the bone surface so as to add stability to the unit and to resist dislodgment. To this end, it is apparent that the working ends of both the Long and Short Distractors can have a variety of configurations consistent with their purpose, and that surface irregularities as well as the shape of the ends themselves, with or without prongs 126, may be utilized to make the Short Distractor 120 more resistant to migration.

Once the ideal distraction has been achieved on the first side of the spine, the Convertible Distractor is dissociated, leaving Short Distractor 120 in place with its rounded external end 128, safely on the canal floor and deep to the dural sac and nerve root.

Figure 4:
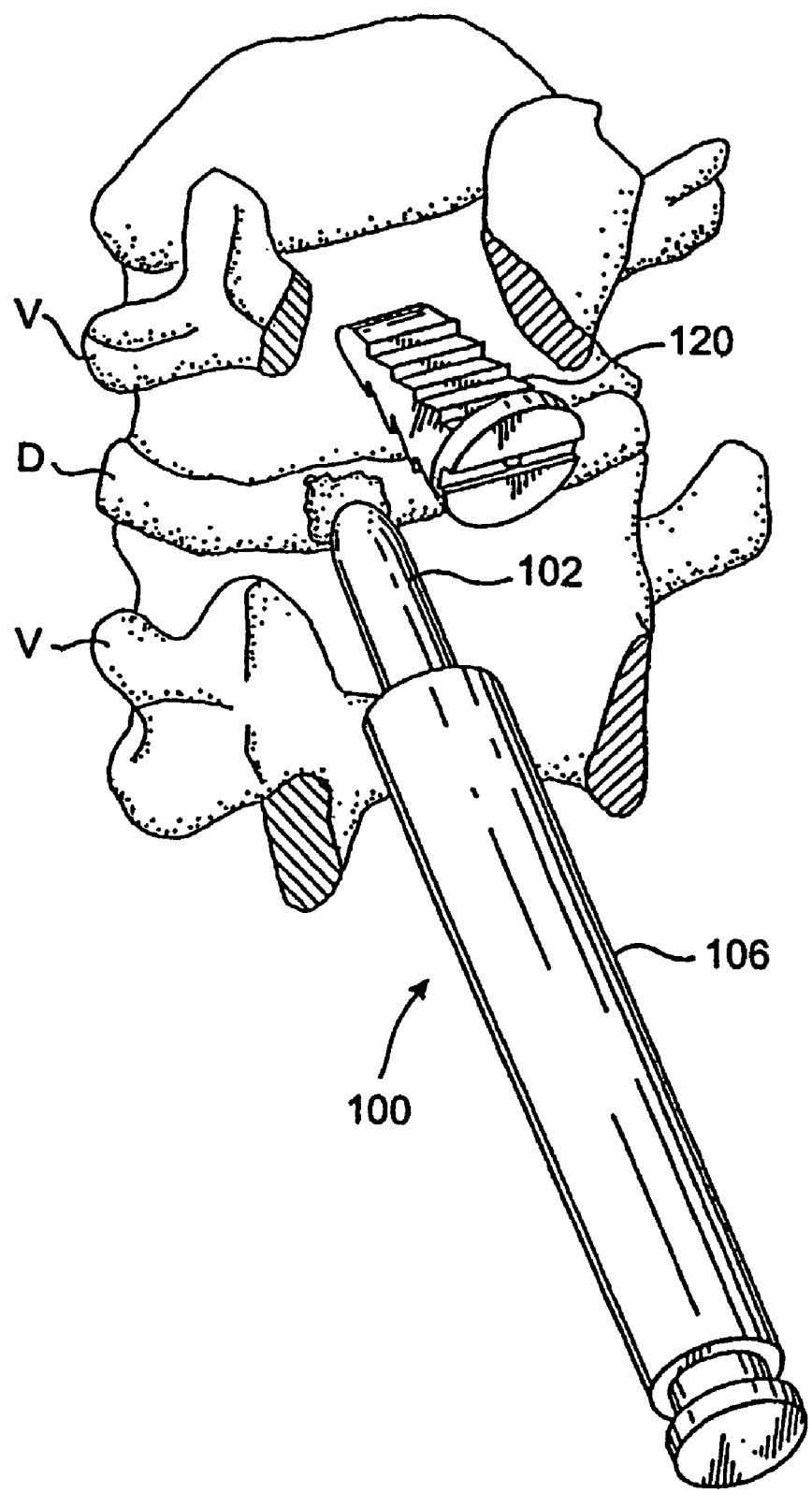
FIG. 4 is a perspective view of a spinal segment (two vertebrae and an interposed disc) with a Short Distractor in place, with a portion of the upper vertebrae and disc cut away to show the Short Distractor on one side of the spine and the Long Distractor about to be placed contralaterally.

Referring to FIG. 4, the surgeon then moves to the other side of the spine at the same disc (D) level, and retracts the dural sac and nerve root medially, exposing the disc on that side. Long Distractors 100 are then sequentially inserted into the disc space until the diameter of the distractor on the second side is at least as big as that on the first side. If because of some asymmetry of the interspace, a larger diameter distractor is required on the second side to achieve the ideal distraction as compared to the first side, then the second side is fitted with a Short Distractor of the larger diameter, and the surgeon would then return back to the first side. In that event, the first side Short Distractor would then be removed and the Long Distractor 100 corresponding to the increased diameter of the already placed Short Distractor 120 would then be inserted. In either event, the operation is continued by working on the one side where the Long Distractor is in place. In this regard, it should be noted, that by the use of such a device as the Michelson Otrhopedic Support Frame, U.S. Pat. No. 4,481,943 issued on Nov. 13, 1984, it may be possible to obtain adequate distraction preoperatively such that the surgeon is either disinclined to use a distractor, or to simply place the correct Long Distractor on the first side and then proceed with the surgical procedure on that side before moving to the opposite side. These variations are within the scope of the present invention.

Figure 5:
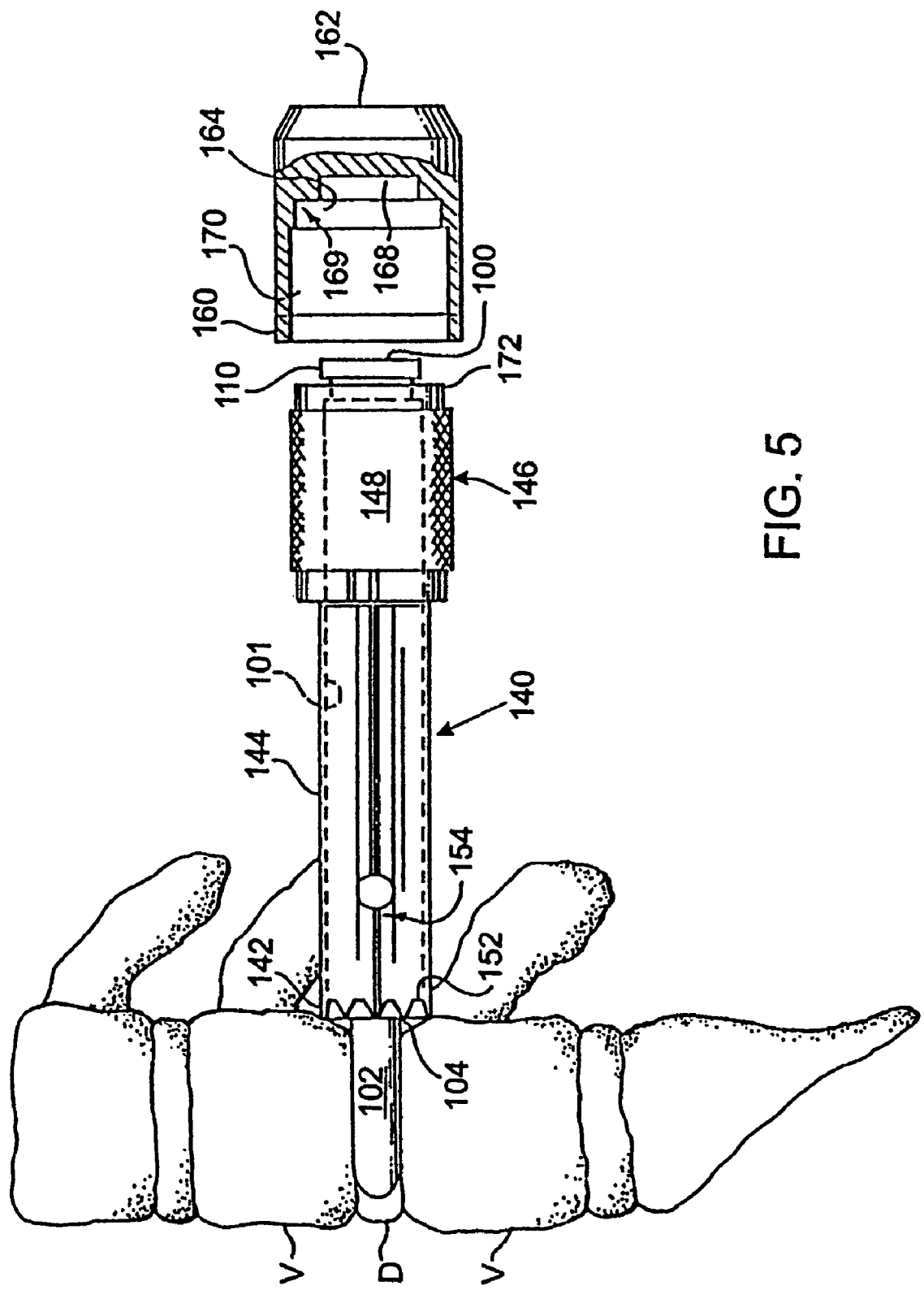
FIG. 5 is a side elevational view of the Outer Sleeve in place over the Long Distractor, and about to receive the Driver Cap in preparation for being seated.

Referring to FIG. 5, the Long Distractor 100 now serves as both a centering post and an alignment rod for the hollow Outer Sleeve 140 which is fitted over the Long Distractor 100, shown by phantom lines 101. The front end of the Outer Sleeve 140 is metal and has sharp teeth 142 that are capable of penetrating into and holding fast the two adjacent vertebrae (V). Interrupting the circumferential sharp teeth 142 are flat, planar areas 152 which serve to resist the further insertion of the sharp teeth 142 into the vertebral bodies. The sharp teeth 142 of the Outer Sleeve 140 are a continuation of the tubular shaft 144, which in turn is connected to circumferentially enlarged tubular back end 146 having a knurled outer surface 148 for easier manipulation. An alternative embodiment of an Outer Sleeve incorporates an expansible key hole and slot configuration 154 to either side of shaft 144 along the midplane of the interspace and parallel to it such that the end 142 resists the collapse of the vertebrae (V) to either side of the disc (D), but may nevertheless allow for their further distraction, in the event the only diameter or the root diameter of the implant is larger than the hole drilled.

A Driver Cap 160 in the form of an impaction cap has at its far end a flat, closed-back surface 162 and at its other end a broad, circular opening. The Driver Cap 160 fits over both the Outer Sleeve 140 and the Long Distractor 100. As the Driver Cap 160 is seated, interior surface 170 circumferentially engages portion 146 of the Outer Sleeve until the back end 172 engages the internal shoulder 164. As mallet blows are applied to surface 162, that force is transmitted via the internal shoulder 164 to the Outer Sleeve 140 via its far end 172, seating sharp teeth 142 into the vertebral bodies adjacent the disc space D and to the depth of the teeth sharp 142 to the flat portions 152. As the Outer Sleeve 140 is advanced forward, crown portion 110 of the Long Distractor is allowed to protrude within the Driver Cap 160 unobstructed until it contacts the interior flat surface 168.

Figure 6:
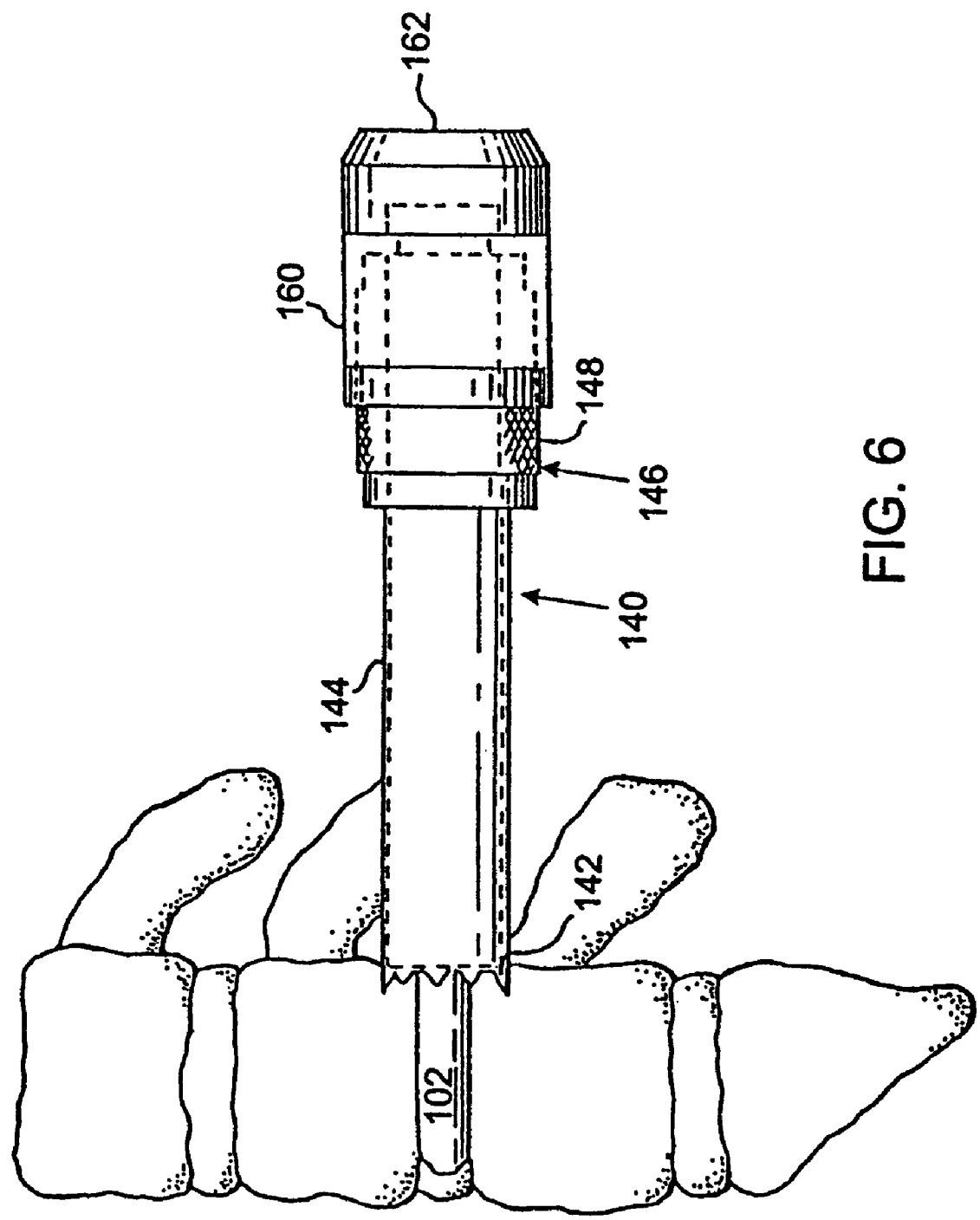
FIG. 6 is a side elevational view of the Long Distractor, Outer Sleeve, and Driver Cap following the proper seating of the Outer Sleeve into the two adjacent vertebrae.
Figure 8:
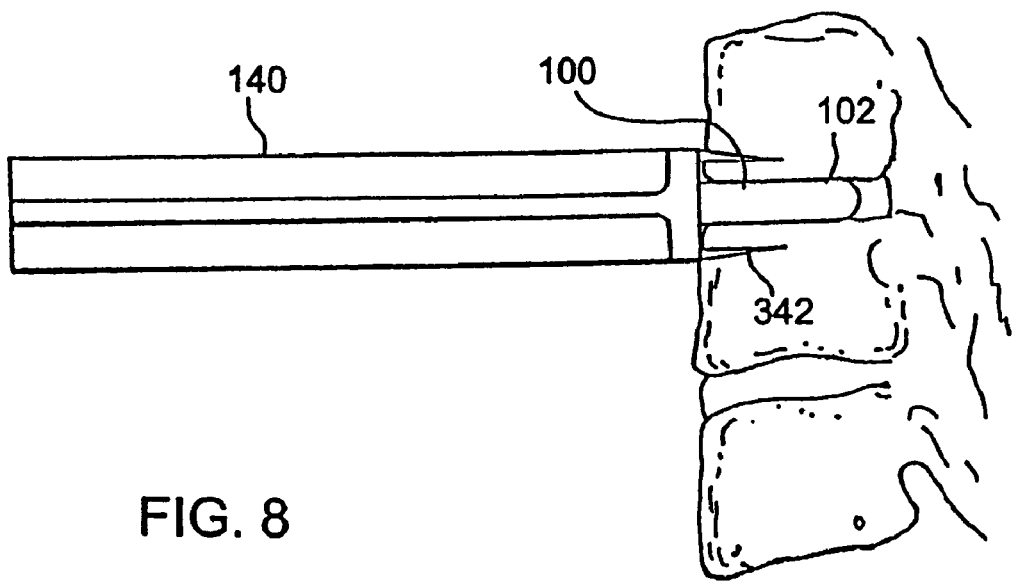
FIG. 8 is a side elevational view of the Outer Sleeve of FIG. 7A centered on the Long Distractor and fully seated on the anterior aspect of the cervical spine.

Referring to FIG. 6, once crown 110 comes into contact with the flat interior surface 168, then further taps of the mallet will not advance the Outer Sleeve, any further motion being resisted by the flat shoulder portion 104 of the Long Distractor abutting the hard surfaces of the posterior vertebral bodies. In this way, the Outer Sleeve 140 is safely and assuredly inserted to its optimal depth and rigidly securing the two opposed vertebrae as shown in FIG. 6.

Figure 9:
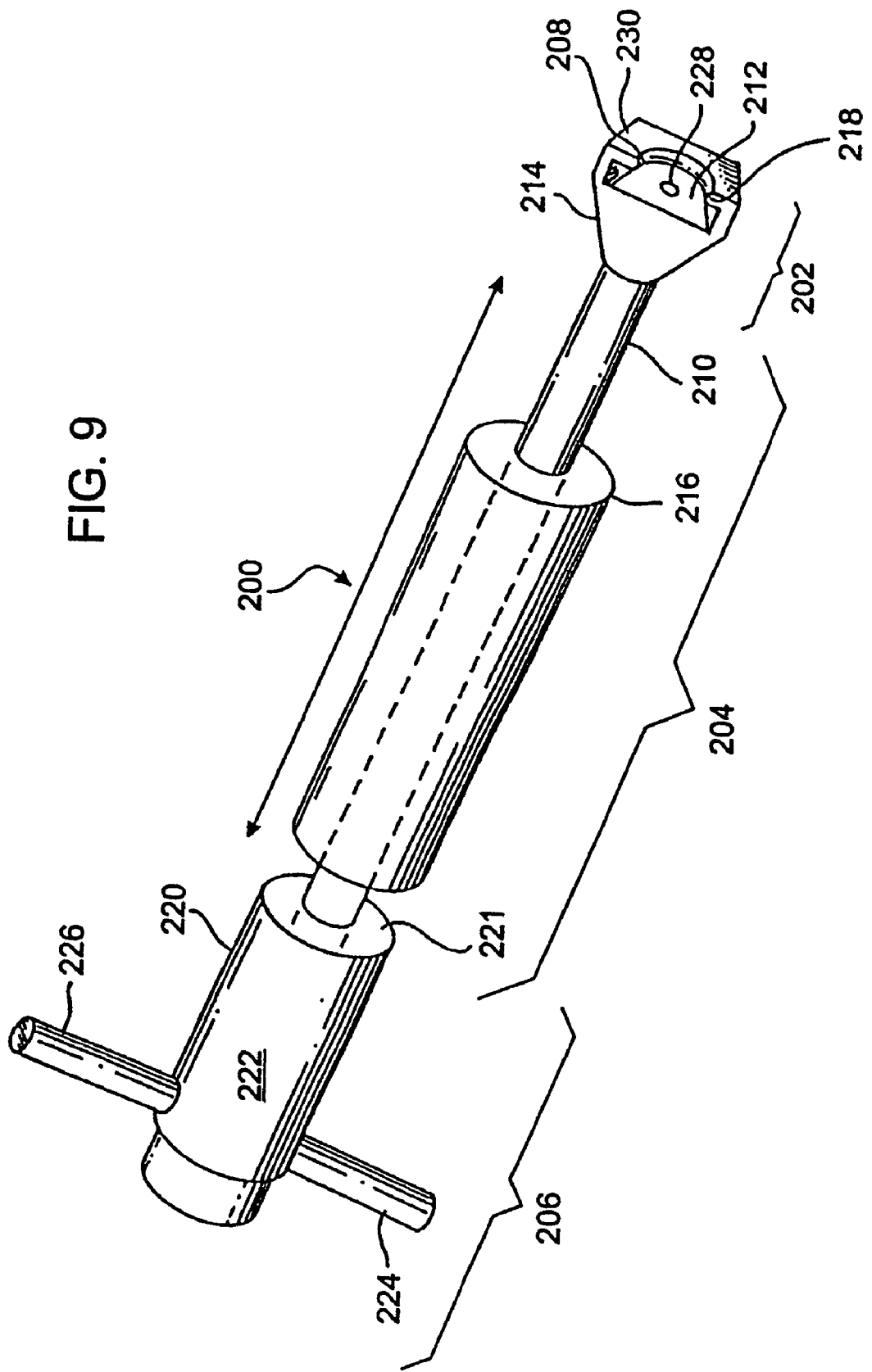
FIG. 9 is a perspective side view of the Distractor Puller.

Referring to FIG. 9, the Cap 160 is then removed and the Distractor Puller 200 of FIG. 9 utilized to remove the Long Distractor 100 from the spine leaving the Outer Sleeve 140 in place. The Distractor Puller 200 has front portion 202, a mid portion 204, and a back handle portion 206. At the front portion 202 of the Distractor Puller 200, a socket 208 is connected to one end of shaft 210 which at its far end is connected to back handle portion 206. The socket 208 has defined within it a cavity 212 that is open at its front end and funnelized on the interior aspect of its sides. The cavity 212 is constructed so that the head of the Distractor Puller 200 and the partially circumferential flange 218 engages the circumferential recess 108 of the Distractor 100. The entrance to cavity 212 is slightly funnelized, and the leading edges of flange 218 slightly rounded to facilitate the engagement of recess 108 and head 110 of Distractor 100, which is further facilitated in that the Driver Cap 160 leaves portion 108 of Distractor 100 precisely flush with the back surface 172 of the Outer Sleeve 140. This provides a large, flat surface 172 to precisely guide surface 230 of socket 208, and open portion 212 around head 110 while flange 218 engages recess 108. The springloaded detent ball 228 engages hemispherical depression 112 in the crown 110, shown in FIG. 2. This springloaded detent 228 in engagement with complimentary indent 218 protects against the inadvertent dissociation of the Long Distractor from the Puller 200 after the Distractor has been removed from within the Outer Sleeve 140 and prior to its removal from the wound. Once out of the body, the two instruments are easily disassociated by freeing the crown portion 110 from cavity 212 by a manual force applied perpendicular to their relative long axes at this location.

A cylindrical and free removable weight 216 is fitted around shaft 210 between the front portion 202 and the rear handle portion 206. Gently, but repeatedly sliding the weight 216 along shaft 210 and driven rearwardly against flat surface 228, transmits a rearward vector to proximal end 202 and thereby to the Long Distractor 100 to which it is engaged.

Paired extended handle 224 and 226, allow the surgeon to resist any excessive rearward motion as the instrument is used to liberate the Long Distractor 100. Paired handles 224 and 226 are also useful in that they allow a rotational directing of portion 208, via the shaft 210. This allows the surgeon to control and manipulate rotationally the orientation of the opening of cavity 212 to facilitate its application, to the head 110 of the distractor 100.

The Distractor Puller 200 is a significant improvement over the alternatives of striking a remover instrument with an independent hammer over the exposed surgical wound, or manually extracting the distractor by forcefully pulling. The use of a free hammer over the open wound is dangerous because the neural structures can be impacted on the back swing which is made even more likely by the effects of gravity on the mallet head. Manual extraction by pulling is dangerous because of the significant interference fit of portion 102 within the spine such that significant force would be required to remove the Distractor 100, and if force were not coaxial then the Outer Sleeve might be dislodged or misaligned. Further, once the flat portion 102 became free of the interspace, all resistance to withdrawal would be lost and in the face of the considerable force necessary to free it, the Distractor 100 might easily become projectile imparting injury to the patient and/or the surgeon.

Once the Long Distractor 100 has been fully removed from the Outer Sleeve 140, the toothed end 142 of the Outer Sleeve 140, working in conjunction with the Short Distractor 120 on the contralateral side rigidly maintains the relative position of the adjacent vertebrae V. Further, since the remainder of the procedure on that side of the spine occurs entirely through the protective Outer Sleeve 140, and as the nerves and dural sac are external to that Outer Sleeve and superficial to the toothed end 142 of the Outer Sleeve 140, which is firmly embedded into the adjacent vertebrae V, the Outer Sleeve 140 serves to insure the safety of these delicate neural structures. Further, since the Outer Sleeve 140 is of a fixed length and rigid, its flat rearward surface 172 may be used as a stop to the advancement of all instruments placed through the Outer Sleeve 140, thus protecting against accidental overpenetration. Further, the Outer Sleeve 140 assures that the further procedure to be performed will occur coaxial to the disc space D and further, be symmetrical in regard to each of the opposed vertebral surfaces.

Figure 10:
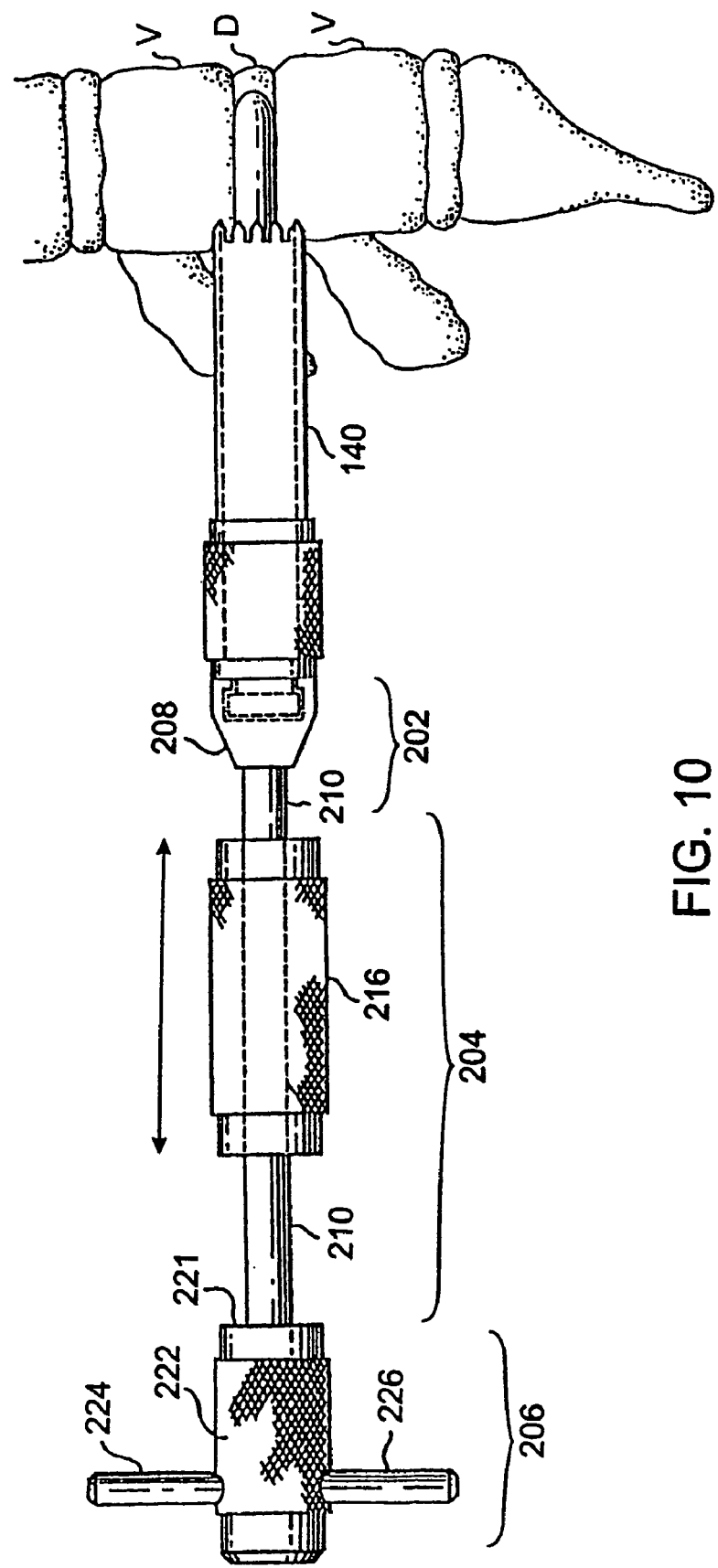
FIG. 10 is a side elevational view of the Proximal Puller engaging the extraction ring of the Long Distractor shown in hidden line over the end of the Outer Sleeve.
Figure 10A:
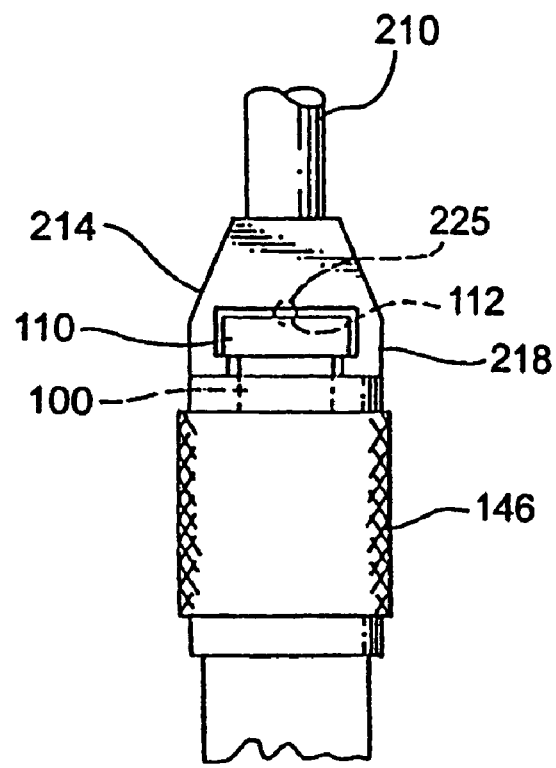
FIG. 10A is a partial side elevational view of the Proximal Puller coupled to the Long Distractor just prior to its extraction.
Figure 10B:
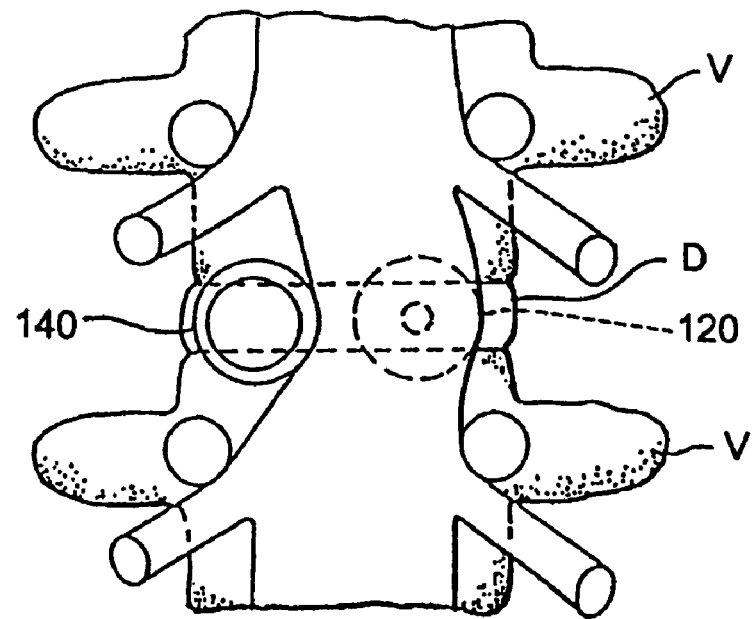
FIG. 10B is a posterior view of the proximal Outer Sleeve and a Short Distractor shown in hidden line in place in regard to the vertebrae, disc and nerves.

Referring to FIG. 10B, a posterior view of the spine at this stage of the procedure, is shown with a Short Distractor 120 in place on one side of the spine and the bottom portion of Outer Sleeve 140 in place on the opposite side of the spine.

Figure 11A:
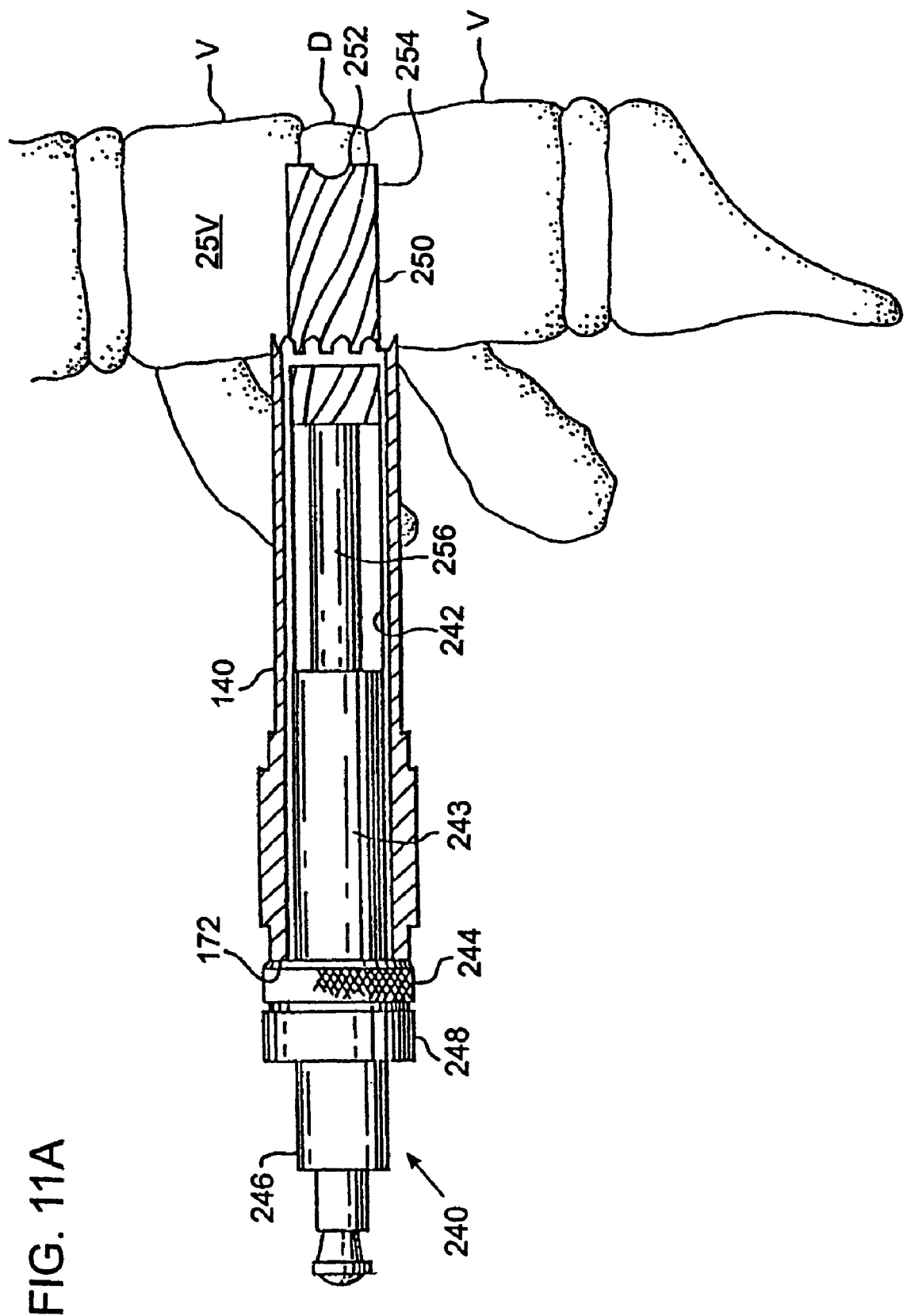
FIG. 11A is a side sectional view of the Drill and Inner Sleeve within the Outer Sleeve drilling across the intervertebral space and cutting partially cylindrical arcs from the adjacent vertebrae.

Referring to FIG. 11A, an Inner Sleeve 242 is inserted from the rear within the Outer Sleeve 140. This Inner Sleeve has a collar portion 244 of a known thickness which seats against the top edge surface 172 of Outer Sleeve 140. The cylindrical barrel portion of Inner Sleeve 242 comes to approximate the posterior aspect of the vertebral bodies interior the Outer Sleeve when fully seated. A Drill 240, having a known selected length is then introduced through the rearward aperture of the Inner Sleeve 242 and utilized to ream out the arcs of bone which it engages from the opposed vertebral endplates as well as any discal material within its path down to its predetermined and limited depth. The Drill 240, has a narrow engagement portion 246, which allows it to be affixed to a drill mechanism which may be either a manual or a power unit. A circumferential collar 248 of an increased diameter serves to limit the depth of penetration of the drill 240 and may be fixed, or lockably adjustable.

Not shown here, but well known to those skilled in the art, are various mechanisms to lockably adjust such instruments as drills. Such mechanisms include, but are not limited to, the use of collets, threaded shafts with lock nuts, and flanges engaging grooves forced therein by either a cap pulled over the flanges or screwed down upon them.

In the preferred embodiment, the forward cutting edge 252 of Drill 240 is a modification of a large fluted drill design such that the end resembles an end cutting mill which may contain any workable number of cutting surfaces, but preferably four or more, and such cutting surfaces being relatively shallow such that the advancement of the instrument occurs more slowly. The outside diameter of the Drill 240 corresponds to the minor diameter of the threaded spinal implant. The Inner Sleeve 242 has an inner diameter slightly greater than that dimension and its outer diameter is slightly smaller than the inside diameter of the Outer Sleeve 140 which has the same outer diameter as the major diameter of the threaded implant.

The drill shaft of drill 240 comprises an upper portion 243, a central recessed portion 256 of a smaller diameter and a lower cutting drill portion 250. The upper portion 243 and lower portion 256 of the drill 240 have the same outside diameter.

The Inner Sleeve 242 serves many functions. First, it provides a more intimate drill guide for drill 240 in the event a smaller diameter hole is to be drilled than that of the inside diameter of the Outer Sleeve 140. Second, since it now guides the Drill, it allows for the Outer Sleeve 140 to have an internal diameter large enough to admit the threaded spinal implant, which is indeed considerably larger in diameter than the Drill 240 itself.

If a larger Outer Sleeve 140 were utilized absent the Inner Sleeve 242, then the Drill 240 would be free to wander within the confines of that greater space and would not reliably make parallel cuts removing equal portions of bone from the adjacent vertebrae V. Further, the bone removal not only needs to be equal, but must be correctly oriented in three dimensions. That is, the path of the Drill 240 must be equally centered within the disc space, parallel the endplates, and parallel to the sagittal axis dissecting the interspace.

A further purpose of the Inner Sleeve 242 is that it may be removed simultaneously with the Drill 240, thereby trapping the debris, both cartilaginous and bony generated during the drilling procedure, which are guided rearward by the large flutes 251 of Drill portion 250, where they are collected around recessed portion 256 between the recessed portion 256 and the inner wall of the Inner Sleeve 242 are there contained therein. Thus, by removing the Drill 240 in conjunction with the Inner Sleeve 242, all of the debris generated by the reaming procedure is safely removed from the spinal canal and wound area.

Further, if the disc tissue in the area to be reamed has been removed previously, as per the preferred method, then the patient's own bone of good quality and useful within the operation will then be contained between the Inner Sleeve 242 and the shaft portion 256. Once away from the surgical wound, this material may be used to load the spinal implant or placed deep within the interspace to participate in the fusion.

The method of actually producing the surgical hole within the spine is variable. As shown in FIG. 11C, in an alternative embodiment Drill end 250 has a forward projecting nipple 260, which itself is bullet-shaped in its leading aspect so as to ease its entrance into the disc space and to urge the vertebrae apart. Nipple 260 is distracting, stabilizing as it resists any tendency of the vertebrae to move together, is self-centering to the Drill portion 250 when working in conjunction with Sleeves 140 and 242, and virtually assures the symmetrical resection of bone from the opposed vertebral surfaces.

Referring to FIG. 11B, the alternative "Trephine Method" referred to earlier in this application is shown. In this alternative, a Long Distractor 100 is left in place after the Outer Sleeve 140 is seated. The Long Distractor 100 in this case differs from the Long Distractor of the preferred embodiment in that its outside diameter of the barrel 106 is of a smaller diameter than in the prior version. This is made necessary because regardless of the method, the hole to be formed corresponds to the minor diameter of the spinal implant. Trephine 270, a hollow, tubular member with sharp cutting teeth 251 at its proximal end, has a wall thickness and since the outside diameter of that trephine 270 must correspond to the root diameter of the implant, then the wall thickness of the trephine 270 must be allowed for by a corresponding reduction in the diameter of the Long Distractor 100.

A further modification of the Long Distractor 100 to the "Trephine Method" would use longitudinal grooves (not shown) along the barrel surface 106 for the purpose of transmitting any debris generated during the cutting procedure, rearward. Since the cutting element is both centered and aligned by the Long Distractor, the use of the Inner Sleeve 242 is not mandatory, but may once again be useful in controlling the path of the debris. To that end, little debris is generated in the "Trephine Method" as the bony arcs are not so much being reamed out and removed as they are simply being cut into the bone where these arcs of bone are left connected at their far ends. Thus, when the Trephining Method has been completed and the Trephine 270 and Inner Sleeve 242 removed, unlike in the preferred embodiment where the hole is drilled out, it remains necessary to remove both the two arcs of bone, and any interposed material. Nevertheless, this is very easily performed by various means, one of which is depicted in FIG. 11D.

Referring to FIG. 11D, Instrument 272 consisting of a shaft 276 attached off-center to the lower surface 273 handle 274 is shown. The shaft 274 terminates in a cutting arm 278. The instrument 272 is inserted through Outer Sleeve 140 where the lower surface 273 of handle 274 abuts the top 172 of the Outer Sleeve 140, both stopping downward motion of instrument 272 and precisely placing the perpendicularly cutting arm 278 of instrument 272 so that as handle portion 274 is rotated, the cutting arm 278 is also rotated, cutting the arcs of bone and liberating them from their last attachments. These portions of bone are then removed utilizing this instrument or a long forceps, and then placed within the implants or otherwise used to participate in the fusion.

Figure 13:
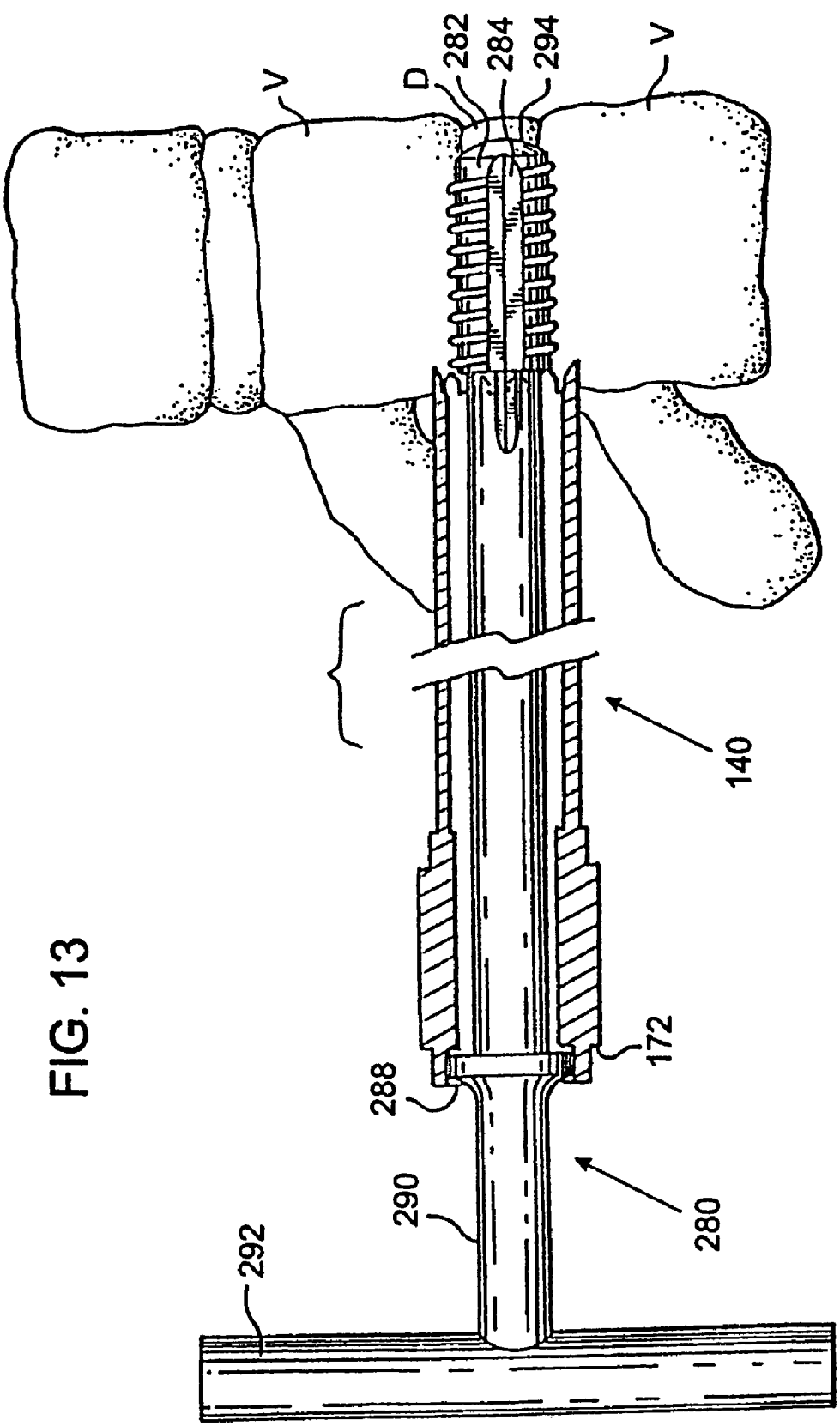
FIG. 13 is a partial sectional side view of the Outer Sleeve and the surgical Tap fully threaded within the interspace.

Referring to FIGS. 12 and 13, while in the preferred embodiment of the present invention the spinal implant I, is essentially self-tapping, if the bone is unusually hard it may be desirable to form the thread pattern within the interspace prior to the insertion of the implant I. To that end, as shown in FIG. 12, Tap 280 has a threadcutting portion 282 connected by a shaft 286 to a handle portion 292, which has been designed to give mechanical advantage to the rotation of the instrument for the purpose of cutting threads. The lower portion of handle 290 has a forward facing flat surface 288 too large to fit through the opening of Outer Sleeve 140 which thus safely limits the depth of penetration of the cutting element 282. This tap 280 is further made safe by blunt end 294 which will engage the uncut portions of the vertebral bone just prior to the engagement of shoulder 288 against surface 172. This feature allows the surgeon to appreciate a less harsh resistance as the blunt nose 294 encounters the remaining unresected bone for the drill hole and prior to the sudden increase in resistance caused by the seating of shoulder 288 against top edge 172, which first resistance serves as a warning to the surgeon to discontinue the tapping procedure. Thus, the surgeon has both visual (as shoulder 288 approaches top edge 172) and tactile warnings to avoid stripping the thread form. Tap end 282 is highly specialized for its specific purpose. Rearward to the specialized blunt tip 294 is a truncated bullet-shaped area 298 which ramps up to the constant diameter intermediate the cutting ridges 296. Ramp portion 298 urges the opposed vertebral bodies apart, which motion is resisted by Outer Sleeve 140, thus progressively driving the sharp leading edges of thread forms 296 into the vertebral bodies. The periodic longitudinal grooves 284 interrupting the thread forms, which may number 1 to 8, but preferably 4, function to accumulate the bony material which is removed during the thread cutting process. In that regard, in the ideal embodiment, the thread cutting form is designed to compress the bone to be formed rather than to trough through it. Further, while both the major and minor diameters of the Tap 280 may be varied, in the preferred embodiment, the minor diameter corresponds to the minor diameter of the implant I, but the major diameter is slightly less than the major diameter of the implant.

With Tap 280 now removed, and Sleeve 140 still in place, the surgical site is now fully prepared to receive the spinal implant I. In the preferred embodiment of the spinal implant, the implant has been enhanced by the use of, application to, and filling with fusion promoting, enhancing, and participating substances and factors. Thus, the implant may be fully prepared for insertion as provided to the operating surgeon. However, at the present time, human bone is most commonly used as the graft material of choice, with the patient's own bone being considered the best source.

Figure 14A:
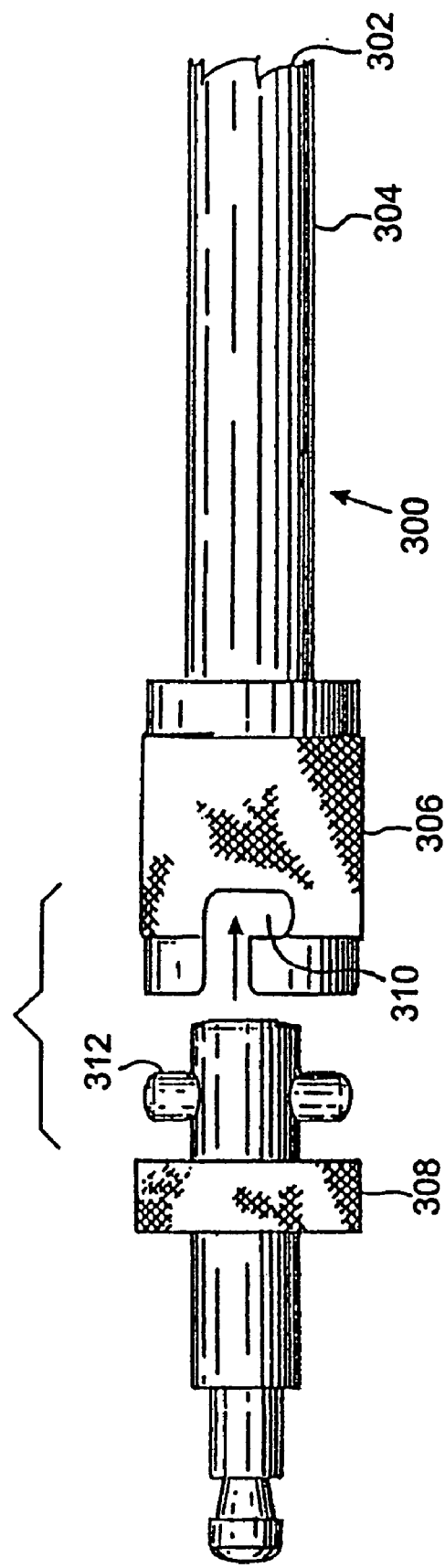
FIG. 14A is a side elevational view of the bone harvesting Trephine and motor adapter.

Referring to FIG. 14A, a trephine 300 is shown with an exceedingly sharp front cutting edge 302 for quickly and cleanly coring into the patient's posterior iliac crest, or any other bony tissue, and for the purpose of producing a core of bone then contained within the hollow 304 of the trephine 300. Trephine 300 has a rear portion 306 with a pair of diametrically opposed slots 310, and disposed clockwise from their longitudinally oriented rearward facing openings so as to engage diametrically and opposing members 312 of Drive unit 308, by which trephine 300 may be attached to either a hand or power drill. It can be appreciated that engagement mechanism 312 is stable during the clockwise cutting procedure, and yet allows for the rapid disconnection of the two components once the cutting is completed.

Because of the high interference between the graft and the inner wall of hollow portion 304, and the relative weakness of the cancellous bone being harvested, it is possible to remove the Trephine 300 while still drilling, and to have it extract the core of bone with it. However, in the highly unlikely event that the core of bone would remain fixed at its base, then with the drive mechanism 308 removed, a corkscrew 408 shown in FIG. 14C is introduced though the central opening of rear portion 306 and threaded down and through the core of bone within 304 and to the depth of teeth 302. The tip 318 of the corkscrew 408, which extends substantially on line with the outer envelope of the corkscrew, then cuts radially through the base of the bone core. As the handle portion 314 of the corkscrew 408 abuts the flat, rearward surface of portion 306 and it can no longer advance. As corkscrew 408 is continued to be turned further, it will cause the core of bone to be pulled rearward, as in removing a cork from a wine bottle. Trephine 300 has a barrel portion 304 continuous with sharp toothed portion 302 having an inner diameter just less than the inner diameter of the spinal implant I to be loaded.

Figure 14B:
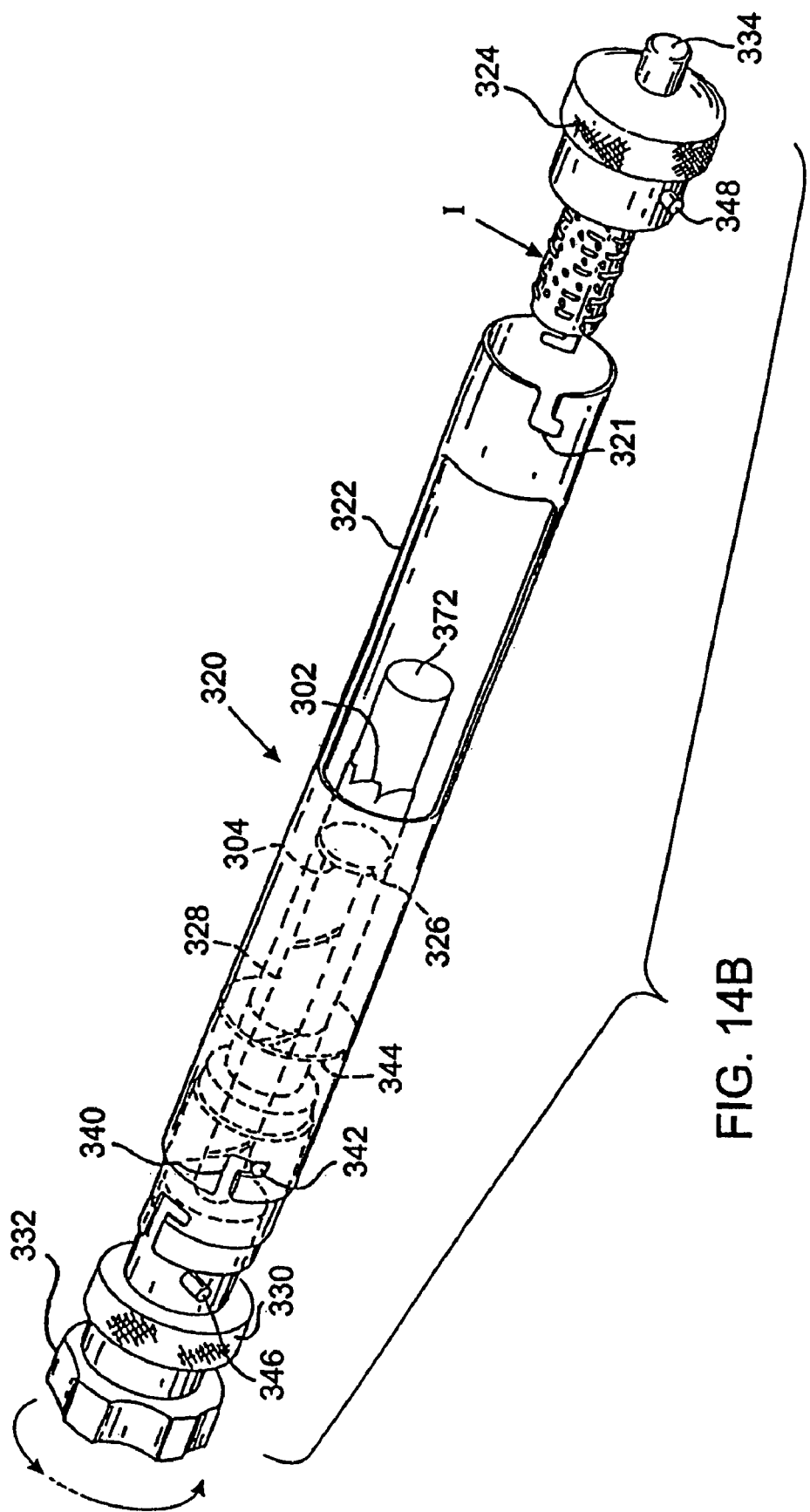
FIG. 14B is a perspective side view of the implant Bone Loading Device.
Figure 14C:
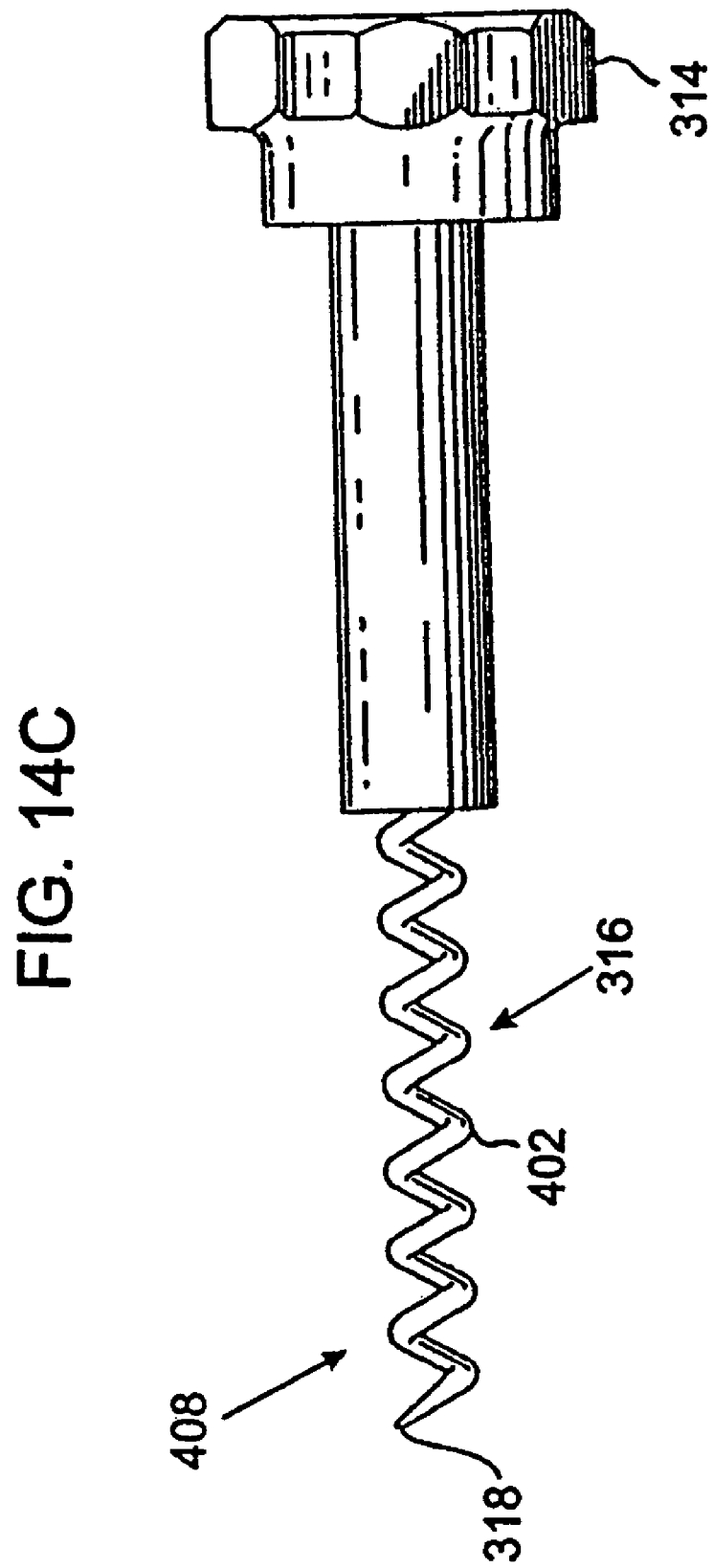
FIG. 14C is a perspective side view of the Corkscrew bone freeing and extracting instrument.

Referring to FIG. 14B, the Trephine 300 with its core of harvested bone is then placed as shown in FIG. 14B, through opening 340 of Implant Bone Loading device 320, where the barrel portion 304 then passes through and is stopped by circular flange 344. The plunger shaft 326 of instrument 320 is then prepared for attachment by rotating knob 332 counterclockwise such that the plunger 372 is pulled via the long threaded shaft portion 328 back to the base of collar 330 at its proximal end. In this position, knob 332 is considerably extended rearward from collar 330. With plunger shaft 326 in this position, the plunger head 372 is inserted into the central hollow of portion 306 of Trephine 300 as the proximal cylindrical portion of collar 330 then follows it, such that the plunger 372 then occupies the rearward portion of barrel 304 and the proximal cylindrical portion of collar 330 occupies the central hollow of portion 306. A pair of diametrically opposed radially projecting arms 346 on collar 330 are then advanced longitudinally into diametrically opposed paired L slots 340 and then rotated clockwise to complete this assembly.

At the other end of instrument 320, a spinal implant I is engaged through its female rectangular slot 364 by a rectangular protruding bar extending from rearward facing surface of end plug 324, (not shown) and secured there by knob 334 which extends as a rod through a central aperture within end plug 324 to extend at the far end as a small bolt which threads to a female aperture centered within the female slot 364 of the spinal implant. With the spinal implant I secured to end plug 324 and the opposite end of the implant I presenting as a hollow, tubular opening, end plug 324 is advanced into device 320 where it is secured by rotationally engaging diametrically opposed L-shaped slots 321. With device 320 fully assembled, end 302 of trephine 300 lies coaxial and opposed to the open end of implant I.

Figure 15:
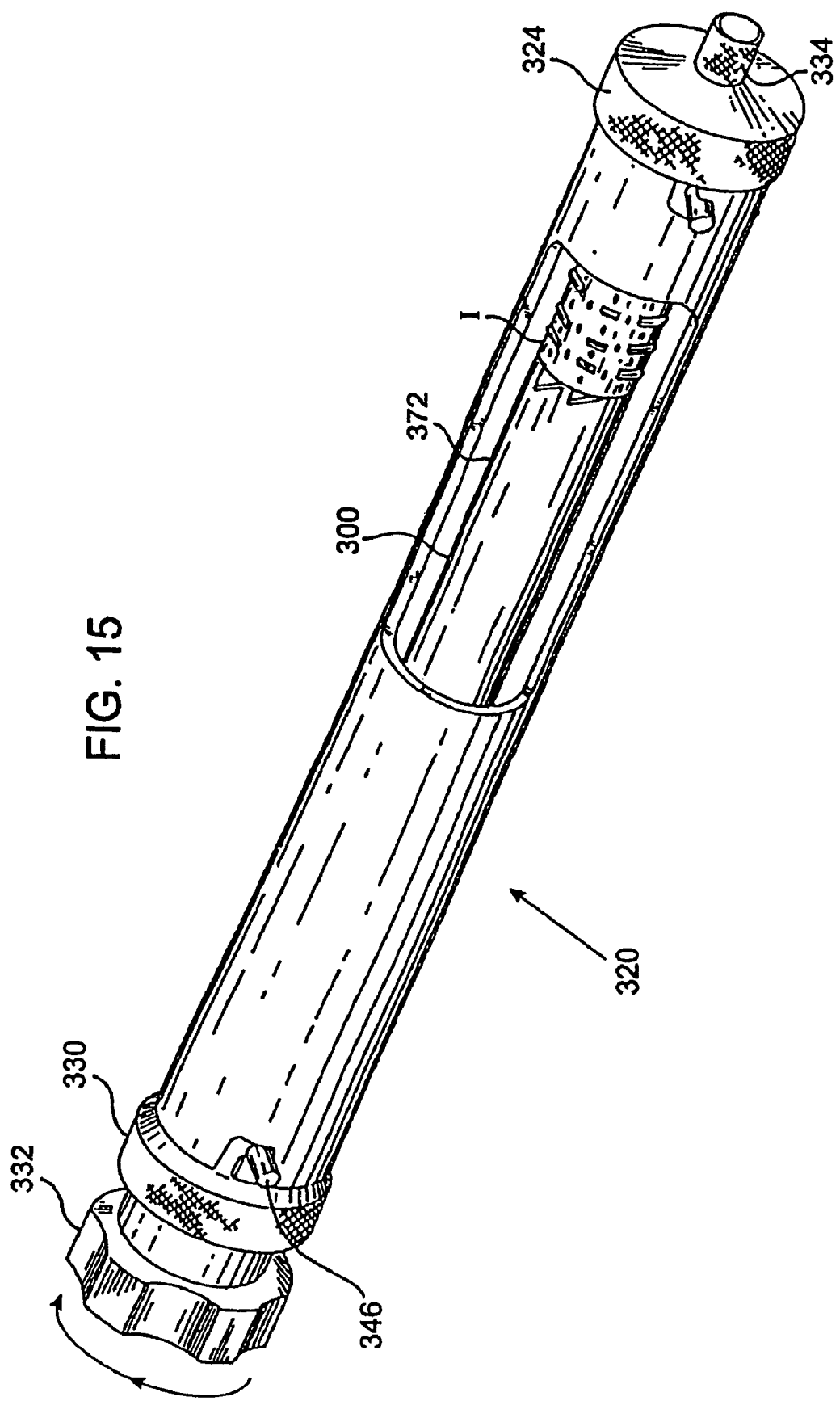
FIG. 15 is a perspective side view of the Bone Loading Device in operation.

Referring to FIG. 15, as knob 332 is then rotated clockwise, the plunger 372 proximal the threaded shaft 328 is then forcibly, but controllably driven forward down the barrel 304 ejecting the bone graft directly into the spinal implant I. As the bone graft is greater in length than the interior of the spinal implant, with further compression the bone is forced into the radially disposed apertures through the wall of the device communicating from the central cavity to the exterior.

Figure 16:
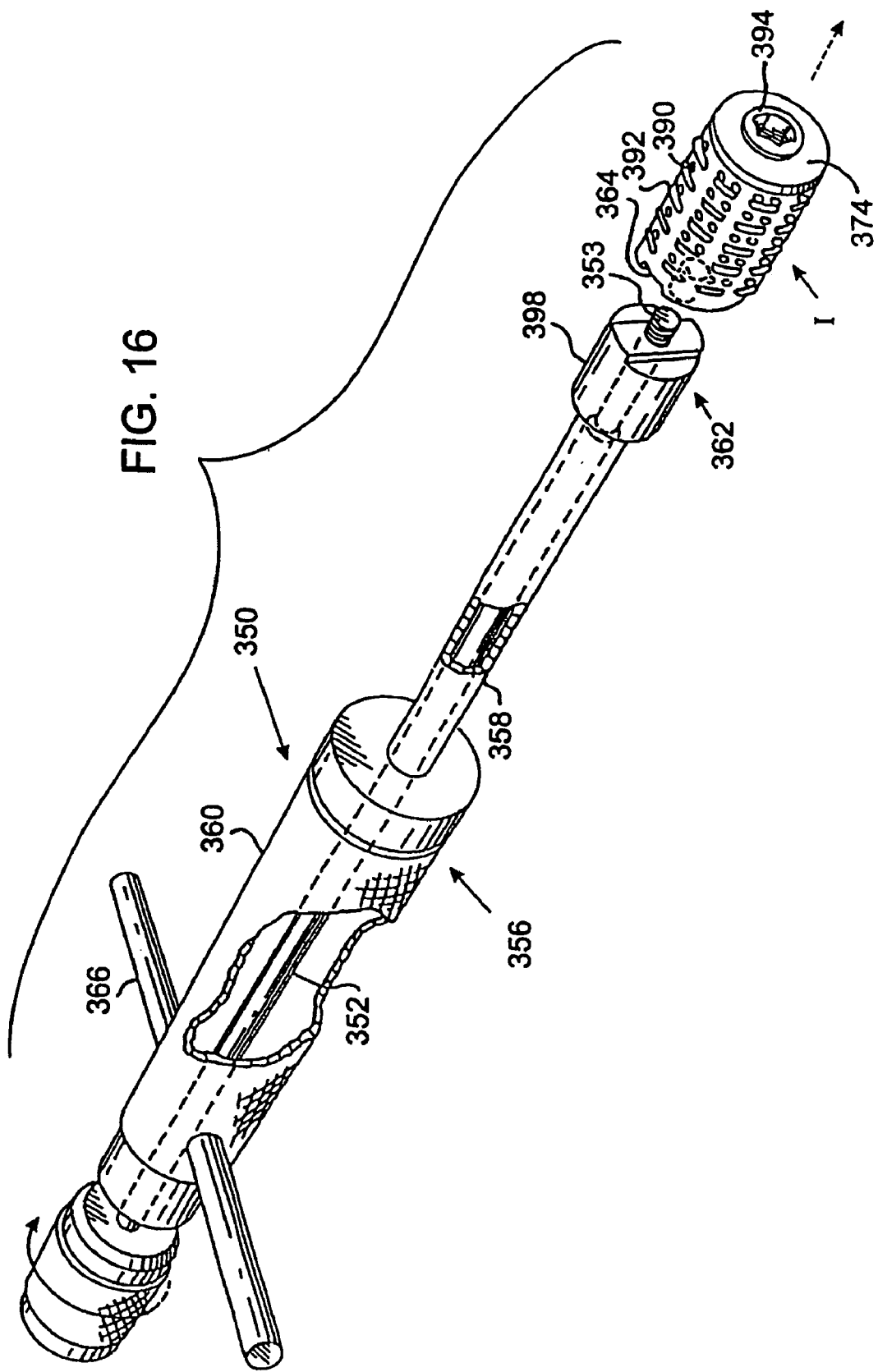
FIG. 16 is a partial sectional perspective side view of the Implant Driver about to engage the spinal implant.

End plug 324 is then removed from apparatus 320. Using end plug 324 as a handle, end cap 374 shown in FIG. 16 is secured to the open end of the spinal implant I. The implant is then disassociated from end plug 324 by rotating knob 334 counterclockwise.

Referring to FIG. 16, an Implant Driver instrument which may be used to either insert or to remove said implant I is shown. Driver 350 has at its far end 362, a rectangular protrusion 398, which protrusion intimately engages the complimentary rectangular slot 364 of implant I. Protruding from slot 398 of end 362 is threaded portion 353, which extends as a rod through hollow shaft 358 and hollow hand barrel 360 to knob 354 where it can be rotationally controlled. Threaded portion 353 screws into a female aperture central slot 364, urging 353 into 364, and binding them together such that instrument 350 can be rotated via paired and diametrically opposed extending arms 366 and in either direction while maintaining contact with the implant.

Figure 17:
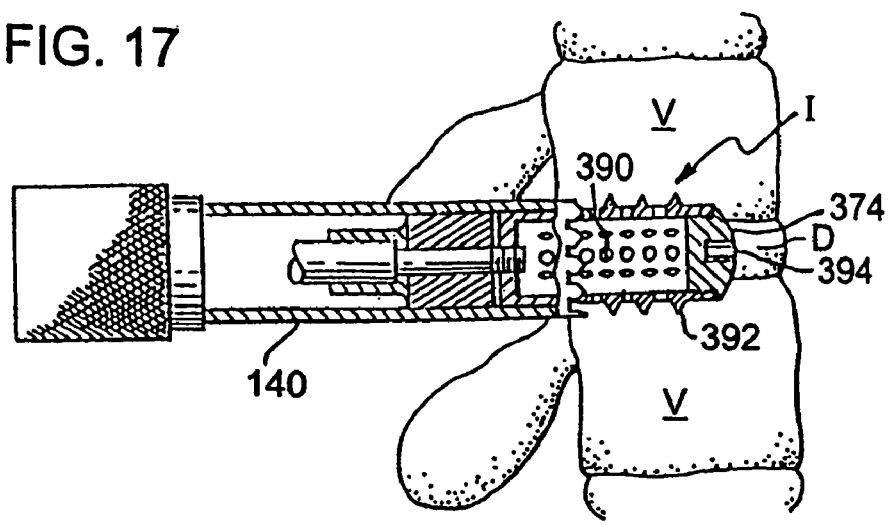
FIG. 17 is a partial sectional side elevational view of the spinal implant being fully seated within the intervertebral space by means of the Driver apparatus in place within the Outer Sleeve.

Referring to FIG. 17, affixed to the Driver 350, the implant I is then introduced through the Outer Sleeve 140 and screwed into the interspace opposed between the two prepared vertebrae V until such time as the leading edge of the Implant Cap 374 reaches the depth of the prepared hole at which time its forward motion is impeded by the bone lying before it which had not been drilled out. This allows for a progressive feel to the surgeon as the implant is screwed home.

As described previously, with the use of the Tap 280, this terminal resistance to further seating provides significant tactile feedback to the surgeon. Again, as with the Tap 280, visual monitoring of the depth of insertion of the implant is provided to the surgeon by observing the progressive approximation of the forward surface 370, of barrel portion 360, as it approaches the rearward facing surface 172 of Outer Sleeve 140. Nevertheless, a final safety mechanism, when the full depth of insertion has been achieved, surface 370 of instrument 350 will abut surface 172 of the Outer Sleeve 140, prohibiting any further installation of the spinal implant.

Figure 18:
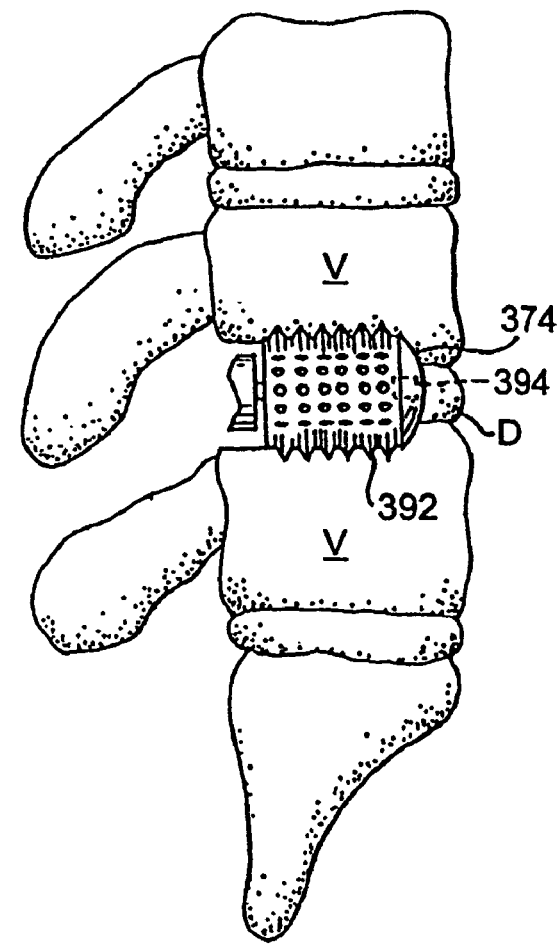
FIG. 18 is a side elevational view of the lumbar spine showing the end result of the spinal implant implantation via the posterior route.

Referring to FIG. 18, once the implant has been fully installed, the Driver 350 is dissociated from the implant I by turning knob 354 in a counterclockwise direction. The Driver 350 is then withdrawn from the Outer Sleeve 140, then the Outer Sleeve 140 is removed. This leaves the implant fully installed and inset to the determined depth as shown in FIG. 18.

Attention is then redirected to the other, or first, side of the spine. A dural nerve root retractor is used to retract the neural structures medially, bringing into full view the head 128 of the Short Distractor 120, lying flush on the canal floor. Utilizing apparatus 152, extended screw portion 116 is inserted into the female threaded portion 114 of the Short Distractor 120 as the extended rectangular portion 134 of apparatus 152 is engaged to the female rectangular portion 118 of the Short Distractor 120. Then turning rearward facing portions 108 and 110, utilizing the knob 136 of FIG. 2, the Long Distractor configuration is restored.

With the dural sac and nerve roots still retracted and protected, the Outer Sleeve 140 is slipped over the reconstituted Long Distractor and seated using the Driver Cap 162. The entire sequence of events as described for the implantation of the spinal implant I as already placed, is then repeated such that both spinal implants come to lie side by side within the interspace. Though not necessary, circlage or other internal fixation of the levels to be fused may additionally be performed, and then the wound is closed in the routine manner.

Brief Discussion with Reference to the Drawings of the Preferred Method and Instrumentation for Anterior Interbody Fusion Incorporating Intercorporeal Predistraction and Utilizing a Guarded Sleeve System is Disclosed Because of the absence of the spinal cord and nerve roots, it is generally possible to visualize in one instance the entire width of the disc space from side to side throughout the cervical, thoracic, or lumbar spine. In the preferred embodiment of the anterior interbody fusion, implants are placed side by side from anterior to posterior parallel to the interspace and extending into the adjacent vertebral bodies. Where the transverse width of the disc space is insufficient to allow for the use of two implants, each of which would be large enough to protrude to the required depth into the adjacent vertebrae, then a singular and significantly larger implant may be placed centrally. With this in mind, and in light of the very detailed description of the technique and instrumentation already provided in regard to the method of posterior lumbar interbody fusion, a brief discussion of anterior spinal interbody fusion with dual implant installation will suffice, and the method for installation of a large, singular midline graft will become obvious.

The interspace to be fused is exposed anteriorly. The soft tissues are withdrawn and protected to either side, and if necessary, above and below as well. It is then possible to visualize the entire width of the vertebrae anteriorly adjacent that interspace. As discussed above, the surgeon has already templated the appropriate patient radiographs to determine the requisite distraction and optimal implant size. In the preferred method, the surgeon then broadly excises the great bulk of the nuclear disc portion. (Alternatively, the disc can be left to be removed via the drill later.) The surgeon then notes and marks a point midway from side to side anteriorly. He then inserts Long Distractor 100 centering it on a point midway between the point just noted and the lateral extent of the intervertebral space visualized anteriorly. The outer barrel portion 106 of the Distractor 100 utilized, will correspond to the outside diameter of the implants to be installed. The Distractor tips 102 inserted are sequentially larger in diameter until the optimal distraction is achieved. This optimal distraction, although suggested by the initial templating, may be visually and tactilely confirmed as performed. When the optimal distraction is achieved, the vertebral endplates will come into full congruence and parallel to the forward shaft portion 102 of the Distractor 100, causing an alteration in the alignment of the vertebrae and a significant increase in the interference fit and pressurization at the tip, such that the instrument becomes exceedingly stable.

There is a sensation imparted to the surgeon of the tissues having moved through their elastic range to the point where the two adjacent vertebrae V begin to feel and move as if a single solid. These changes are easily appreciated visually as the vertebrae realign to become congruent to tip 102, and can also easily be appreciated via lateral Roentgenography. However, should the surgeon fail to appreciate that optimal distraction has been achieved and attempt to further distract the interspace, he would find that extremely difficult to do because of the increased resistance as the tissues are moved beyond their range of elastic deformation. Further, there would be no elasticity left to allow the vertebrae to move further apart and the sensation to the surgeon should he attempt to gently tap the oversized Distractor forward with a mallet, would be one of great brittleness.

Returning now to the procedure, when the correct intercorporeal Long Distractor 100 producing the ideal interspace distraction having its barrel portion 106 corresponding to the implant I to be installed has been inserted, then its exact duplicate is inserted anteriorly equidistant to the other side of the spine. As the barrel portion 106 of Long Distractor 100 is exactly of the same major diameter as the spinal implant I looking coaxially on end, the surgeon can then asses the anticipated side by side relationship of the dual implants when implanted.

Figure 7A:
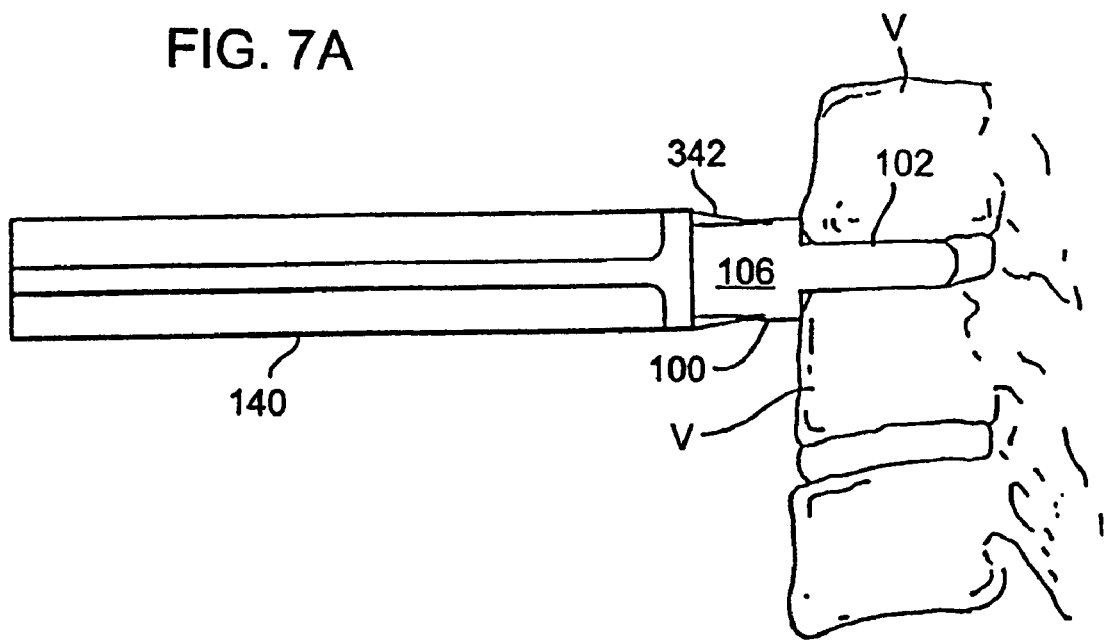
FIG. 7A is a side elevational view of the cervical Outer Sleeve being placed over a Long Distractor which is in place within the disc space anteriorly.
Figure 7B:
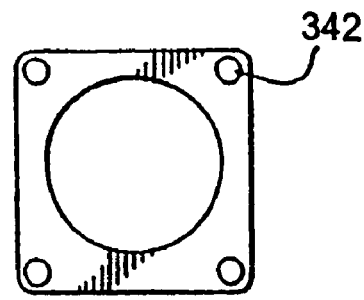
FIG. 7B is a bottom plan view of the single Outer Sleeve of FIG. 7A.
Figure 7C:
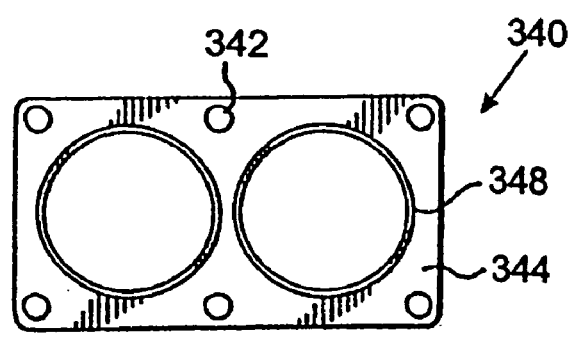
FIG. 7C is a bottom plan view of a Dual Outer Sleeve.
Figure 7D:
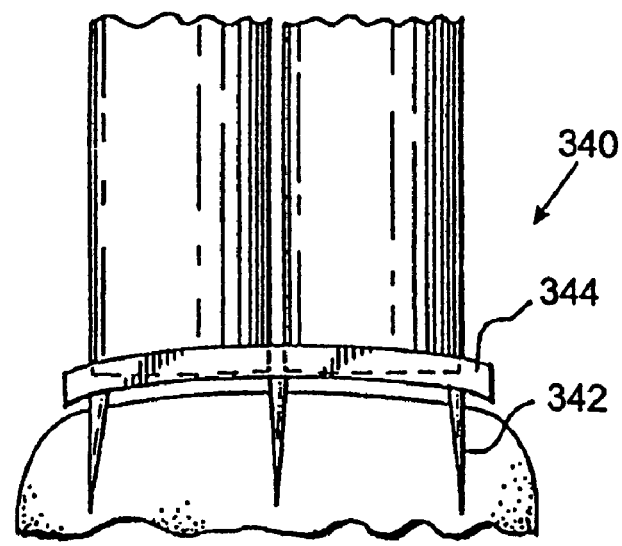
FIG. 7D is a side elevational view of the proximal portion of FIG. 7C.

Referring to FIGS. 7C and 7D, a Dual Outer Sleeve 340 consisting of a pair of hollow tubes is then introduced over the side by side Long Distractors 100 protruding anteriorly from the spine. The Dual Outer Sleeve 340 is comprised of two hollow tubular members identical in size displaced from each other ideally the sum of the difference between the minor and major diameters of both implants combined, but not less than that difference for one implant, as it is possible to have the threads of one implant nest interposed to the threads of the other, such that they both occupy a common area between them. However, while the preferred embodiment is slightly greater than two times the difference between the major and minor diameters of the implant (the sum of both) the distance may be considerably greater. Whereas in the preferred embodiment the paired tubular portions 348 of the Dual Outer Sleeve 340 are parallel, when the area between them 350, is sufficiently great, these elements may be inclined or declined relative to each other such that they either converge or diverge at their proximal ends. The paired tubular portions 348, may be bridged in part or wholly throughout their length, but are rigidly fixed by Foot Plate 344. In its preferred embodiment, a top view shows the Foot Plate 344 to be essentially rectangular, but without sharp corners. However, it is appreciated that other shapes for the Foot Plate 344 can be utilized.

Referring to FIG. 7D, it can be appreciated, that Foot Plate 344 is contoured so as to approximate the shape of the vertebrae anteriorly. Extending forward from Foot Plate 344 are multiple sharp prongs 342 sufficiently long to affix them to the vertebrae. The prongs 342 are limited in length so as to not penetrate too far posteriorly and number from 2 to 10, but preferably 6.

Figure 7E:
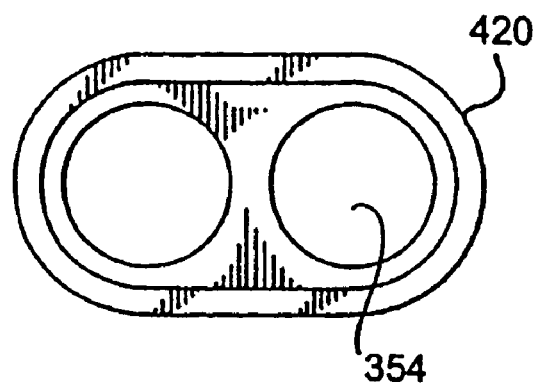
FIG. 7E is a bottom plan view of a Dual Driver Cap for driving two distractors.
Figure 7F:
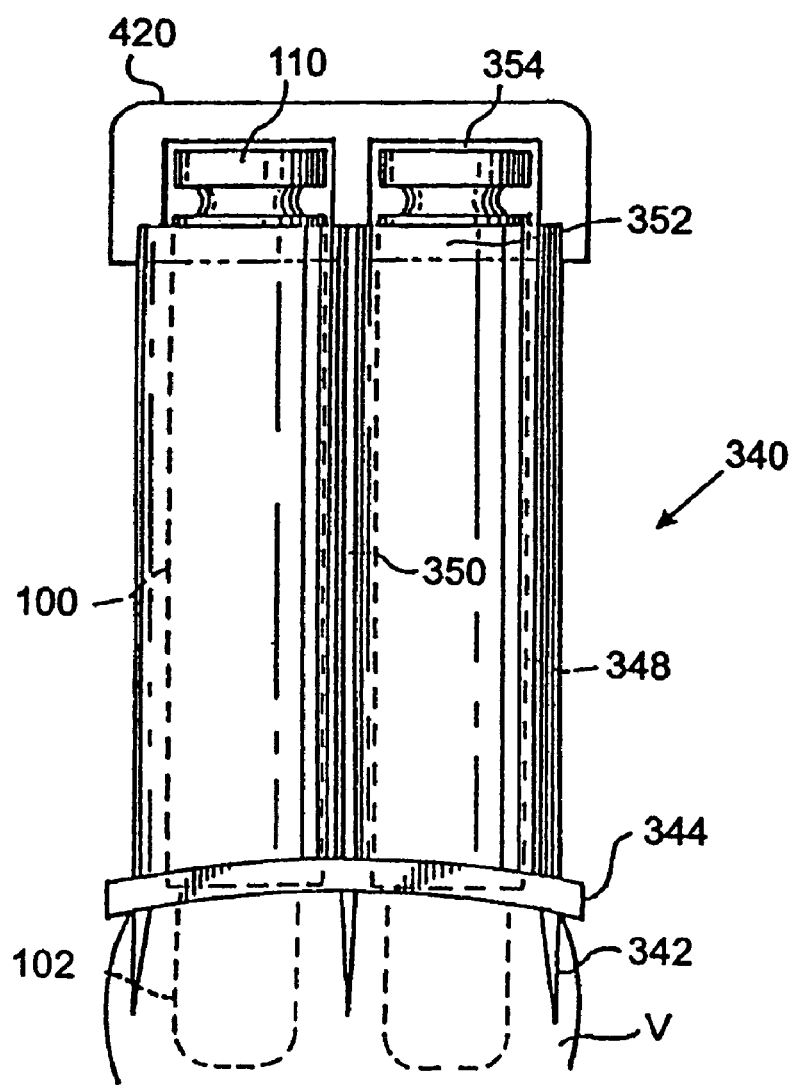
FIG. 7F is a side sectional view showing the Dual Outer Sleeve of FIGS. 7C and 7D, Distractors and Dual Cap of FIG. 7E seated in relation to the vertebrae.

Referring to FIGS. 7E and 7F, as the Dual Outer Sleeve 340 is driven forward utilizing Dual Driver Cap 420, of FIG. 7E, engaging the rearward end 352, the prongs 342 extending from Foot Plate 344 are embedded into the opposed vertebral bodies until their forward motion is inhibited by the curved Foot Plate 344 becoming congruent to and being stopped by, the anterior aspect of the vertebral bodies.

As already shown in FIG. 5, the Dual Driver Cap 420 is of the same design as Single Driver Cap 160, in that there is a recess 354 as per 168, allowing the Outer Sleeve to be fully seated without impeding the rearward projection of the Long Distractor unit. However, unlike in Cap 160, area 354 is more relieved as it is unnecessary for the Dual Cap 420 to contact the Long Distractor through portion 110 to inhibit its forward motion, as the Foot Plate 344 functions to that effect. Further, the Dual Cap 420 for the Dual Outer Sleeve 340 is correspondingly dual itself and engages the rearward facing dual tubular portion 352. Once the Dual Outer Sleeve has been fully seated, the vertebrae adjacent the interspace to be fused are rigidly held via Foot Plate 344 and the prongs 342. Thus, it is possible to remove either one, or if desired, both of the Long Distractor rods utilizing Long Distractor puller 200, as per the method already described. It is then the surgeon's choice to work on one or both sides of the spine. As per previous discussion, the surgeon may drill the interspace utilizing the Inner Sleeve 242 or leave the Long Distractors in place as per the "Trephine Method".

Tapping, if necessary, and the insertion of the implants then occurs through the protective Outer Sleeve 340. Once the implants have been fully inserted, the Outer Sleeve is removed.

Having utilized the Drill method, or "Trephine Method", with or without an Inner Sleeve to prepare the fusion site, it is the preferred embodiment to leave the Outer Sleeve 340 in place as it provides for the ideal placement and alignment of the Tap 280 and implant I.

It is anticipated that the surgeon wishing to work deep within the interspace, or preferring the ability to directly visualize the tap being used, or the implant being inserted, may choose to remove the Outer Sleeve after the insertion of the first prosthesis to maintain stability, or prior to that, which while not the preferred embodiments, are nevertheless within the scope of the present invention.

Alternative Methods to the Preferred Embodiment for Method of Anterior Interbody Fusion As previously described for the posterior lumbar spine, alternatively, one can employ the "Trephine Method" as has been described in detail.

As a further alternative, it should be noted that the key element in the anterior method is the use of the predistraction principle, where such distraction is maintained by the Outer Sleeve with or without the Long Distractor. Therefore, once the preparation of the interspace has been completed, while not the preferred embodiment, it is nevertheless within the scope of this invention that one could remove the Outer Sleeve as there are no neural structures requiring protection, and insert the implants directly rather than through the Outer Sleeve.

As yet a further alternative of this method, where the height of the distracted interspace is such that the diameter of the implant required to span that height and to embed with sufficient depth into the opposed vertebral bodies is such that it is not possible to place two such implants side by side, then only a single implant which may be of significantly increased diameter, is used and placed centrally within the interspace rather than to either side. The placement of a singular central graft via the present invention method and instrumentation is in keeping with the methods already described and can be performed using either a drill or the "Trephine Method".

Referring to FIGS. 16-18, a cylindrical embodiment of the spinal implant I of the present invention is shown. In FIG. 16 the implant I is shown attached to the insertion device 350. In FIGS. 17 and 18 the implant I is shown installed in the disc space D, between the adjacent vertebrae.

The cylindrical implant I comprises a hollow tubular member which in the preferred embodiment is made of an ASTM surgically implantable material, preferably titanium. The cylindrical implant I is closed at one end and open at the other end covered by a cap 394. The cylindrical implant I has a series of macro-sized openings 390 through the side walls of the cylindrical implant I. A series of external threads 392 are formed on the circumference of the cylindrical implant I. Any variety of threads may be used on the implant. The cap 374 has a hexagonal opening 394 for tightening the cap 374.

While the present invention has been described with respect to the preferred embodiment of the method and instrumentation, it is appreciated that other embodiments of the method and instrumentation may be devised without departing from the scope of the present invention. Examples of further embodiments of the present invention are described in detail below.

Detailed Description of Alternative Embodiments of Apparatus and Method

When the human spine is viewed from the side, it consists of a balanced series of curves, as opposed to the vertebrae being stacked one upon another in a straight line when viewed from the side. In both the cervical and lumbar regions of the spine, the vertebrae relate to each other so as to form curves where the apex of said curves is displaced forward within the body, and those segments of the spine are said to be in lordosis. In contradistinction, in the thoracic portion of the spine, the vertebrae relate to each other so as to form a curve where the apex of said curve is displaced posteriorly and is said to be in kyphosis. The methods and instrumentation of the present invention have as one of its purposes to provide for the permanent stabilization of contiguous vertebrae by fusion, there is then a need for a means to preserve said lordosis/kyphosis if present, or to restore said lordosis/kyphosis if already lost, prior to the completion of the fusion procedure.

The following embodiments of the present invention, either individually or in combination, provide for both the stabilization and fusion to be performed with the related vertebrae in the correct anatomic lordosis or kyphosis. Where it is possible to approach the spine from various angles each of the devices, then has different forms appropriate to that specific approach.

Figure 19:
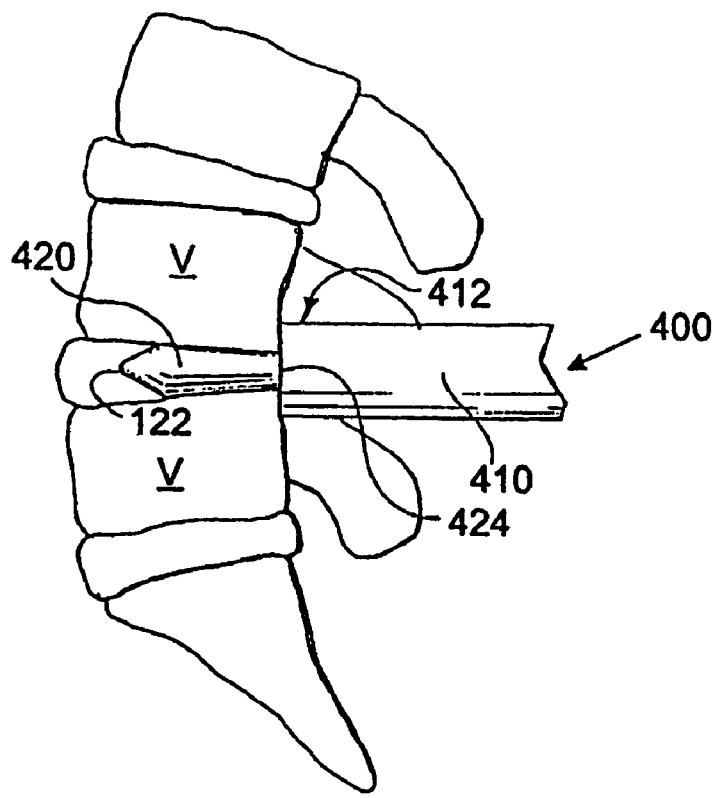
FIG. 19 is a side elevational view of a Posterior Long Lordotic Distractor inserted from the posterior aspect of the spine between adjacent vertebrae to restore and maintain lordosis of the spine.

Referring to FIG. 19, an alternative embodiment of the instrumentation of the present invention comprising a Posterior Long Lordotic Distractor 400 capable of restoring and maintaining lordosis of adjacent vertebrae V from the posterior approach of the spine is shown. The Posterior Long Lordotic Distractor 400 is inserted from the posterior aspect of the spine and comprises a barrel portion 410 terminating at its distal end 412 in a disc penetrating portion 420 which is shown interposed within the disc space between two adjacent vertebrae V. The disc penetrating portion 420 terminates distally into a leading bullet-shaped front end 422 which facilitates the insertion of the disc penetrating portion 420 between the adjacent vertebrae V. The disc penetrating portion 420 is configured to have an uneven diameter such that it has a lesser diameter, and thus a lesser height within the disc space proximate the distal end 412 of the barrel portion 410 and has a greater diameter, and thus greater height within the disc space, in the direction of the front end 422. This configuration of the disc penetrating portion 420 serves to not only restore the intervertebral disc space height upon insertion of the disc penetrating portion 420 of the Posterior Long Lordotic Distractor 400, but also serves to restore and maintain the normal lordosis between the adjacent vertebrae V. The leading bullet-shaped front end 422 is of particular importance in regard to the Posterior Long Lordotic Distractor 400 where the largest diameter portion of the disc penetrating portion 420 would otherwise be entering the disc space first.

The widest diameter of the disc penetrating portion 420 is less than the diameter of the barrel portion 410, such that a circumferential shoulder 424 is formed at the distal end 412 of the barrel portion 410 which prevents over penetration into the disc space of the Posterior Long Lordotic Distractor 400. It can readily be appreciated that such a configuration of the disc penetrating portion 420 renders the Posterior Long Distractor 400 quite stable within the disc space and resistant to backing out as the compressive forces of the spine upon the disc penetrating portion 420 tend to urge it forward, while simultaneously the circumferential shoulder 424 makes such further motion impossible, thus making the Posterior Long Distractor 400 exceedingly stable.

Figure 20:
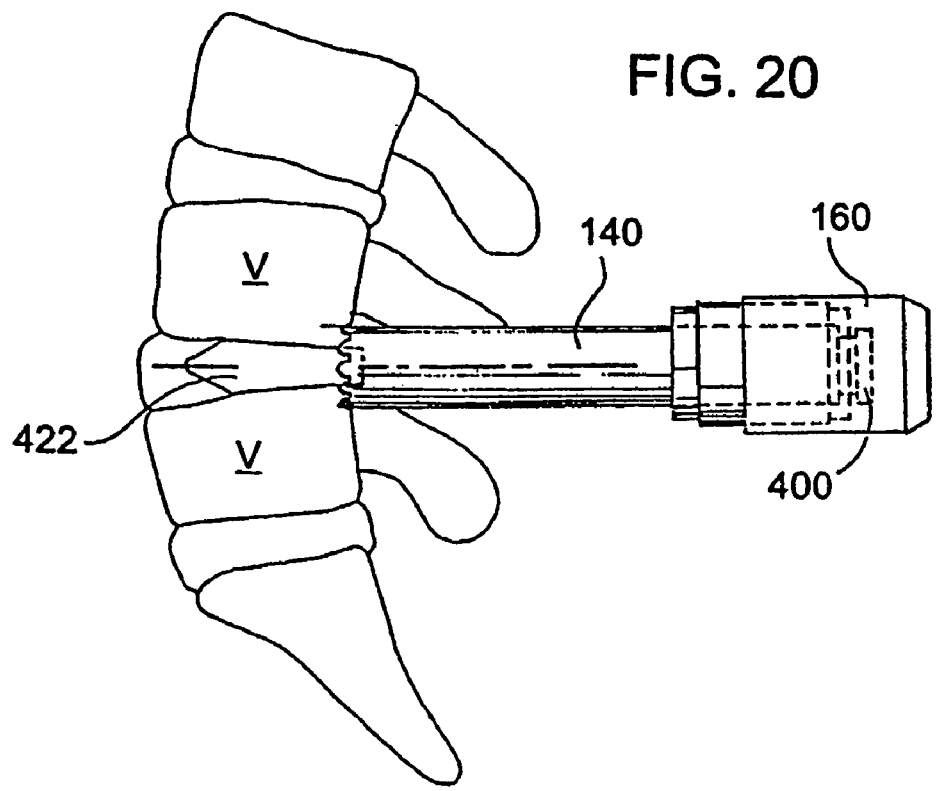
FIG. 20 is a side elevational view of the Posterior Long Lordotic Distractor shown partially in hidden line with the Outer Sleeve and Cap, inserted between adjacent vertebrae to restore and maintain lordosis of the spine with the Outer Sleeve engaging the vertebrae and properly seated over the Posterior Long Lordotic Distractor.

Referring to FIG. 20, in preparation for the bone removal step, the Posterior Long Lordotic Distractor 400 is shown with the disc penetrating portion 420 in place between the adjacent vertebrae V to restore and maintain lordosis of the spine. An Outer Sleeve 140 described above in reference to FIG. 5, is properly seated over the Posterior Long Lordotic Distractor 400 using a mallet and the already described Driver Cap 160. While the bone removal step may be performed by either the drilling method described above in reference to FIGS. 11A and 11C or the "Trephine Method" described above in reference to FIG. 11B, the "Trephine Method" is preferred in this situation as it leaves the Posterior Long Lordotic Distractor 400 undisturbed until sufficient space has been created by the removal of bone at least as great as the thickness of the wall of the trephine 270 itself to allow for the unobstructed removal of the Posterior Long Lordotic Distractor 400.

If the "Trephine Method" described above in reference to FIG. 11B is used with the Posterior Long Lordotic Distractor 400 the Outer Sleeve 140 would first be fitted with an Inner Sleeve 242 such as that shown in FIG. 11B, prior to both being placed simultaneously down over the barrel portion 410 of the Posterior Long Lordotic Distractor 400. Once the Outer Sleeve 140 is concentrically seated relative to the barrel portion 410, the Inner Sleeve 242 alone would be removed, and the trephine 270 would then be placed over the Posterior Long Lordotic Distractor 400 and within the confines of the Outer Sleeve 140 and into the adjacent vertebrae V across the disc space to the appropriate depth. The use of an Inner Sleeve is not required as the trephine 270 is both centered and aligned by the Posterior Long Lordotic Distractor 400.

In addition to cutting the two hemi-cylinders of bone, one for each vertebrae V, the saw-like sharp cutting teeth 271 of the trephine 270 shown in FIG. 11B removes a path of bone equal to the distance of the splaying out of each of the cutting teeth 271 relative to its neighbor and which distance cannot be less than the wall thickness of the trephine 270 itself. Thus, once the trephine 270 is removed, left behind is a semi-cylindrical space outlining each of the arcs of bone cut from the adjacent vertebrae V such that the two spaces combined provide for sufficient space such that it is then possible to extract the Posterior Long Lordotic Distractor 400 without disturbing the vertebrae V themselves as the vertebrae V are held in position by the Outer Sleeve 140 which engages both of the vertebrae V.

Figure 21:
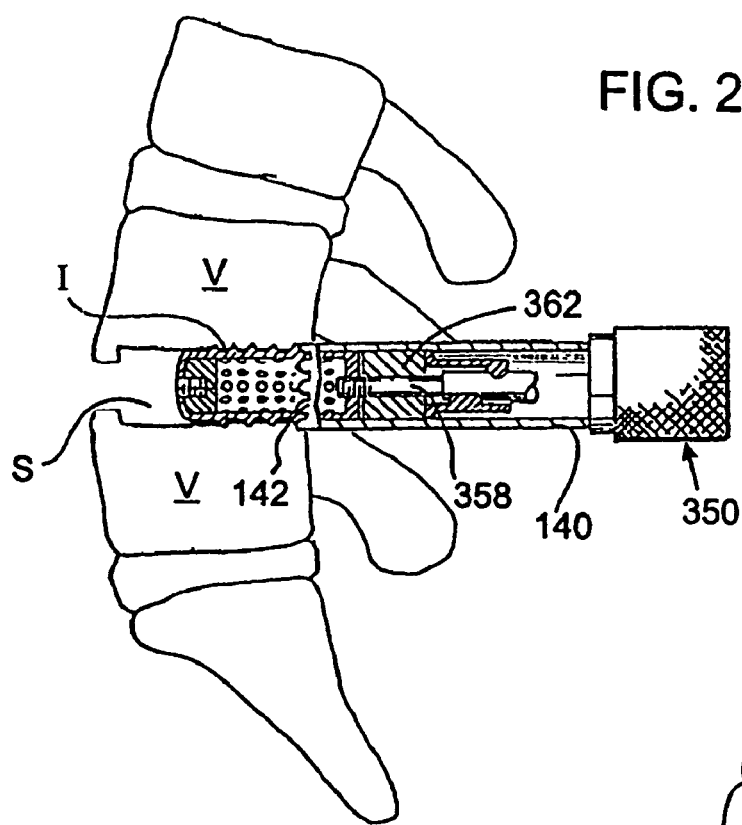
FIG. 21 is a side elevational view partially in cross section of a spinal implant being inserted through an Outer Sleeve between two adjacent vertebrae of the spine in which lordosis has been restored and maintained and in which a portion of bone has been removed from each vertebrae for receiving the spinal fusion implant.
Figure 22:
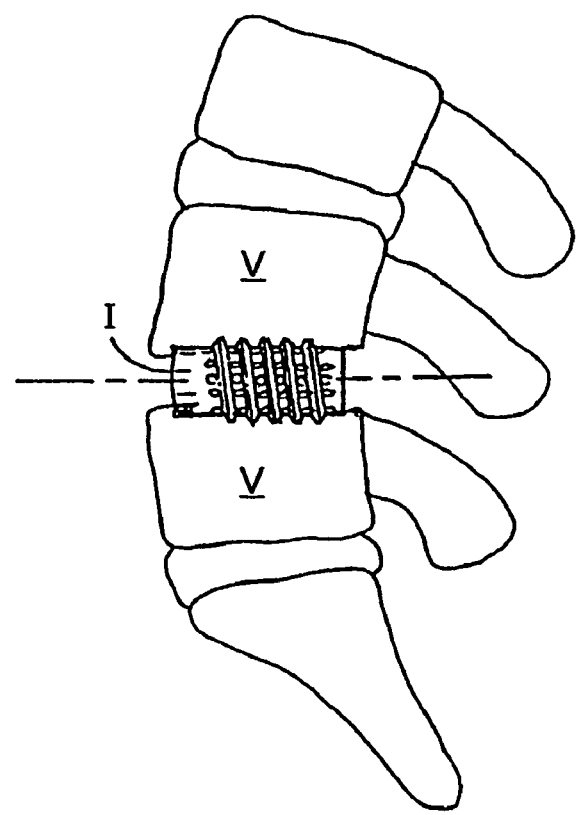
FIG. 22 is a side elevational view of a spinal implant inserted between two adjacent vertebrae of the spine in which lordosis has been restored.

Referring to FIGS. 21 and 22, since the vertebrae V are placed into lordosis prior to the bone removal step, the space S created by the bone removal is cut at an angle relative to the vertebrae V in the shape of a cylinder, and which corresponds to the shape of the cylindrical implant I. In this manner, the cylindrical implant I with parallel walls may be inserted between adjacent vertebrae V which have been stabilized for fusion in angular relationship to each other so as to preserve the normal curvature of the spine.

Figure 23:
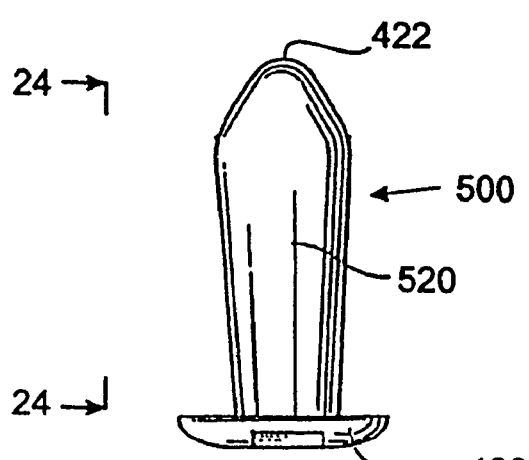
FIG. 23 is a side elevational view of a Posterior Short Lordotic Distractor of the present invention.
Figure 24:
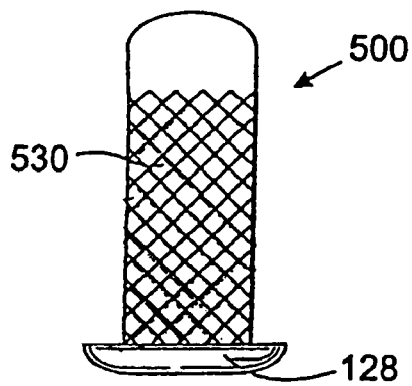
FIG. 24 is a top plan view along lines 24-24 of FIG. 23 of the Posterior Short Lordotic Distractor of the present invention.

Referring to FIGS. 23 and 24, an elevational side view and a top plan view, respectively, of a Posterior Short Lordotic Distractor 500 for posterior use generally referred to by the numeral 500 is shown. The Posterior Short Lordotic Distractor 500 is similar to the Short Distractor 120 described above in reference to the Convertible Distractor and comprises a disc penetrating portion 520 identical to that of the Posterior Long Lordotic Distractor 400 and an increased diameter head 128 as described above in reference to FIGS. 3-3F. As discussed above for the Posterior Long Distractor 400, the configuration of the disc penetrating portion 520 renders the Posterior Short Lordotic Distractor 500 quite stable. This is an especially important feature for the Posterior Short Lordotic Distractor 500 because it is left under the delicate dural sac and nerves while work is being performed on the contralateral side of the spine. If the Posterior Short Lordotic Distractor 500 were other than stable, injury to these structures might result. To further prevent unwanted backing out of the Posterior Short Lordotic Distractor 500, the bone engaging surface 530 may be knurled or otherwise roughened, or have forward facing ratchetings.

Figure 25:
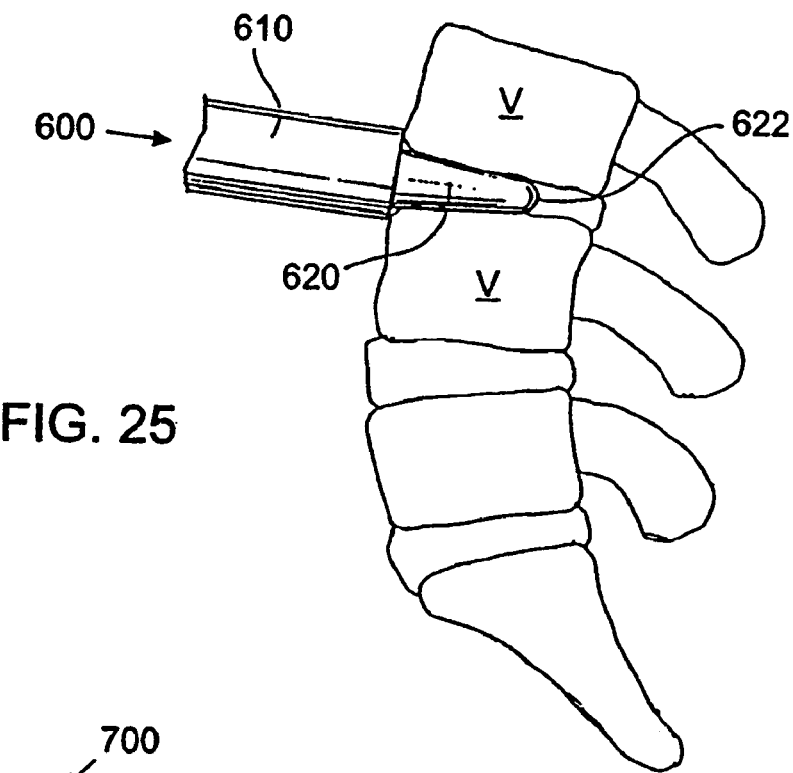
FIG. 25 is a side elevational view of an Anterior Long Lordotic Distractor of the present invention shown inserted between two adjacent vertebrae from the anterior aspect of the spine to restore and maintain lordosis.

Referring to FIG. 25, an Anterior Long Lordotic Distractor 600 for use anteriorly within the spine is shown. It can be seen that the configuration of the disc penetrating portion 620 is the reverse of the disc penetrating portion 420 of the Posterior Long Lordotic Distractor 400 in that the disc penetrating portion 620 is of greatest diameter and height proximate the barrel portion 610 and that the diameter and height are diminished more distally in the direction towards the front end 622 along the disc penetrating portion 620. The Anterior Long Lordotic Distractor 600 serves to restore and maintain lordosis of the spine by distraction of the adjacent vertebrae V. As described above for the Posterior Short Lordotic distractor 500, it is appreciated that an Anterior Short Lordotic Distractor (not shown) having a disc penetrating portion 520 may be similarly devised.

It can be seen that all of the lordotic distractors, both the anterior and the posterior embodiments, have specialized leading bullet-shaped or nosecone-shaped portions so as to facilitate the insertion of the disc penetrating portions within the disc space. This is of particular importance in regard to the Posterior Lordotic Distractors where the largest diameter portion of the disc penetrating portion 420 would otherwise be entering the disc space first.

Figure 26:
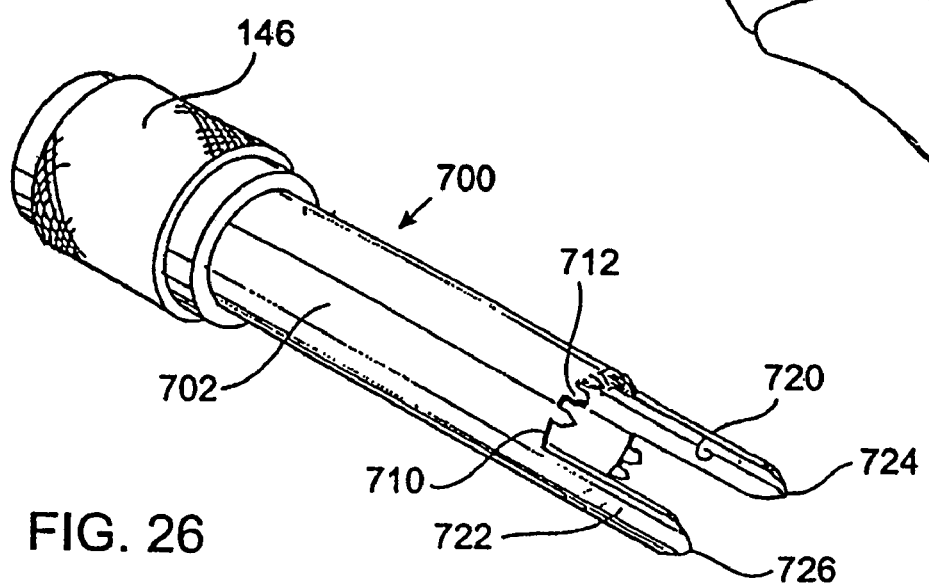
FIG. 26 is a perspective side view of the Extended Outer Sleeve of the present invention having extended members for insertion within the disc space and engaging means for engaging adjacent vertebrae of the spine.

Referring to FIGS. 26 and 27, an alternative embodiment of the present invention for maintaining distraction during the surgical procedure involves a more specialized form of the previously described Outer Sleeve 140 and is shown and identified as the Extended Outer Sleeve 700. The Extended Outer Sleeve 700 comprises a hollow tubular member 702 having a distal end 710 which has been extended such that a pair of extended portions 720 and 722, which are essentially a continuation of the hollow tubular member 702 itself (with or without reinforcement), are opposed 180 degrees from each other, tapered at their leading edges 724 and 726 for ease of introduction, and of such height as to restore the height of the intervertebral disc space. Located at the distal end 710 may be a plurality of teeth 712, similar to those previously described above, or other engagement means for engaging the bone of the adjacent vertebrae V. It appreciated that the distal end 710 may have no teeth 712.

The Extended Outer Sleeve 700 is entirely a new invention such as has never existed in the art or science of surgery, the Extended Outer Sleeve 700 offers numerous advantages over all previously described drilling sleeves and the Outer Sleeve 140 herein previously described. The Extended Outer Sleeve 700 by dint of its extended portions 720 and 722 which are inserted between the adjacent vertebrae does itself act as an intervertebral distractor and is therefore essentially a combination outer sleeve and distractor. The Extended Outer Sleeve 700 is exceedingly stable as the extended portions 720 and 722 are trapped within the disc space and further held there by the considerable compressive loads within the spine.

Referring to FIG. 28, because of the stability thus provided, a further derivative advantage is that the teeth 772 on the distal end 710 of the Extended Outer Sleeve 700' may either be eliminated as shown in FIG. 28, or in the preferred embodiment be made of a lesser size. Further, it should be noted that teeth 712 when present would be confined to the area directly in line with the vertebrae V and the extended portions 720 and 722 would ensure the proper rotatory alignment.

A further advantage, to be discussed in more detail subsequently, is that the extended portions 720 and 722 confine the surgery to the area within and between the extended portions 720 and 722 and protect all other tissues external to the extended portions 720 and 722.

Having now described the novel concept of the Extended Outer Sleeve 700, attention may now be directed to further variations of the Extended Outer Sleeve 700 capable of not only restoring and maintaining the appropriate intervertebral disc space height, but additionally being able to restore and maintain anatomic lordosis or kyphosis, as desired, throughout the surgical procedure.

Referring to FIG. 29, a Posterior Lordotic Extended Outer Sleeve 800 for use from the posterior approach of the spine is shown. The Posterior Lordotic Extended Outer Sleeve 800 comprises a hollow tubular member 802 having a distal end 810 which has been extended such that a pair of extended portions 820 and 822, which are essentially a continuation of the tubular member 802, are opposed 180 degrees from each other. The extended portions 820 and 822 differ from the extended portions 720 and 722 in that the extended portions 820 and 822 are configured to restore and maintain lordosis of the spine similar to the disc penetrating portion 420 of the Posterior Long Lordotic Distractor 400, the features of which are herein incorporated by reference.

The extended portions 820 and 822 each have a height that is lesser at a point proximate the distal end 810 of the tubular member 802 that increases in the direction away from the tubular member 802. The extended portions 820 and 822 are tapered at their leading edges 824 and 826, respectively to facilitate insertion into the disc space.

Between the extended portions 820 and 822, may be a plurality of teeth 812 for engaging the bone of the vertebrae V when the Extended Outer Sleeve 800 is inserted within the disc space between the adjacent vertebrae V.

Referring to FIG. 30, a Posterior Lordotic Extended Outer Sleeve 800' in place within the intervertebral disc space is shown.

Referring to FIG. 31, an Anterior Extended Outer Sleeve 900 for use from the anterior approach of the spine is shown. The Anterior Lordotic Extended Outer Sleeve 900 comprises a hollow tubular member 902 having a distal end 910 which has been extended such that a pair of extended portions 920 and 922 which are essentially a continuation of the tubular member 902 and are opposed 180 degrees from each other. The extended portions 920 and 922 differ from the extended portions 820 and 822 in that the extended portions 920 and 922 are configured to restore and maintain lordosis of the spine from the anterior approach similar to the disc penetrating portion 620 of the Anterior Long Lordotic Distractor 600, the features of which are herein incorporated by reference.

The extended portions 920 and 922 each have a height that is greater at a point proximate to the distal end 910 of the tubular member 902 that decreases in the direction away from the tubular member 902. The extended portions 920 and 922 are tapered at their leading edges 924 and 926, respectively to facilitate insertion into the disc space.

While the Lordotic Extended Outer Sleeve for use anteriorly is shown in the singular form and in use in the lumbar spine, it is understood that it may take a double barrelled form and in either form, be used throughout the spine.

Figure 33:
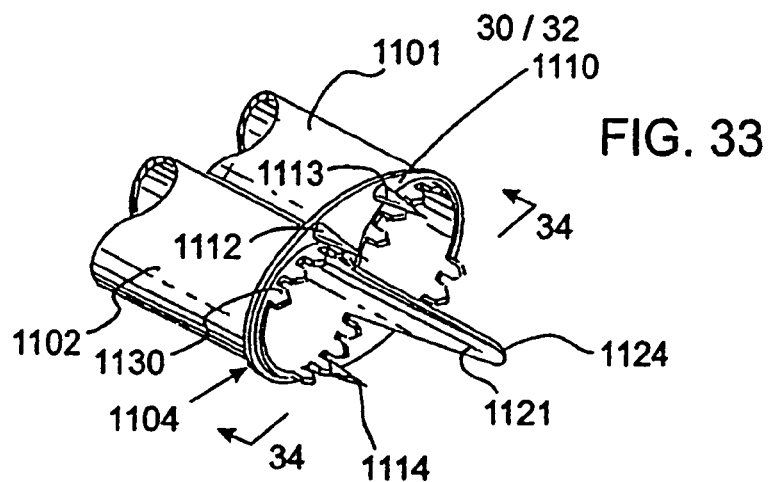
FIG. 33 is a perspective side view of a Dual Extended Outer Sleeve having an uneven extended portion which decreases in height in the direction of insertion.
Figure 34:
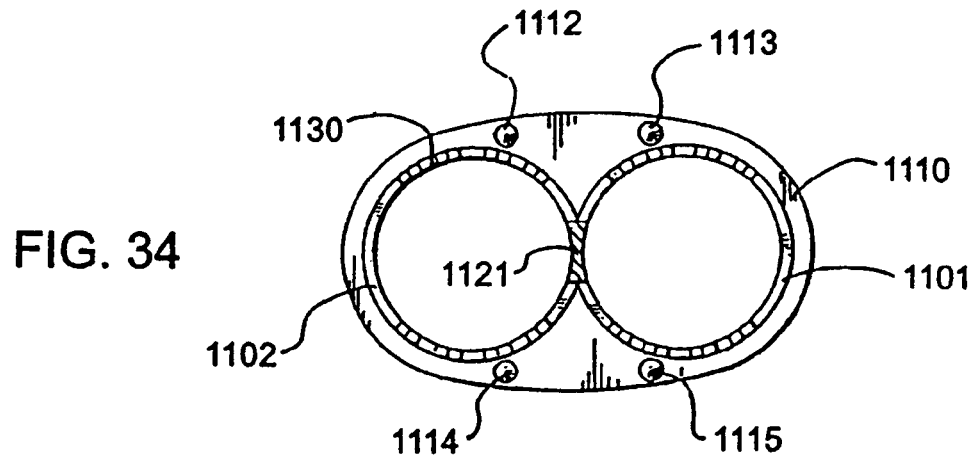
FIG. 34 is bottom plan view of the foot plate of the Dual Extended Outer Sleeve of FIG. 33.

Referring to FIGS. 33 and 34, a Lumbar Dual Extended Outer Sleeve is shown and generally referred to by the numeral 1100. The Dual Extended Outer Sleeve 1100 comprises two hollow tubular members 1101 and 1102. The two hollow tubular members 1101 and 1102 have a distal end 1104 which has been extended to form an extended portion 1121 which is essentially a continuation of the hollow tubular members 1101 and 1102 joined together. The extended portion 1121 is similar in shape and function to the extended portions 920 and 922 described above in reference to FIG. 31. The extended portion 1121 has a height that is greater at a point proximate the distal end 1104 and decreases in the direction away from the hollow tubular members 1101 and 1102, in order to maintain the normal curvature of the spine by correcting the angular relationships of the vertebrae V. The extended portion 1121, is tapered at its leading edge 1124 to facilitate insertion of the extended portion 1121 into the disc space between two adjacent vertebrae V. Located at the distal end of the tubular members 1101 and 1102 are sharpened teeth 1130 for engaging the vertebrae V.

Each of the hollow tubular members 1101 and 1102 are displaced from each other ideally the sum of the difference between the minor and major diameters of two threaded spinal implants I combined, but not less than that difference for one implant I, as it is possible to have the threads of one implant I nest interposed to the threads of the other implant I such that they both occupy a common area between them. Typically, the walls of each hollow tubular members 1101 and 1102 have a combined thickness at the point which the walls of the hollow tubular members 1101 and 1102 are in contact with each other which is approximately 2.0 mm. This is achieved by machining away part of each hollow tubular member 1101 and 1102 to reduce the wall thickness of each hollow tubular member 1101 and 1102 prior to joining them together. In this manner, the two hollow tubular members 1101 and 1102 may be placed closer together so that two spinal implants I may be placed closer together when inserted within the disc space between adjacent vertebrae W. The hollow tubular member 1101 and 1102 can be overlapped or displaced from each other so as to control the distance between implants when the Dual Extended Outer Sleeve is utilized and two implants implanted The hollow tubular members 1101 and 1102 may be bridged in part or wholly throughout their length, but are typically fixed by a foot plate 1110, similar in function, but not in configuration, to Foot Plate 344 described above in reference to FIGS. 7C and 7D.

Referring specifically to FIG. 34, the foot plate 1110 has an oval configuration that contours and hugs the vertebrae and has a plurality of prongs 1112-1115 extending from the bottom of the foot plate 1110 is shown. The prongs 1112-1115 are sufficiently long to engage the bone of adjacent vertebrae V, but limited in length so as not to over penetrate beyond the vertebrae once inserted.

Figure 35:
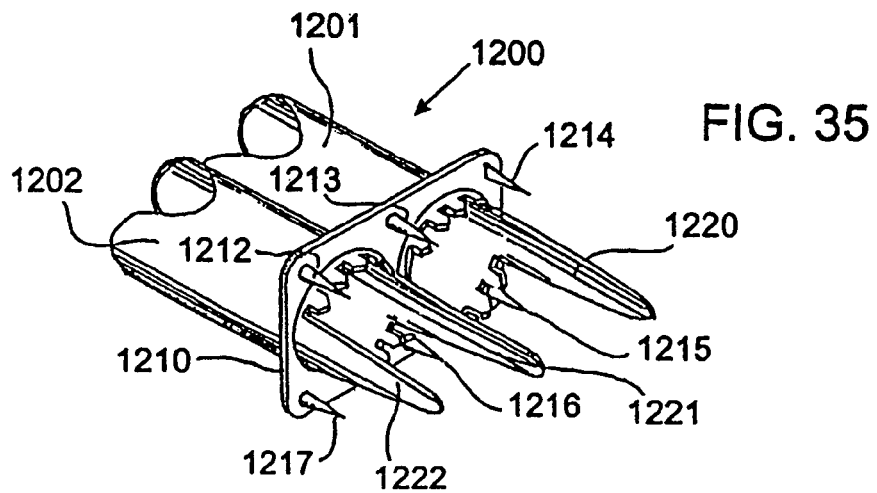
FIG. 35 is a perspective side view of a Dual Extended Outer Sleeve having uneven extended portions which decrease in height in the direction insertion.

Referring to FIG. 35, a second Dual Extended Outer Sleeve 1200, is shown. The Dual Extended Outer Sleeve 1200 is similar to the Dual Extended Outer Sleeve 1100, except that it has additional extended portions 1220 and 1222 which have a height that is greater near the distal end 1204 of the hollow tubular members 1201 and 1202 and decreases in the direction away from the hollow tubular members 1201 and 1202. The extended portions 1220-1222 are similar in shape and function to the extended portions 920 and 922 described above in reference to FIG. 31. Moreover, as the foot plate 1210 is rectangular and larger than foot plate 1110, additional prong 1216 and 1217 may be added.

Further, it should be appreciated that the lordotic distractor for use posteriorly when referring to their use in the lumbar spine, would be used anteriorly if applied to the thoracic spine, either in the single or double-barrel form. This is because the thoracic spine is normally curved into kyphosis which is the reverse of lordosis. That is, in approaching the thoracic spine anteriorly, it would be desirable to distract the back of the disc space more than the front, and that would require an Extended Outer Sleeve which would resemble that seen in FIG. 30; though when used in this new context, it would more correctly be referred to as an Anterior Thoracic Kyphotic Extended Outer Sleeve. As with the Posterior Lordotic Outer Sleeve, the Posterior and Anterior Long Lordotic Posterior Short Lordotic Distractor and Anterior Short Lordotic Distractors, though referred to previously as lordotic when placed into the lumbar spine from the posterior approach, would now more correctly, when placed in the thoracic spine from the anterior approach be called Kyphotic Thoracic Distractors.

It can readily be appreciated that the described Extended Outer Sleeves may be used with the Short and Long Distractors having a disc penetrating portion of uniform diameter or in combination with the lordotic and kyphotic distractors of complimentary configuration.

Referring to FIGS. 36-41, shown is the apparatus 1350 for use in installing an improved interbody spinal fusion implant 1300 having one or more flat sides as disclosed in co-pending application filed on Feb. 17, 1995, entitled IMPROVED INTERBODY SPINAL FUSION IMPLANTS which is incorporated herein by reference. The apparatus 1350 comprises a Dual Outer Sleeve 1310 having a pair of overlapping, hollow cylindrical tubes 1352 and 1354 identical in size and each having an internal diameter slightly larger than the outer diameter of the spinal fusion implant 1300. The cylindrical tubes 1352, 1354 are in communication with each other along their length and are displaced from each other ideally a distance that is slightly greater than the sum of the diameters of two spinal fusion implants 1300 placed side-by-side with the flat sides 1302 of each spinal fusion implant 1300 touching. The cylindrical tubes 1352 and 1354 are joined longitudinally such that they are partially overlapping. The hollow cylindrical tubes 1352 and 1354 are mounted on a foot plate 1362 similar to the foot plate described in FIG. 35. There are a series of prongs 1364a-1364f projecting from the bottom 1366 of the foot plate 1360 which are used to engage the Dual Outer Sleeve 1310 to the base of the adjacent vertebrae V.

Referring specifically to FIG. 36, the apparatus 1350 is introduced over two Long Distractors 1320 and 1322 placed side-by-side and protruding anteriorly from the vertebrae V. The Long Distractors 1320 and 1322 are similar to the Long Distractor 100 described above except that they have a flat side 1324 and 1326, respectively.

Referring to FIGS. 37 and 38, in one embodiment, the foot plate 1360 is essentially rectangular, but without sharp corners. It is appreciated by those skilled in the art, that other shapes can be utilized.

As shown in FIGS. 36 and 39, the foot plate 1360 is contoured so as to approximate the external curvature of the vertebrae V anteriorly. Extending forward from foot plate 1360 are the multiple sharp prongs 1364a-1364f which are sufficiently long to permit fixation of the foot plate 1360 to the vertebrae V. The prongs 1364a-1364f are limited in length so as to not penetrate the vertebrae V too far posteriorly and number from 2 to 10, but preferably 6.

Referring to FIG. 39, as the Dual Outer Sleeve 1350 is driven forward, the prongs 1364a-1364f extending from foot plate 1360 are embedded into the opposed vertebrae V until their forward motion is inhibited by the foot plate 1360 becoming congruent to and being stopped by, the anterior aspect of the vertebrae V.

As shown in FIG. 36, once the apparatus 1350 has been fully seated, the vertebrae V adjacent the interspace D to be fused are rigidly held via foot plate 1360 and the prongs 1364a-1364f. Thus, it is possible to remove either one, or if desired, both of the long distractors 1320 and 1322. The dual outer sleeve has been described above for inserting two implants each having at least one flat side, may have extended portions for intradiscal insertion which are capable of producing distraction as well as kyphosis or lordosis as previously described with such extensions extending in line with the lateral walls of the cylindrical tubes.

Figure 40:
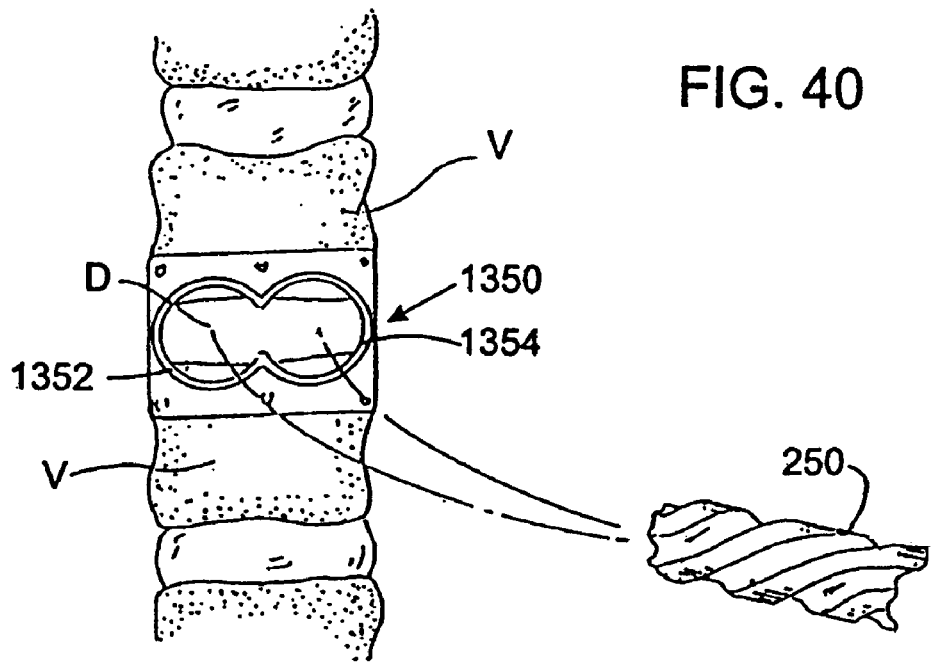
FIG. 40 illustrates a step of the method of drilling a hole into a vertebrae with the apparatus of the present invention for use in installing interbody spinal implants having one or more flat sides, shown engaged to two adjacent vertebrae of a spinal column.

Referring to FIG. 40, once the Dual Outer Sleeve 1350 has been fully seated, one of the Long Distractors 1320 and 1322 is removed and the surgeon may drill the interspace D utilizing drill 250 using each of the hollow cylinders 1352, 1354 to guide the drill 250 in order to create overlapping holes in which the spinal fusion implants 1300a and 1300b may be inserted. It is also appreciated by those skilled in the art, that a hollow inner sleeve (not shown) may be inserted into the hollow cylinders 1352, 1354 through which the drilling is performed or the Long Distractors may be left in place and a hollow trephine that fits over each of the Long Distractors 1320 and 1322 may be used to drill the interspace D. It is readily appreciated that the tubular members can be of a variety of shapes and sizes. Further, the removal of disc and bone may be accomplished by the use of a burr, or a chisel of appropriate shape for that purpose and with or without the use of a drill. The implants would then have shapes appropriate for use in the spaces so formed.

Figure 41:
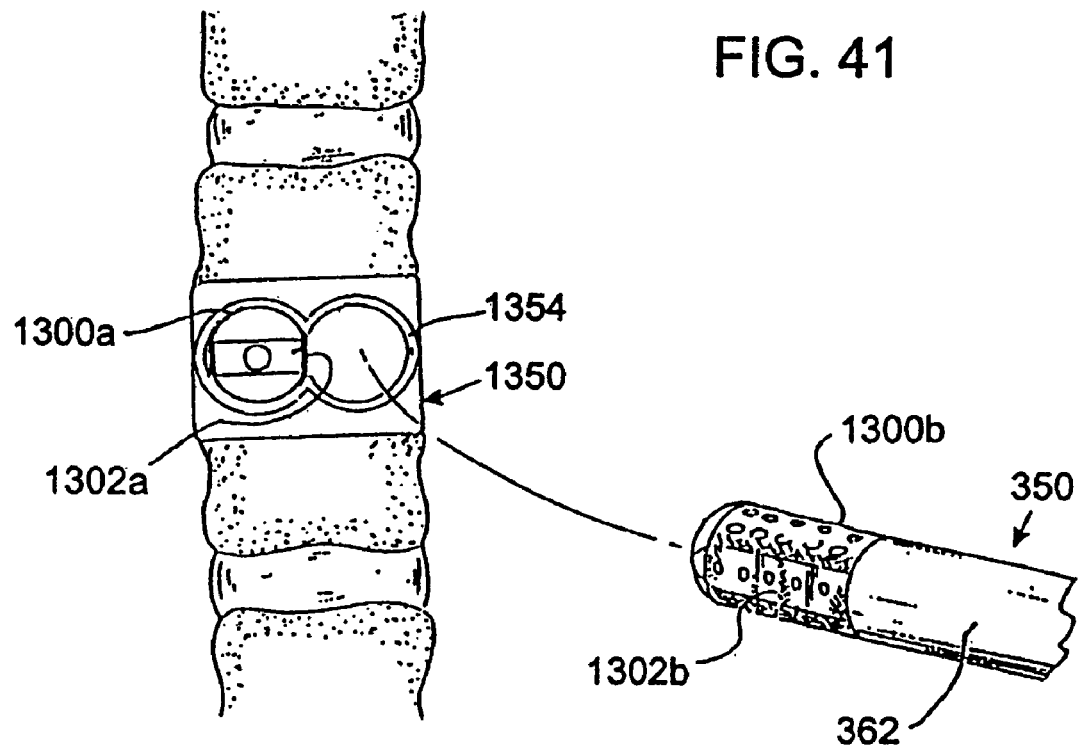
FIG. 41 illustrates a step of the method of the present invention for inserting a second interbody spinal implant having one or more flat sides into the interspace between two adjacent vertebrae with one implant shown already installed in place.

Referring to FIG. 41, once the interspace D has been drilled, an implant Driver 350 described above is used to insert the spinal fusion implants 1300a and 1300b preferably by linear advancement. The implant driver instrument 350 may be used to either insert or to remove the spinal fusion implants 1300a and 1300b.

Once affixed to the implant Driver 350, the spinal fusion implant 1300a is then introduced through one of the hollow cylindrical tubes 1352, 1354 and driven into the interspace D by the application of an impaction force transmitted through the implant driver instrument 350. Once the spinal fusion implant 1300a is inserted into the interspace D, the surface roughenings of the outer surface of the spinal fusion implant 1300a engage the bone of the vertebrae V and the implant Driver 350 is detached from the spinal fusion implant 1300a. The implant driver instrument 350 is then withdrawn from the Dual Outer Sleeve 1350 and the spinal fusion implant 1300a is fully installed and inset in the interspace D as shown in FIG. 41.

Once a first spinal fusion implant 1300a is inserted into the interspace D, a second spinal fusion implant 1300b is driven into the interspace D so that the flat side 1302a or 1302b of each spinal fusion implant 1300a and 1300b are adjacent to each other and are touching. In this manner, two spinal fusion implants 1300a and 1300b are implanted within the interspace D and engage the bone of the adjacent vertebrae V without exceeding the width of the spinal column. It is appreciated that there are other ways that two spinal implants can have complimentary shapes and that they can be inserted by linear advancement through a single (both at once) or dual outer sleeve having intradiscal extended members for stabilization, distraction, and/or to effect lordosis or kyphosis.

While the present invention has been described in association with the implant of a threaded spinal implant, it is recognized that other forms of implants may be used with the present method. For example, dowels, made from bone or artificial materials, knurled or irregularly shaped cylinders or partial cylinders, or any other shaped implants that can be introduced through the outer sleeve may be used. Being able to perform the procedure through the outer sleeve permits the procedure to be performed safely and quickly, and more accurately.

I claim:

1. A method of maintaining distraction of a spinal disc space, the method comprising:
   exposing a portion of the spine at the disc space;
   distracting the disc space to a desired height with a first distractor;
   selecting second and third distractors each having an extension and a shaft connected to the extension, the extensions each having a height between a top surface and a bottom surface that corresponds to the distracted disc space height, the extensions each further having a length extending between a leading end and a trailing end thereof;
   inserting the extension of one of the second and third distractors into the disc space through the first distractor;
   removing the one of the second and third distractors from the disc space through the first distractor; and
   performing subsequent procedures in the disc space.

2. The method according to claim 1, wherein the selecting the second and third distractors act further comprises selecting the second and third distractors with the extension lengths are sized to correspond to the depth of the disc space.

3. The method according to claim 1, wherein the height to width ratio of each of the extensions is greater than about three.

4. The method according to claim 1, wherein the performing subsequent procedures in the disc space act further comprises forming, through the first distractor, an opening across at least a portion of the disc space.

5. The method according to claim 4, wherein the forming act comprises milling the opening.

6. The method according to claim 4, wherein the forming act comprises drilling the opening.

7. The method according to claim 6, wherein the forming act further comprises placing a drill having a diameter greater than the height of the disc space through the first distractor prior to the act of drilling.

8. The method according to claim 6, wherein the forming act further comprises placing a drill through the first distractor prior to the act of drilling.

9. The method according to claim 8, wherein the performing subsequent procedures in the disc space act further comprises removing the drill from the disc space after the forming act is complete.

10. The method according to claim 4, further comprising inserting an implant into the opening.

11. The method according to claim 10, wherein the inserting an implant act comprises attaching a driving member to the implant, and using the driving member to insert the implant into the opening through the first distractor.

12. The method according to claim 11, further comprising removing the driving member from the implant after the inserting an implant act.

13. The method according to claim 12, wherein the driving member is removed through the first distractor after the inserting an implant act.

14. The method according to claim 13, further comprising removing the first distractor from the disc space after the inserting an implant act.

15. The method according to claim 10, further comprising loading the implant with fusion promoting material prior to the inserting an implant act.

16. The method according to claim 15, wherein the fusion promoting material includes bone.

17. The method according to claim 4, wherein the forming an opening act comprises removing bone from at least a portion of each vertebral body adjacent the disc space.

18. The method according to claim 17, wherein the bone is removed from each of the adjacent vertebral bodies simultaneously.

19. The method according to claim 18, further comprising removing a portion of each adjacent vertebral body through the first distractor.

* * * * *